(12) United States Patent
Bhattacharjee et al.

(10) Patent No.: US 9,187,749 B2
(45) Date of Patent: Nov. 17, 2015

(54) METHODS FOR MODULATING FACTOR 12 EXPRESSION

(75) Inventors: Gourab Bhattacharjee, San Diego, CA (US); Alexey Revenko, San Diego, CA (US); Robert A. MacLeod, San Diego, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 38 days.

(21) Appl. No.: 14/124,621

(22) PCT Filed: Jun. 8, 2012

(86) PCT No.: PCT/US2012/041747
§ 371 (c)(1),
(2), (4) Date: Feb. 28, 2014

(87) PCT Pub. No.: WO2012/170947
PCT Pub. Date: Dec. 13, 2012

(65) Prior Publication Data
US 2014/0228300 A1 Aug. 14, 2014

Related U.S. Application Data

(60) Provisional application No. 61/495,943, filed on Jun. 10, 2011, provisional application No. 61/496,456, filed on Jun. 13, 2011.

(51) Int. Cl.
| | | |
|---|---|---|
| *C12N 15/11* | (2006.01) | |
| *C12N 15/113* | (2010.01) | |
| *A61K 48/00* | (2006.01) | |
| *A61K 31/7088* | (2006.01) | |
| *A61K 45/06* | (2006.01) | |

(52) U.S. Cl.
CPC ........ *C12N 15/1137* (2013.01); *A61K 31/7088* (2013.01); *A61K 45/06* (2013.01); *A61K 48/005* (2013.01); *C12N 15/113* (2013.01); *C12N 2310/11* (2013.01); *C12N 2310/315* (2013.01); *C12N 2310/3231* (2013.01); *C12N 2310/3341* (2013.01); *C12N 2310/341* (2013.01)

(58) Field of Classification Search
CPC ........... C12N 2310/11; C12N 2310/31; C12N 2310/32; C12N 2310/33
See application file for complete search history.

(56) References Cited

U.S. PATENT DOCUMENTS

| | | | |
|---|---|---|---|
| 5,801,154 | A | 9/1998 | Baracchini et al. |
| 6,268,490 | B1 | 7/2001 | Imanishi et al. |
| 6,525,191 | B1 | 2/2003 | Ramasamy |
| 6,582,908 | B2 | 6/2003 | Fodor et al. |
| 6,670,461 | B1 | 12/2003 | Wengel et al. |
| 6,770,748 | B2 | 8/2004 | Imanishi et al. |
| 6,794,499 | B2 | 9/2004 | Wengel et al. |
| 7,034,133 | B2 | 4/2006 | Wengel et al. |
| 7,053,207 | B2 | 5/2006 | Wengel |
| 7,399,845 | B2 | 7/2008 | Seth et al. |
| 7,427,672 | B2 | 9/2008 | Imanishi et al. |
| 7,547,684 | B2 | 6/2009 | Seth et al. |
| 7,696,345 | B2 | 4/2010 | Allerson et al. |
| 2001/0053519 | A1 | 12/2001 | Fodor et al. |
| 2003/0228597 | A1 | 12/2003 | Cowsert et al. |
| 2004/0171570 | A1 | 9/2004 | Allerson et al. |
| 2005/0130923 | A1 | 6/2005 | Bhat et al. |
| 2007/0031844 | A1 | 2/2007 | Khvorova et al. |
| 2007/0192882 | A1* | 8/2007 | Dewald ........................... 800/14 |
| 2008/0039618 | A1 | 2/2008 | Allerson et al. |
| 2008/0254039 | A1 | 10/2008 | Nieswandt et al. |
| 2009/0012281 | A1 | 1/2009 | Swayze et al. |
| 2009/0064350 | A1 | 3/2009 | Dewald |
| 2010/0137414 | A1 | 6/2010 | Freier et al. |
| 2010/0324114 | A1 | 12/2010 | Dewald |
| 2011/0067124 | A1* | 3/2011 | Dewald ........................... 800/13 |
| 2012/0309035 | A1* | 12/2012 | Lindahl et al. .................. 435/13 |
| 2013/0331434 | A1* | 12/2013 | Monia et al. ................ 514/44 A |

FOREIGN PATENT DOCUMENTS

| | | |
|---|---|---|
| WO | WO 99/14226 | 3/1999 |
| WO | WO 03/004602 | 1/2003 |
| WO | WO 2004/106356 | 12/2004 |
| WO | WO 2005/021570 | 3/2005 |
| WO | WO 2007/134181 | 11/2007 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2009/115478 | 9/2009 |
| WO | WO 2010/094732 | 8/2010 |

(Continued)

OTHER PUBLICATIONS

Donald Kyle Current Pharmaceutical Design 1995 1 233-254.*
Merriam-Webster [online] [retrieved on Mar. 5, 2015] defintion for prophylactically. Retrieved from: Google, pp. 1-3.*
Cugno et al. Trends Mol. Med. 15:69-78, 2009.*
Adcock et al., "A laboratory approach to the evaluation of hereditary hypercoagulability" Am. J. Clin. Pathol. (1997) 108(4):434-449.

(Continued)

*Primary Examiner* — Brian Whiteman
(74) *Attorney, Agent, or Firm* — Knobbe, Martens, Olson & Bear LLP

(57) ABSTRACT

Disclosed herein are methods for decreasing Factor 12 and treating or preventing inflammatory conditions in an individual in need thereof. Examples of disease conditions that can be ameliorated with the administration of antisense compounds targeted to Factor 12 include hereditary angioedema (HAE). Methods for inhibiting Factor 12 can also be used as a prophylactic treatment to prevent individuals at risk for developing an inflammatory condition, such as, hereditary angioedema.

22 Claims, 2 Drawing Sheets

(56) References Cited

FOREIGN PATENT DOCUMENTS

Figure 1:
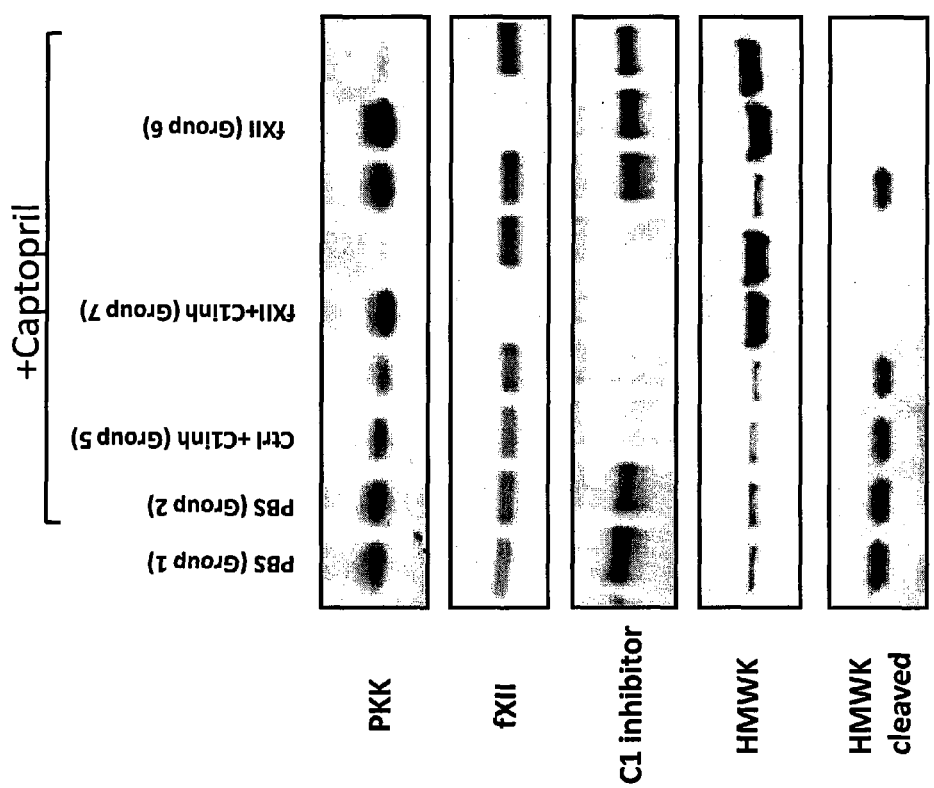

| WO | WO 2010/111702 | 9/2010 |
|----|----------------|--------|
| WO | WO 2012/064758 | 5/2012 |
| WO | WO 2012/170947 | 12/2012 |

OTHER PUBLICATIONS

Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.

Altmann et al., "Second-generation antisense oligonucleoties: structure-activity relationships and the design of improved signal-transduction inhibitors" Biochem. Soc. Trans. (1996) 24: 630-637.

Altmann et al., "Second Generation of Antisense Oligonucleotides: From Nuclease Resistance to Biological Efficacy in Animals" Chimia (1996) 50: 168-176.

Altmann et al., "Second Generation Antisense Oligonucleotides—Inhibition of PKC-a and c-RAF Kinase Expression by Chimeric Oligonucleotides Incorporating 5'-Substituted Carbocyclic Nucleosides and 2'-O-Ethylene Glycol Substituted Ribonucleosides" Nucleosides Nucleotides (1997) 16(7-9): 917-926.

Altschul et al., "Basic Local Alignment Search Tool" J. Mol. Biol. (1990) 215: 403-410.

Aulak et al., "Chymotrypsin inhibitory activity of normal C1-inhibitor and a P1 Arg to His mutant: evidence for the presence of overlapping reactive centers." Protein Sci. (1993) 2(5): 727-732.

Bertina et al., "Mutation in blood coagulation factor V associated with resistance to activated protein C." Nature (1994) 369(6475):64-67.

Bjork et al., "Mechanism of the anticoagulant action of heparin." Mol Cell Biochem. (1982) 48(3): 161-182.

Bouillet et al. "Disease expression in women with hereditary angioedema" Am. J. Obstet. Gynecol. (2008) 199: 484.e1-484.e4.

Braasch et al., "Locked nucleic acid (LNA): fine-tuning the recognition of DNA and RNA" Chem. Biol. (2001) 8:1-7.

Branch et al., "A good antisense molecule is hard to find," TIBS (1998) 23:45-50.

Chan et al., "The inhibition of activated factor XII (hageman factor) by antithrombin III: The effect of other plasma proteinase inhibitors" Biochem. Biophys. Res. Comm. (1977) 74(1): 150-158.

Cichon et al., "Increased activity of coagulation factor XII (Hageman factor) causes hereditary angioedema type III." Am. J. Hum. Genet. (2006) 79: 1098-1104.

Citarella et al., "The Second Exon-Encoded Factor XII Region Is Involved in the Interaction of Factor XII With Factor XI and Does Not Contribute to the Binding Site for Negatively Charged Surfaces" Blood (1998) 92: 4198-4206.

Citarella et al., "Identification of a putative binding site for negatively charged surfaces in the fibronectin type II domain of human factor XII—an immunochemical and homology modeling approach." Thromb. Haemost. (2000) 84(6): 1057-1065.

Crooke et al., "Basic Principles of Antisense Therapeutics" Antisense Research and Application (1998) Chapter 1:1-50.

Drake et al., "Selective cellular expression of tissue factor in human tissues. Implications for disorders of hemostasis and thrombosis." Am J Pathol (1989) 134(5):1087-1097.

Elayadi et al., "Applications of PNA and LNA oligomers to chemotherapy" Curr. Opinion Invest. Drugs (2001) 2:558-561.

Esnouf et al., "A monoclonal antibody raised against human beta-factor XIIa which also recognizes alpha-factor XIIa but not factor XII or complexes of factor XIIa with C1 esterase inhibitor." Thromb. Haemost. (2000) 83(6): 874-881.

Farsetti et al., "Orphan receptor hepatocyte nuclear factor-4 antagonizes estrogen receptor alpha-mediated induction of human coagulation factor XII gene." Endocrinology (1998) 139(11): 4581-4589.

Foster et al., "Inhibition of the activation of Hageman factor (factor XII) and of platelet aggregation by extracts of Brugia malayi microfilariae." J. Lab. Clin. Med. (1991) 117(5): 344-352.

Foster et al., "Inhibition of the activation of Hageman factor (factor XII) by extracts of Schistosoma mansoni." J. Lab. Clin. Med. (1992) 120(5): 735-9.

Freier et al., "The ups and downs of nucleic acid duplex stability: structure-stability studies on chemically-modified DNA:RNA duplexes" Nucleic Acids Research (1997) 25(22):4429-4443.

Frieden et al., "Expanding the design horizon of antisense oligonucleotides with alpha-L-LNA" Nucleic Acids Research (2003) 31(21):6365-6372.

Gautschi et al., "Activity of a Novel bcl-2/bcl-xL-Bispecific Antisense Oligonucleotide Against Tumors of Diverse Histologic Origins" J. Natl. Cancer Inst. (2001) 93(6):463-471.

Gigli et al., "Interaction of plasma kallikrein with the C1 inhibitor." J. Immunol. (1970) 104:574-581.

Han et al., "Increased vascular permeability in C1 inhibitor-deficient mice mediated by the bradykinin type 2 receptor." J. Clin. Invest. (2002) 109: 1057-1063.

Hazegh-Azam et al., "The Corn Inhibitor of Activated Hageman Factor: Purification and Properties of Two Recombinant Forms of the Protein" Protein Expr. Purif. (1998) 13(2): 143-149.

Hojima et al., "Pumpkin seed inhibitor of human factor XIIa (activated Hageman factor) and bovine trypsin" Biochemistry (1982) 21(16): 3741-3746.

Isawa et al., "Identification and characterization of plasma kallikrein-kinin system inhibitors from salivary glands of the blood-sucking insect Triatoma infestans." FEBS J. (2007) 274(16): 4271-4286.

Kaplan et al., "Pathways for bradykinin formation and inflammatory disease." J. Allergy Clin. Immunol. (2002) 109(2): 195-209.

Kato et al., "Identification and characterization of the plasma kallikrein-kinin system inhibitor, haemaphysalin, from hard tick, Haemaphysalis longicornis" Thromb. Haemost. (2005) 93: 359-67.

Kleinschnitz et al., "Targeting coagulation factor XII provides protection from pathological thrombosis in cerebral ischemia without interfering with hemostasis" J. Exper. Med. (2006) 203:513-518.

Koshkin et al., "LNA (Locked Nucleic Acids): Synthesis of the Adenine, Cytosine, Guanine, 5-Methylcytosine, Thymine and Uracil Biocyclonucleoside Monomers, Oligomerisation, and Unprecedented Nucleic Acid Recognition" Tetrahedron (1998) 54:3607-3630.

Kumar et al., "The First Analogues of LNA (Locked Nucleic Acids): Phosphorothioate-LNA and 2'-Thio-LNA" Bioorg. Med. Chem. Lett. (1998) 8:2219-2222.

Leumann, "DNA Analogues: From Supramolecular Principles to Biological Properties" Bioorganic & Medicinal Chemistry (2002) 10:841-854.

Mackenzie et al., "Plasma prekallikrein levels are positively associated with circulating lipid levels and the metabolic syndrome in children." Appl. Physiol. Nutr. Metab. (2010) 35: 518-525.

Mahdi et al., "Factor XII interacts with the multiprotein assembly of urokinase plasminogen activator receptor, gC1qR, and cytokeratin 1 on endothelial cell membranes" Blood (2002) 99(10): 3585-3596.

Maher et al., "Comparative hybrid arrest by tandem antisense oligodeoxyribonucleotides or oligodeoxyribonucleoside methylphosphonates in a cell-free system" Nuc. Acid. Res. (1988) 16:3341-3358.

Martin, "Ein neuer Zugang zu 2'-O-Alkylribonucleosiden and Eigenschaften eren Oligonucleotide" Helv. Chim. Acta (1995) 78: 486-504.

New England Biolabs 1998/99 Catalog (cover page and pp. 121 and 284).

Nielsen, "Corn trypsin inhibitor decreases tissue-type plasminogen activator-mediated fibrinolysis of human plasma." Blood Coagul. Fibronolysis. (2009) 20(3): 191-196.

Nishikawa et al., "Effect of neurotropin® on the activation of the plasma kallikrein-kinin system" Biochem. Pharmacol. (1992) 43(6): 1361-1369.

Niwano et al., "Inhibitory action of amyloid precursor protein against human Hageman factor (factor XII)." J. Lab. Clin. Med. (1995) 125(2): 251-256.

Orum et al., "Locked nucleic acids: A promising molecular family for gene-function analysis and antisense drug development" Curr. Opinion Mol. Ther. (2001) 3(3):239-243.

(56) References Cited

OTHER PUBLICATIONS

Rajapakse et al., "A novel anticoagulant purified from fish protein hydrolysate inhibits factor XIIa and platelet aggregation." Life Sci. (2005) 76(22): 2607-2619.

Ratnoff et al., "Inhibition of the activation of hageman factor (factor XII) by eosinophils and eosinophilic constituents" Am. J. Hematol. (1993) 42(1): 138-145.

Reynolds et al., "Rational siRNA design for RNA interference" Nature Biotechnology (2004) 22(3):326-330.

Ryder et al., "The effect of chemical modification of basic amino acid residues on the activation and amidolytic activity of Hageman factor (factor XII)." J. Lab. Clin. Med. (1993) 122(6): 697-702.

Sampaio et al., "Plant serine proteinase inhibitors. Structure and biochemical applications on plasma kallikrein and related enzymes." Immunopharmacology (1996) 32(1-3): 62-66.

Sanghvi et al., "Heterocyclic Base Modifications in Nucleic Acids and Their Applications in Antisense Oligonucleotides" Antisense Research and Applications (1993) pp. 273-288.

Schousboe et al., "Synchronized inhibition of the phospholipid mediated autoactivation of factor XII in plasma by beta 2-glycoprotein I and anti-beta 2-glycoprotein I." Thromb. Haemost (1995) 73(5): 798-804.

Schwartz et al., "Tissue factor pathway inhibitor endocytosis." Trends Cardiovasc Med. (1997) 7(7):234-239.

Scott et al., "Alpha-1-antitrypsin-Pittsburgh. A potent inhibitor of human plasma factor XIa, kallikrein, and factor XIIf." J. Clin. Invest. (1986) 77(2): 631-634.

Singh et al., "LNA (locked nucleic acids): synthesis and high-affinity nucleic acid recognition" Chem. Commun. (1998) 4:455-456.

Singh et al., "Synthesis of 2'-Amino-LNA: A Novel Conformationally Restricted High-Affinity Oligonucleotide Analogue with a Handle" J. Org. Chem. (1998) 63:10035-10039.

Srivastava et al., "Five- and Six-Membered Conformationally Locked 2',4'-Carbocyclic ribo-Thymidines: Synthesis, Structure, and Biochemical Studies" J. Am. Che,. Soc. (2007) 129:8362-8379.

Tanabe et al., "Isolation and Characterization of Streptoverticillium Anticoagulant (SAC), a Novel Protein Inhibitor of Blood Coagulation Produced by Streptoverticillium cinnamoneum subsp. Cinnamoneum" J. Biochem. (1994) 115(4): 743-751.

Wahlestedt et al., "Potent and nontoxic antisense oligonucleoties containing locked nucleic acids" PNAS (2000) 97(10):5633-5638.

Woolf et al., "Specificity of antisense oligonucleotides in vivo" PNAS (1992) 89:7305-7309.

Zhang e al., "PowerBLAST: A New Network BLAST Application for Interactive or Automate Sequence Analysis and Annoation", Genome Res. (1997) 7: 649-656.

Zhou et al., "Fine Tuning of Electrostatics around the Internucleoside Phosphate through Incorporation of Modified 2',4'-Carbocylic-LNAs and -ENAs Leads to Significant Modulation of Antisense Properties" J. Org. Chem. (2009) 74: 118-134.

Zuraw, "Hereditary Angioedema" N. Engl. J. Med. (2008) 359: 1027-36.

International Search Report for application PCT/US11/59804 dated May 14, 2012.

International Search Report for application PCT/US2012/041747 dated Dec. 10, 2012.

Yau et al., "Selective depletion of factor XI or factor XII with antisense oligonucleotides attenuates catheter thrombosis in rabbits", Blood, vol. 123, No. 13, pp. 2102-2107, Mar. 27, 2014.

\* cited by examiner

METHODS FOR MODULATING FACTOR 12 EXPRESSION

CROSS REFERENCED TO RELATED APPLICATIONS

This application is a U.S. National Phase filing under 35 U.S.C. §371 claiming priority to International Serial No. PCT/US2012/041747 filed Jun. 8, 2012, which claims priority to U.S. Provisional Application No. 61/495,943, filed Jun. 10, 2011 and U.S. Provisional Application No. 61/496,456, filed Jun. 13, 2011, each of which is incorporated herein by reference in its entirety.

SEQUENCE LISTING

The present application is being filed along with a Sequence Listing in electronic format. The Sequence Listing is provided as a file entitled BIOL0154USASEQ.txt, created Nov. 8, 2013, which is 122 Kb in size. The information in the electronic format of the sequence listing is incorporated herein by reference in its entirety.

FIELD

Provided are methods for reducing expression of Factor 12 mRNA and protein in an animal. Such methods are useful to treat, prevent, or ameliorate inflammatory conditions, including hereditary angioedema (HAE).

BACKGROUND

Inflammation

Inflammation is a complex biological process of the body in response to an injury or abnormal stimulation caused by a physical, chemical, or biological stimulus. Inflammation is a protective process by which the body attempts to remove the injury or stimulus and begins to heal affected tissue in the body.

The inflammatory response to injury or stimulus is characterized by clinical signs of increased redness (rubor), temperature (calor), swelling (tumor), pain (dolor) and/or loss of function (functio laesa) in a tissue. Increased redness and temperature is caused by vasodilation leading to increased blood supply at core body temperature to the inflamed tissue site. Swelling is caused by vascular permeability and accumulation of protein and fluid at the inflamed tissue site. Pain is due to the release of chemicals (e.g. bradykinin) at the inflamed tissue site that stimulate nerve endings. Loss of function may be due to several causes.

Inflammation is now recognized as a type of non-specific immune response to an injury or stimulus. The inflammatory response has a cellular component and an exudative component. In the cellular component, resident macrophages at the site of injury or stimulus initiate the inflammatory response by releasing inflammatory mediators such as TNFalpha, IFNalpha IL-1, IL-6, IL12, IL-18 and others. Leukocytes are then recruited to move into the inflamed tissue area and perform various functions such as release of additional cellular mediators, phagocytosis, release of enzymatic granules, and other functions. The exudative component involves the passage of plasma fluid containing proteins from blood vessels to the inflamed tissue site. Inflammatory mediators such as bradykinin, nitric oxide, and histamine cause blood vessels to become dilated, slow the blood flow in the vessels, and increase the blood vessel permeability, allowing the movement of fluid and protein into the tissue. Biochemical cascades are activated in order to propagate the inflammatory response (e.g., complement system in response to infection, fibrinolysis and coagulation systems in response to necrosis due to a burn or trauma, kinin system to sustain inflammation) (Robbins Pathologic Basis of Disease, Philadelphia, W.B Saunders Company).

Inflammation can be acute or chronic. Acute inflammation has a fairly rapid onset, quickly becomes severe, and quickly and distinctly clears after a few days to a few weeks. Chronic inflammation can begin rapidly or slowly and tends to persist for weeks, months, or years with a vague and indefinite termination. Chronic inflammation can result when an injury or stimulus, or products resulting from its presence, persists at the site of injury or stimulation and the body's immune response is not sufficient to overcome its effects.

Inflammatory responses, although generally helpful to the body to clear an injury or stimulus, can sometimes cause injury to the body. In some cases, a body's immune response inappropriately triggers an inflammatory response where there is no known injury or stimulus to the body. In these cases, categorized as autoimmune diseases, the body attacks its own tissues causing injury to its own tissues.

Hereditary angioedema

Hereditary angioedema (HAE) is a rare inflammatory disease characterized by recurrent episodes of swelling around the head and extremities (Zuraw, B. L. N. Engl. J. Med. 359: 1027-36, 2008). Angioedema attacks occur with unpredictable frequency and are typically focused on the skin, and gastric, oropharyngeal, and laryngeal mucosas. Asphyxiation due to laryngeal swelling can result in mortality. HAE is caused by deficiency or malfunction of the serine protease inhibitor C1-INH (Kaplan, A. P. et al. J. Allergy Clin. Immunol. 109: 195-209, 2002). C1-INH is the primary inhibitor of coagulation factors 12 and 11 (Factor 11) of the intrinsic coagulation pathway as well as plasma kallikrein (Gigli, I. et al. J. Immunol. 104:574-581, 1970). C1-INH mediated inhibition of plasma kallikrein and Factor 12 results in inactivation of the kallikrein pathway and decreased levels of bradykinin (BK). C1-INH deficiency or dysfunction results in overproduction of BK, which is the mechanism by which HAE attacks are believed to occur. Type III HAE has been linked with mutations in the Factor 12 gene, which encodes coagulation protein Factor 12 (Cichon, S. et al. Am. J. Hum. Genet. 79: 1098-1104, 2006).

The kinin-kallikrein pathway consists of several proteins that play a role in inflammation, blood pressure control, coagulation, and pain. Plasma prekallikrein is the precursor of plasma kallikrein, which in turn liberates kinins from kininogens and also generates plasmin from plasminogen. Plasma prekallikrein is converted to plasma kallikrein by Factor 12a by the cleavage of an internal Arg-Ile peptide bond. Plasma prekallikrein, in turn, is the product of the KLKB1 gene (MacKenzie, J. A. et al. Appl. Physiol. Nutr. Metab. 35: 518-525, 2010. Plasma kallikrein works in association with Factors 11 and 12.

There is currently no animal model which directly replicates HAE. However, the increased vascular permeability associated with HAE has been replicated in rodent models with agents such as the angiotensin converting enzyme (ACE) inhibitor captopril, as well as the C1-INH knockout mouse (Han, E. D. et al. J. Clin. Invest. 109: 1057-1063, 2002).

SUMMARY

Provided herein are methods for modulating expression of Factor 12 mRNA and protein. In certain embodiments, Factor 12 specific inhibitors modulate expression of Factor 12 mRNA and protein. In certain embodiments, Factor 12 specific inhibitors are nucleic acids, proteins, or small molecules.

In certain embodiments, modulation can occur in a cell or tissue. In certain embodiments, the cell or tissue is in an animal. In certain embodiments, the animal is a human. In certain embodiments, Factor 12 mRNA levels are reduced. In certain embodiments, Factor 12 protein levels are reduced. In certain embodiments, Factor 12 mRNA and protein levels are reduced. Such reduction can occur in a time-dependent manner or in a dose-dependent manner.

Also provided are methods useful for preventing, treating, and ameliorating diseases, disorders, and conditions. In certain embodiments, such diseases, disorders, and conditions are inflammatory conditions. In certain embodiments, the inflammatory condition may be an acute or chronic inflammatory condition. In certain embodiments, such inflammatory conditions may include hereditary angioedema (HAE), edema, angioedema, swelling, angioedema of the lids, ocular edema, macular edema, and cerebral edema.

Such diseases, disorders, and conditions can have one or more risk factors, causes, or outcomes in common. Certain risk factors and causes for development of an inflammatory condition include genetic predisposition to an inflammatory condition and environmental factors. In certain embodiments, a defect in an individual's genetic code for complement 1 esterase inhibitor (i.e., C1-INH, a protein that helps to regulate the immune system) is responsible for inflammatory conditions, such as, hereditary angioedema (HAE). In certain embodiments, genetic mutations lead to a deficiency in C1-INH (i.e., type I HAE) or an inability of existing C1-INH to function properly (i.e., type II HAE). In certain embodiments, genetic mutations in Factor 12 gene lead to hyperfunctionalization of Factor 12, which leads to hereditary angioedema (i.e., type III HAE). In certain embodiments, acquired angioedema may be the result of using angiotensin-converting enzyme inhibitors (i.e., ACE inhibitors) or angiotensin II receptor blockers (i.e., ARBs). In certain embodiments, an allergic reaction may lead to angioedema. Certain outcomes associated with development of an inflammatory condition include edema/swelling in various body parts including the extremities (i.e., hands, feet, arms, legs), the intestines (abdomen), the face, the genitals, the larynx (i.e., voice box); vascular permeability; vascular leakage; generalized inflammation; abdominal pain; bloating; vomiting; diarrhea; itchy skin; respiratory (asthmatic) reactions; rhinitis; anaphylaxis; bronchoconstriction; hypotension; coma; and death.

In certain embodiments, methods of treatment include administering a Factor 12 specific inhibitor to an individual in need thereof. In certain embodiments, the Factor 12 specific inhibitor is a nucleic acid. In certain embodiments, the nucleic acid is an antisense compound. In certain embodiments, the antisense compound is a modified oligonucleotide.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Additionally, as used herein, the use of "and" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this disclosure, including, but not limited to, patents, patent applications, published patent applications, articles, books, treatises, and GENBANK Accession Numbers and associated sequence information obtainable through databases such as National Center for Biotechnology Information (NCBI) and other data referred to throughout in the disclosure herein are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis.

Unless otherwise indicated, the following terms have the following meanings:

"2'-O-methoxyethyl" (also 2'-MOE and 2'-O(CH$_2$)$_2$—OCH$_3$) refers to an O-methoxy-ethyl modification of the 2' position of a furanosyl ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"5-methylcytosine" means a cytosine modified with a methyl group attached to the 5' position. A 5-methylcytosine is a modified nucleobase.

"About" means within ±7% of a value. For example, if it is stated, "the compounds affected at least about 70% inhibition of Factor 12", it is implied that the Factor 12 levels are inhibited within a range of 63% and 77%.

"Active pharmaceutical agent" means the substance or substances in a pharmaceutical composition that provide a therapeutic benefit when administered to an individual. For example, in certain embodiments an antisense oligonucleotide targeted to Factor 12 is an active pharmaceutical agent.

"Active target region" or "target region" means a region to which one or more active antisense compounds is targeted. "Active antisense compounds" means antisense compounds that reduce target nucleic acid levels or protein levels.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing a pharmaceutical agent to an individual, and includes, but is not limited to administering by a medical professional and self-administering.

"Amelioration" or "ameliorate" or "ameliorating" refers to a lessening of at least one indicator, sign, or symptom of an associated disease, disorder, or condition. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, snoRNAs, miRNAs, and satellite repeats.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"Bicyclic sugar" means a furanosyl ring modified by the bridging of two atoms. A bicyclic sugar is a modified sugar.

"Bicyclic nucleoside" (also BNA) means a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring.

"Cap structure" or "terminal cap moiety" means chemical modifications, which have been incorporated at either terminus of an antisense compound.

"cEt" or "constrained ethyl" means a bicyclic nucleoside having a sugar moiety comprising a bridge connecting the 4'-carbon and the 2'-carbon, wherein the bridge has the formula: 4'-CH(CH$_3$)—O-2'.

"Constrained ethyl nucleoside" (also cEt nucleoside) means a nucleoside comprising a bicyclic sugar moiety comprising a 4'-CH(CH$_3$)—O-2' bridge.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Coagulation factor" means any of factors I, II, III, IV, V, VII, VIII, IX, X, XI, XII, XIII, or TAFI in the blood coagulation cascade. "Coagulation factor nucleic acid" means any nucleic acid encoding a coagulation factor. For example, in certain embodiments, a coagulation factor nucleic acid includes, without limitation, a DNA sequence encoding a coagulation factor (including genomic DNA comprising introns and exons), an RNA sequence transcribed from DNA encoding a coagulation factor, and an mRNA sequence encoding a coagulation factor. "Coagulation factor mRNA" means an mRNA encoding a coagulation factor protein.

"Complementarity" means the capacity for pairing between nucleobases of a first nucleic acid and a second nucleic acid.

"Contiguous nucleobases" means nucleobases immediately adjacent to each other.

"Diluent" means an ingredient in a composition that lacks pharmacological activity, but is pharmaceutically necessary or desirable. For example, the diluent in an injected composition may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" means the amount of active pharmaceutical agent sufficient to effectuate a desired physiological outcome in an individual in need of the agent. The effective amount may vary among individuals depending on the health and physical condition of the individual to be treated, the taxonomic group of the individuals to be treated, the formulation of the composition, assessment of the individual's medical condition, and other relevant factors.

"Factor 12 nucleic acid" or "Factor XII nucleic acid" or "F 12 nucleic acid" or "F XII nucleic acid" or "F12 nucleic acid" means any nucleic acid encoding Factor 12. For example, in certain embodiments, a Factor 12 nucleic acid includes a DNA sequence encoding Factor 12, an RNA sequence transcribed from DNA encoding Factor 12 (including genomic DNA comprising introns and exons), and an mRNA sequence encoding Factor 12. "Factor 12 mRNA" means an mRNA encoding a Factor 12 protein.

"Factor 12 specific inhibitor" refers to any agent capable of specifically inhibiting the expression of Factor 12 mRNA and/or Factor 12 protein at the molecular level. For example, Factor 12 specific inhibitors include nucleic acids (including antisense compounds), peptides, antibodies, small molecules, and other agents capable of inhibiting the expression of Factor 12 mRNA and/or Factor 12 protein. In certain embodiments, by specifically modulating Factor 12 mRNA expression and/or Factor 12 protein expression, Factor 12 specific inhibitors may affect other components of the coagulation cascade including downstream components. Similarly, in certain embodiments, Factor 12 specific inhibitors may affect other molecular processes in an animal.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap" and the external regions may be referred to as the "wings."

"Gap-widened" means a chimeric antisense compound having a gap segment of 12 or more contiguous 2'-deoxyribonucleosides positioned between and immediately adjacent to 5' and 3' wing segments having from one to six nucleosides.

"Hybridization" means the annealing of complementary nucleic acid molecules. In certain embodiments, complementary nucleic acid molecules include an antisense compound and a target nucleic acid.

"Identifying an animal at risk for developing an inflammatory condition" means identifying an animal having been diagnosed with an inflammatory condition or identifying an animal predisposed to develop an inflammatory condition. Individuals predisposed to develop an inflammatory condition include those having one or more risk factors for inflammatory conditions, including, having a personal or family history of one or more inflammatory conditions. Such identification may be accomplished by any method including evaluating an individual's medical history and standard clinical tests or assessments.

"Identifying an animal at risk for experiencing an attack of hereditary angioedema" means identifying an animal having been diagnosed with hereditary angioedema or identifying an animal predisposed to develop hereditary angioedema. Individuals predisposed to develop hereditary angioedema include those having one or more risk factors for hereditary angioedema, including, having a personal or family history of hereditary angioedema. Such identification may be accomplished by any method including evaluating an individual's medical history and standard clinical tests or assessments.

"Immediately adjacent" means there are no intervening elements between the immediately adjacent elements.

"Individual" means a human or non-human animal selected for treatment or therapy.

"Inflammatory condition" or "inflammatory disease" or "inflammatory disorder" or "inflammatory condition" means a disease, disorder or condition related to an inflammatory response to injury or stimulus characterized by clinical signs of increased redness (rubor), temperature (calor), swelling (tumor), pain (dolor) and/or loss of function (functio laesa) in a tissue. Examples of such diseases, disorders, and conditions include hereditary angioedema (HAE).

"Inhibiting Factor 12" means reducing expression of Factor 12 mRNA and/or protein levels in the presence of a Factor 12 specific inhibitor, including a Factor 12 antisense oligonucleotide, as compared to expression of Factor 12 mRNA and/or protein levels in the absence of a Factor 12 specific inhibitor, such as a Factor 12 antisense oligonucleotide.

"Internucleoside linkage" refers to the chemical bond between nucleosides.

"Linked nucleosides" means adjacent nucleosides which are bonded together.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e., a phosphodiester internucleoside bond).

"Modified nucleobase" refers to any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleotide" means a nucleotide having, independently, a modified sugar moiety, modified internucleoside linkage, or modified nucleobase. A "modified nucleoside" means a nucleoside having, independently, a modified sugar moiety or modified nucleobase.

"Modified oligonucleotide" means an oligonucleotide comprising a modified internucleoside linkage, a modified sugar, or a modified nucleobase.

"Modified sugar" refers to a substitution or change from a natural sugar.

"Motif" means the pattern of chemically distinct regions in an antisense compound.

"Naturally occurring internucleoside linkage" means a 3' to 5' phosphodiester linkage.

"Natural sugar moiety" means a sugar found in DNA (2'-H) or RNA (2'-OH).

"Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo, or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system.

"Nucleotide" means a nucleoside having a phosphate group covalently linked to the sugar portion of the nucleoside.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intraarterial administration, intraperitoneal administration, or intracranial administration, e.g., intrathecal or intracerebroventricular administration.

"Peptide" means a molecule formed by linking at least two amino acids by amide bonds. Peptide refers to polypeptides and proteins.

"Pharmaceutical composition" means a mixture of substances suitable for administering to an individual. For example, a pharmaceutical composition may comprise one or more active pharmaceutical agents and a sterile aqueous solution.

"Pharmaceutically acceptable derivative" encompasses pharmaceutically acceptable salts, conjugates, prodrugs or isomers of the compounds described herein.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage (P=S) is a modified internucleoside linkage.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" or "preventing" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single-stranded oligonucleotide" means an oligonucleotide which is not hybridized to a complementary strand.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of a pharmaceutical agent that provides a therapeutic benefit to an individual.

"Treat" or "treating" refers to administering a pharmaceutical composition to effect an alteration or improvement of a disease, disorder, or condition.

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

Certain Embodiments

Certain embodiments provide methods for decreasing Factor 12 mRNA and protein expression.

Certain embodiments provide methods for the treatment, prevention, or amelioration of diseases, disorders, and conditions associated with Factor 12 in an individual in need thereof. Also contemplated are methods for the preparation of a medicament for the treatment, prevention, or amelioration of a disease, disorder, or condition associated with Factor 12. Factor 12 associated diseases, disorders, and conditions include inflammatory conditions. In certain embodiments, the inflammatory condition may be an acute or chronic inflammatory condition. In certain embodiments, such inflammatory conditions may include hereditary angioedema (HAE), edema, angioedema, swelling, angioedema of the lids, ocular edema, macular edema, and cerebral edema.

Certain embodiments provide for the use of a Factor 12 specific inhibitor for treating, preventing, or ameliorating a Factor 12 associated disease. In certain embodiments, Factor 12 specific inhibitors are nucleic acids (including antisense compounds), peptides, antibodies, small molecules, and other agents capable of inhibiting the expression of Factor 12 mRNA and/or Factor 12 protein.

In certain embodiments of the present invention, Factor 12 specific inhibitors are peptides or proteins, such as, but not limited to, yellowfin sole anticoagulant protein (YAP) as described in *Life Sci.* 2005. 76: 2607-19; corn inhibitor of activated Hageman factor (CHFI) as described in *Protein Expr. Purif.* 1998. 13: 143-9; corn trypsin inhibitor as described in *Blood Coagul. Fibronolysis.* 2009. 20: 191-6; triafestin-1 and triafestin-2 as described in *FEBS J.* 2007. 274: 4271-86; YHK9 and vitronectin as described in *Blood.* 2002. 99: 3585-96; torresea cearensis trypsin inhibitor as described in *Immunopharmacology.* 1996. 32: 62-6; amyloid precursor protein as described in *J. Lab. Clin. Med.* 1995. 125: 251-6; streptoverticillium anticoagulant I as described in *J. Biochem.* 1994. 115: 743-51; C1-inhibitor as described in *Protein Sci.* 1993. 2: 727-32; antithrombin III as described in *Biochem. Biophys. Res. Comm.* 1977. 74: 150-8; and alpha-1-antitrypsin-Pittsburgh as described in *J. Clin. Invest.* 1986. 77: 631-4.

In certain embodiments of the present invention, Factor 12 specific inhibitors are antibodies, such as, but not limited to, KOK5 antibody as described in *Thromb. Haemost.* 2000. 84: 1057-65; mAb 2/215 as described in *Thromb. Haemost.* 2000. 83: 874-81; B7C9 as described in *Blood.* 1998. 92: 4198-206; beta 2-glycoprotein I and anti-beta 2-glycoprotein I as described in *Thromb. Haemost.* 1995. 73: 798-804; and mAb 2/215 and mAb 201/9 as described in USPPN 2009/0304685.

In certain embodiments of the present invention, Factor 12 specific inhibitors are small molecules, such as, but not limited to, neurotropin as described in *Biochem. Pharmacol.* 1992. 43: 1361-9; haemaphysalin as described in *Thromb. Haemost.* 93: 359-67; transcription factor hepatocyte nuclear factor-4 as described in *Endocrinology.* 1998. 139: 4581-9; phenylglyoxal hydrate as described in *J. Lab. Clin. Med.* 1993. 122: 697-702; eosinophilic extracts as described in *Am. J. Hematol.* 1993. 42: 138-45; schistosome extracts as described in *J. Lab. Clin. Med.* 1992. 120: 735-9; extracts of *Brugia malayi* microfilariae as described in *J. Lab. Clin. Med.* 1991. 117: 344-52; H-D-Pro-Phe-Arg-chloromethylketone as described in USPPN US 2010/0119512; and *Curcurbita maxima* iso inhibitor as described in *Biochemistry*. 1982. 21: 3741-3746.

Certain embodiments provide for methods of treating, preventing, or ameliorating an inflammatory condition in an animal, comprising administering to the animal a therapeutically effective amount of a Factor 12 specific inhibitor, wherein the inflammatory condition is ameliorated in the animal.

In certain embodiments, the animal is a human.

In certain embodiments, the inflammatory condition is hereditary angioedema (HAE).

In certain embodiments, the Factor 12 specific inhibitor is an antisense compound. In certain embodiments, the antisense compound is a modified oligonucleotide.

In certain embodiments, the Factor 12 specific inhibitor is a nucleic acid. In certain embodiments, the nucleic acid is a modified oligonucleotide.

In certain embodiments, the Factor 12 specific inhibitor is a modified oligonucleotide.

In certain embodiments, the modified oligonucleotide consists of 12 to 30 linked nucleosides.

In certain embodiments, the modified oligonucleotide is a single-stranded oligonucleotide.

In certain embodiments, the modified oligonucleotide consists of 15, 16, 17, 18, 19, or 20 linked nucleosides.

In certain embodiments, the modified oligonucleotide has a nucleobase sequence that is 80%, 85%, 90%, 95%, or 100% complementary to a human Factor 12 nucleic acid.

In certain embodiments, the modified oligonucleotide comprises at least one modified internucleoside linkage. In certain embodiments, each modified internucleoside linkage is a phosphorothioate internucleoside linkage.

In certain embodiments, at least one nucleoside of the modified oligonucleotide comprises a modified sugar. In certain embodiments, the modified sugar is a bicyclic sugar. In certain embodiments, the bicyclic sugar comprises a 4'-CH(CH$_3$)—O-2' bridge.

In certain embodiments, the modified sugar comprises a 2'-O-methoxyethyl group.

In certain embodiments, at least one nucleoside of the modified oligonucleotide comprises a modified nucleobase. In certain embodiments, the modified nucleobase is a 5'-methylcytosine.

In certain embodiments, at least one nucleoside of the modified oligonucleotide comprises at least one tetrahydropyran modified nucleoside wherein a tetrahydropyran ring replaces the furanose ring. In certain embodiments, each of the at least one tetrahydropyran modified nucleoside has the structure:

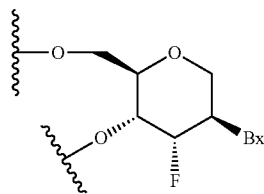

wherein Bx is an optionally protected heterocyclic base moiety.

In certain embodiments, the modified oligonucleotide of the compound comprises:
(i) a gap segment consisting of linked deoxynucleosides;
(ii) a 5' wing segment consisting of linked nucleosides;
(iii) a 3' wing segment consisting of linked nucleosides, wherein the gap segment is positioned immediately adjacent to and between the 5' wing segment and the 3' wing segment and wherein each nucleoside of each wing segment comprises a modified sugar. In some such embodiments, each cytosine in the modified oligonucleotide is a 5-methylcytosine.

In certain embodiments, the modified oligonucleotide of the compound comprises:
(i) a gap segment consisting of ten linked deoxynucleosides;
(ii) a 5' wing segment consisting of five linked nucleosides;
(iii) a 3' wing segment consisting of five linked nucleosides, wherein the gap segment is positioned immediately adjacent to and between the 5' wing segment and the 3' wing segment, wherein each nucleoside of each wing segment comprises a 2'-O-methoxyethyl sugar; and wherein each internucleoside linkage is a phosphorothioate linkage. In some such embodiments, each cytosine in the modified oligonucleotide is a 5-methylcytosine.

Certain embodiments provide the use of Factor 12 specific inhibitors as described herein in the manufacture of a medicament for treating, ameliorating, or preventing an inflammatory condition such as hereditary angioedema.

Certain embodiments provide the use of a Factor 12 specific inhibitor as described herein in the manufacture of a medicament for treating, preventing, or ameliorating an inflammatory condition as described herein in a patient who is subsequently administered an additional agent or therapy as described herein.

Certain embodiments provide a kit for treating, preventing, or ameliorating an inflammatory condition as described herein wherein the kit comprises:
(i) a Factor 12 specific inhibitor as described herein; and alternatively
(ii) an additional agent or therapy as described herein.

A kit may further include instructions for using the kit to treat, prevent, or ameliorate an inflammatory condition as described herein by combination therapy as described herein.

In certain embodiments, provided is a compound comprising a modified oligonucleotide. In certain embodiments, the compound comprises a modified oligonucleotide consisting of 12 to 30 linked nucleosides.

In certain embodiments, the modified oligonucleotide targets a Factor 12 nucleic acid. In certain embodiments, the Factor 12 nucleic acid may be selected from, but is not limited to, one or more of GENBANK Accession No. NM_000505.3 (incorporated herein as SEQ ID NO: 1), GENBANK Accession No. CR601747.1 (incorporated herein as SEQ ID NO: 2), GENBANK Accession No. CR616520.1 (incorporated herein as SEQ ID NO: 3), GENBANK Accession No. CN298799.1 (incorporated herein as SEQ ID NO: 4), GENBANK Accession No. BG248482.1 (incorporated herein as SEQ ID NO: 5), GENBANK Accession No. AW237759.1 (incorporated herein as SEQ ID NO: 6), GENBANK Accession No. BF529177.1 (incorporated herein as SEQ ID NO: 7), the complement of GENBANK Accession No. NT_023133.13 truncated from nucleobase 21637001 to 21650000 (incorporated herein as SEQ ID NO: 8), GENBANK Accession No. CA456551.1 (incorporated herein as SEQ ID NO: 9), GENBANK Accession No. BC057921.1 (incorporated herein as SEQ ID NO: 10), GENBANK Accession No. NM_021489.2 (incorporated herein as SEQ ID NO: 11), GENBANK Accession No. AA277143.1 (incorporated herein as SEQ ID NO: 12), GENBANK Accession No. BI554497.1 (incorporated herein as SEQ ID NO: 13), the complement of GENBANK Accession No. NT_039589.7 truncated from nucleobase 1059000 to nucleobase 1071000

(incorporated herein as SEQ ID NO: 14), GENBANK Accession No. NM_001014006.1 (incorporated herein as SEQ ID NO: 15), the complement of GENBANK Accession No. NW_047487.1 truncated from nucleobase 9759001 to 9773000 (incorporated herein as SEQ ID NO: 16), the complement of GENBANK Accession No. NW_001121001.1 truncated from nucleobase 212000 to 223000 (incorporated herein as SEQ ID NO: 17), GENBANK Accession No. 3378_064_A (incorporated herein as SEQ ID NO: 18), GENBANK Accession No. 3436_025_A (incorporated herein as SEQ ID NO: 19), and GENBANK Accession No. AB179224.1 (incorporated herein as SEQ ID NO: 20).

In certain embodiments, the compound may comprise a modified oligonucleotide comprising a nucleobase sequence at least 80%, at least 85%, at least 90%, at least 95%, at least 96%, at least 97%, at least 98%, or at least 99% complementary to an equal length portion of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, or SEQ ID NO: 20.

In certain embodiments, the compound may comprise a modified oligonucleotide comprising a nucleobase sequence at least 80%, at least 85%, at least 90%, at least 95%, at least 96%, at least 97%, at least 98%, or at least 99% complementary to an equal length portion of a human sequence. In certain embodiments, the compound may comprise a modified oligonucleotide comprising a nucleobase sequence at least 80%, at least 85%, at least 90%, at least 95%, at least 96%, at least 97%, at least 98%, or at least 99% complementary to an equal length portion of SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8.

In certain embodiments, the compound may comprise a modified oligonucleotide comprising a nucleobase sequence 100% complementary to an equal length portion of SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8.

In certain embodiments, the compound may comprise a modified oligonucleotide comprising a nucleobase sequence 100% complementary to an equal length portion of a human sequence. In certain embodiments, the compound may comprise a modified oligonucleotide comprising a nucleobase sequence 100% complementary to an equal length portion of SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8.

In certain embodiments, the nucleobase sequence of the modified oligonucleotide is 100% complementary to a nucleobase sequence of SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8.

Certain embodiments provide a method comprising, (1) identifying an animal at risk for experiencing an attack of hereditary angioedema; and (2) prophylactically administering to the at risk animal a therapeutically effective amount of a modified oligonucleotide consisting of 12 to 30 linked nucleosides, wherein the modified oligonucleotide is at least 90% complementary to a Facter 12 nucleic acid.

Certain embodiments provide a method comprising, (1) identifying an animal at risk for developing an inflammatory condition; and (2) prophylactically administering to the at risk animal a therapeutically effective amount of a modified oligonucleotide consisting of 12 to 30 linked nucleosides, wherein the modified oligonucleotide is at least 90% complementary to a Facter 12 nucleic acid.

In certain embodiments, expression of Factor 12 mRNA is reduced.

In certain embodiments, expression of Factor 12 protein is reduced.

In certain embodiments, the inflammatory condition is an acute inflammatory condition.

In certain embodiments, the acute inflammatory condition is hereditary angioedema.

In certain embodiments, the prophylactic administering of a modified oligonucleotide prevents edema.

In certain embodiments, the prophylactic administering of a modified oligonucleotide prevents vascular permeability.

In certain embodiments, the prophylactic administering of a modified oligonucleotide prevents vascular leakage.

In certain embodiments, the prophylactic administering of a modified oligonucleotide prevents inflammation.

Certain embodiments provide a method comprising prophylactically treating an inflammatory condition in an animal by administering to the animal a therapeutically effective amount of a modified oligonucleotide consisting of 12 to 30 linked nucleosides, wherein the modified oligonucleotide is at least 90% complementary to a Factor 12 nucleic acid.

In certain embodiments, the inflammatory condition is an acute inflammatory condition.

In certain embodiments, the acute inflammatory condition is hereditary angioedema.

Certain embodiments provide a method comprising inhibiting edmea in an animal by administering to the animal a therapeutically effective amount of a modified oligonucleotide consisting of 12 to 30 linked nucleosides, wherein the modified oligonucleotide is at least 90% complementary to a Factor 12 nucleic acid.

Certain embodiments provide a method comprising inhibiting vascular permeability in an animal by administering to the animal a therapeutically effective amount of a modified oligonucleotide consisting of 12 to 30 linked nucleosides, wherein the modified oligonucleotide is at least 90% complementary to a Factor 12 nucleic acid.

Certain embodiments provide a method comprising inhibiting vascular leakage in an animal by administering to the animal a therapeutically effective amount of a modified oligonucleotide consisting of 12 to 30 linked nucleosides, wherein the modified oligonucleotide is at least 90% complementary to a Factor 12 nucleic acid.

Certain embodiments provide a method comprising inhibiting inflammation in an animal by administering to the animal a therapeutically effective amount of a modified oligonucleotide consisting of 12 to 30 linked nucleosides, wherein the modified oligonucleotide is at least 90% complementary to a Factor 12 nucleic acid.

In certain embodiments, the animal is a human.

In certain embodiments, the Factor 12 nucleic acid is a human Factor 12 nucleic acid.

In certain embodiments, the human Factor 12 nucleic acid is SEQ ID NO: 1, SEQ ID NO: 2, SEQ ID NO: 3, SEQ ID NO: 4, SEQ ID NO: 5, SEQ ID NO: 6, SEQ ID NO: 7, or the complement of SEQ ID NO: 8.

In certain embodiments, the modified oligonucleotide is 100% complementary to a human Factor 12 nucleic acid.

In certain embodiments, the modified oligonucleotide is a single-stranded oligonucleotide.

In certain embodiments, wherein the modified oligonucleotide comprises at least one modified internucleoside linkage.

In certain embodiments, the modified internucleoside linkage is a phosphorothioate internucleoside linkage.

In certain embodiments, the modified oligonucleotide comprises at least one nucleoside having a modified sugar.

In certain embodiments, the modified sugar is a bicyclic sugar.

In certain embodiments, the bicyclic sugar comprises a 4'-CH(CH₃)—O-2' bridge.

In certain embodiments, the modified oligonucleotide comprises at least one tetrahydropyran modified nucleoside wherein a tetrahydropyran ring replaces the furanose ring.

In certain embodiments, each of the at least one tetrahydropyran modified nucleoside has the structure:

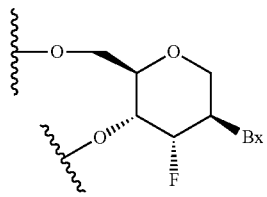

wherein Bx is an optionally protected heterocyclic base moiety.

In certain embodiments, the modified sugar comprises a 2'-O-methoxyethyl group.

In certain embodiments, at least one nucleoside comprises a modified nucleobase.

In certain embodiments, the modified nucleobase is a 5-methylcytosine.

In certain embodiments, the modified oligonucleotide is co-administered with any of the group selected from a serine protease inhibitor C1-INH recombinant protein, kallikrein antisense oligonucleotide, CINRYZE, BERINERT, KALBITOR, Icatibant, Ecallantide, attenuated androgens, anabolic steroids, and antifibrinolytic agents (e.g., epsilon-aminocaproic acid and tranexamic acid).

Certain embodiments provide, a modified oligonucleotide consisting of 12 to 30 linked nucleosides fully complementary to SEQ ID NO: 1, SEQ ID NO: 2, SEQ ID NO: 3, SEQ ID NO: 4, SEQ ID NO: 5, SEQ ID NO: 6, SEQ ID NO: 7, or the complement of SEQ ID NO: 8 for use in the treatment of an inflammatory condition.

In certain embodiments, the inflammatory condition is hereditary angioedema.

Certain embodiments provide use of a modified oligonucleotide as described herein in the manufacture of a medicament for treating an inflammatory condition.

In certain embodiments, the administering is parenteral administration. In certain embodiments, the parenteral administration is any of subcutaneous or intravenous administration.

Certain embodiments provide a method comprising, increasing or stabilizing HMWK in an animal in need thereof by administering to the animal a therapeutically effective amount of a modified oligonucleotide consisting of 12 to 30 linked nucleosides, wherein the modified oligonucleotide is at least 90% complementary to a Factor 12 nucleic acid.

Certain embodiments provide a method of treating an inflammatory condition in an animal in need thereof by increasing or stabilizing HMWK in the animal by administering to the animal a therapeutically effective amount of a modified oligonucleotide consisting of 12 to 30 linked nucleosides, wherein the modified oligonucleotide is at least 90% complementary to a Factor 12 nucleic acid.

In certain embodiments, the inflammatory condition is associated with low levels of HMWK.

In certain embodiments, the inflammatory condition is associated with high levels of bradykinin.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a Factor 12 nucleic acid is 12 to 30 subunits in length. In other words, such antisense compounds are from 12 to 30 linked subunits. In other embodiments, the antisense compound is 8 to 80, 12 to 50, 15 to 30, 18 to 24, 19 to 22, or linked subunits. In certain such embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleosides.

In certain embodiments antisense oligonucleotides targeted to a Factor 12 nucleic acid may be shortened or truncated. For example, a single subunit may be deleted from the 5' end (5' truncation), or alternatively from the 3' end (3' truncation). A shortened or truncated antisense compound targeted to a Factor 12 nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a Factor 12 nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—CH$_3$, among others), and bicyclic sugar modified nucleosides (such bicyclic sugar modified nucleosides may include those having a 4'-(CH2)n-O-2' bridge, where n=1 or n=2). Preferably, each distinct region comprises uniform sugar moieties. The wing-gap-wing motif is frequently described as "X-Y-Z", where "X" represents the length of the 5' wing region, "Y" represents the length of the gap region, and "Z" represents the length of the 3' wing region. As used herein, a gapmer described as "X-Y-Z" has a configuration such that the gap segment is positioned immediately adjacent to each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same, in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 25, 30 or more nucleotides. Thus, gapmers of the present invention include, but are not limited to, for example 5-10-5, 4-8-4, 4-12-3, 4-12-4, 3-14-3, 2-13-5, 2-16-2, 1-18-1, 3-10-3, 2-10-2, 1-10-1, 2-8-2, 5-8-5, or 6-8-6.

In certain embodiments, the antisense compound has a "wingmer" motif, having a wing-gap or gap-wing configuration, i.e. an X-Y or Y-Z configuration as described above for the gapmer configuration. Thus, wingmer configurations of the present invention include, but are not limited to, for example 5-10, 8-4, 4-12, 12-4, 3-14, 16-2, 18-1, 10-3, 2-10, 1-10, 8-2, 2-13, 5-13, 5-8, or 6-8.

In certain embodiments, antisense compounds targeted to a Factor 12 nucleic acid possess a 5-10-5 gapmer motif.

In certain embodiments, antisense compounds targeted to a Factor 12 nucleic acid possess a 3-14-3 gapmer motif.

In certain embodiments, antisense compounds targeted to a Factor 12 nucleic acid possess a 2-13-5 gapmer motif.

In certain embodiments, antisense compounds targeted to a Factor 12 nucleic acid possess a 5-8-5 gapmer motif.

In certain embodiments, antisense compounds targeted to a Factor 12 nucleic acid possess a 6-8-6 gapmer motif.

In certain embodiments, an antisense compound targeted to a Factor 12 nucleic acid has a gap-widened motif.

In certain embodiments, a gap-widened antisense oligonucleotide targeted to a Factor 12 nucleic acid has a gap segment of fourteen 2'-deoxyribonucleotides positioned immediately adjacent to and between wing segments of three chemically modified nucleosides. In certain embodiments, the chemical modification comprises a 2'-sugar modification. In another embodiment, the chemical modification comprises a 2'-MOE sugar modification.

In certain embodiments, a gap-widened antisense oligonucleotide targeted to a Factor 12 nucleic acid has a gap segment of thirteen 2'-deoxyribonucleotides positioned immediately adjacent to and between a 5' wing segment of two chemically modified nucleosides and a 3' wing segment of five chemically modified nucleosides. In certain embodiments, the chemical modification comprises a 2'-sugar modification. In another embodiment, the chemical modification comprises a 2'-MOE sugar modification.

Target Nucleic Acids, Target Regions and Nucleotide Sequences

Nucleotide sequences that encode Factor 12 include, without limitation, the following: GENBANK Accession No. NM_000505.3 (incorporated herein as SEQ ID NO: 1), GENBANK Accession No. CR601747.1 (incorporated herein as SEQ ID NO: 2), GENBANK Accession No. CR616520.1 (incorporated herein as SEQ ID NO: 3), GENBANK Accession No. CN298799.1 (incorporated herein as SEQ ID NO: 4), GENBANK Accession No. BG248482.1 (incorporated herein as SEQ ID NO: 5), GENBANK Accession No. AW237759.1 (incorporated herein as SEQ ID NO: 6), GENBANK Accession No. BF529177.1 (incorporated herein as SEQ ID NO: 7), the complement of GENBANK Accession No. NT_023133.13 truncated from nucleobase 21637001 to 21650000 (incorporated herein as SEQ ID NO: 8), GENBANK Accession No. CA456551.1 (incorporated herein as SEQ ID NO: 9), GENBANK Accession No. BC057921.1 (incorporated herein as SEQ ID NO: 10), GENBANK Accession No. NM_021489.2 (incorporated herein as SEQ ID NO: 11), GENBANK Accession No. AA277143.1 (incorporated herein as SEQ ID NO: 12), GENBANK Accession No. BI554497.1 (incorporated herein as SEQ ID NO: 13), the complement of GENBANK Accession No. NT_039589.7 truncated from nucleobase 1059000 to nucleobase 1071000 (incorporated herein as SEQ ID NO: 14), GENBANK Accession No. NM_001014006.1 (incorporated herein as SEQ ID NO: 15), the complement of GEN-BANK Accession No. NW_047487.1 truncated from nucleobase 9759001 to 9773000 (incorporated herein as SEQ ID NO: 16), the complement of GENBANK Accession No. NW_001121001.1 truncated from nucleobase 212000 to 223000 (incorporated herein as SEQ ID NO: 17), GEN-BANK Accession No. 3378_064_A (incorporated herein as SEQ ID NO: 18), GENBANK Accession No. 3436_025_A (incorporated herein as SEQ ID NO: 19), and GENBANK Accession No. AB179224.1 (incorporated herein as SEQ ID NO: 20).

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for Factor 12 can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in Factor 12 mRNA levels are indicative of inhibition of Factor 12 expression. Reductions in levels of a Factor 12 protein are also indicative of inhibition of target mRNA expression. Further, phenotypic changes are indicative of inhibition of Factor 12 expression. For example, reduced or prevented inflammation can be indicative of inhibition of Factor 12 expression. In another example, reduced or prevented edema/swelling can be indicative of inhibition of Factor 12 expression. In another example, prolonged clotting times (aPTT) can be indicative of inhibition of Factor 12. In another example, reduced or prevented vascular permeability can be indicative of inhibition of Factor 12 expression. In another example, reduced or prevented vascular leakage can be indicative of inhibition of Factor 12 expression. In certain embodiments, vascular permeability is measured by quanification of a dye, such as Evans Blue.

Hybridization

In some embodiments, hybridization occurs between an antisense compound disclosed herein and a Factor 12 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a Factor 12 nucleic acid.

Complementarily

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a Factor 12 nucleic acid).

Non-complementary nucleobases between an antisense compound and a Factor 12 nucleic acid may be tolerated provided that the antisense compound remains able to specifically hybridize to a target nucleic acid. Moreover, an antisense compound may hybridize over one or more segments of a Factor 12 nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a Factor 12 nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e., 100% complementary) to a target nucleic acid, or specified portion thereof. For example, an antisense compound may be fully complementary to a Factor 12 nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and for the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e., linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a Factor 12 nucleic acid, or specified portion thereof.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a Factor 12 nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 12 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a Factor 12 nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-$OCH_3$, 2'-$OCH_2CH_3$, 2'-$OCH_2CH_2F$ and 2'-$O(CH_2)_2OCH_3$ substituent groups. The substituent at the 2' position can also be selected from allyl, amino, azido, thio, O-allyl, O—$C_1$-$C_{10}$ alkyl, $OCF_3$, $OCH_2F$, $O(CH_2)_2SCH_3$, $O(CH_2)_2$—O—$N(R_m)(R_n)$, O—$CH_2$—C(=O)—$N(R_m)(R_n)$, and O—$CH_2$—C(=O)—$N(R_l)$—$(CH_2)_2$—$N(R_m)(R_n)$, where each $R_l$, $R_m$, and $R_n$ is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleosides include without limitation nucleosides comprising a bridge between the 4' and the 2' ribosyl ring atoms. In certain embodiments, antisense compounds provided herein include one or more bicyclic nucleosides comprising a 4' to 2' bridge. Examples of such 4' to 2' bridged bicyclic nucleosides, include but are not limited to one of the formulae: 4'-($CH_2$)—O-2' (LNA); 4'-($CH_2$)—S-2'; 4'-($CH_2$)$_2$—O-2' (ENA); 4'-CH($CH_3$)—O-2' and 4'-CH($CH_2OCH_3$)—O-2' (and analogs thereof see U.S. Pat. No. 7,399,845, issued on Jul. 15, 2008); 4'-C($CH_3$)($CH_3$)—O-2' (and analogs thereof see published International Application WO/2009/006478, published Jan. 8, 2009); 4'-$CH_2$—N($OCH_3$)-2' (and analogs thereof see published International Application WO/2008/150729, published Dec. 11, 2008); 4'-$CH_2$—O—N($CH_3$)-2' (see published U.S. Patent Application US2004-0171570, published Sep. 2, 2004); 4'-$CH_2$—N(R)—O-2', wherein R is H, $C_1$-$C_{12}$ alkyl, or a protecting group (see U.S. Pat. No. 7,427,672, issued on Sep. 23, 2008); 4'-$CH_2$—C(H)($CH_3$)-2' (see Chattopadhyaya et al., *J. Org. Chem.*, 2009, 74, 118-134); and 4'-$CH_2$—C—(=$CH_2$)-2' (and analogs thereof see published International Application WO 2008/154401, published on Dec. 8, 2008).

Further reports related to bicyclic nucleosides can also be found in published literature (see for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 2007, 129(26) 8362-8379; Elayadi et al., *Curr. Opinion Invest. Drugs*, 2001, 2, 558-561; Braasch et al., *Chem. Biol.*, 2001, 8, 1-7; and Orum et al., *Curr. Opinion Mol. Ther.*, 2001, 3, 239-243; U.S. Pat. Nos. 6,268,490; 6,525,191; 6,670,461; 6,770,748; 6,794,499; 7,034,133; 7,053,207; 7,399,845; 7,547,684; and 7,696,345; U.S. Patent Publication No. US2008-0039618; US2009-0012281; U.S. Patent Ser. Nos. 60/989,574; 61/026,995; 61/026,998; 61/056,564; 61/086,231; 61/097,787; and 61/099,844; Published PCT International applications WO 1994/014226; WO 2004/106356; WO 2005/021570; WO 2007/134181; WO 2008/150729; WO 2008/154401; and WO 2009/006478. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —[C($R_a$)($R_b$)]$_n$—, —C($R_a$)=C($R_b$)—, —C($R_a$)=N—, —C(=O)—, —C(=$NR_a$)—, —C(=S)—, —O—, —Si($R_a$)$_2$—, —S(=O)$_x$—, and —N($R_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is —[C($R_a R_b$)]$_n$—, —[C($R_a$)($R_b$)]$_n$—O—, —C($R_a R_b$)—N(R)—O— or —C($R_a R_b$)—O—N(R)—. In certain embodiments, the bridge is 4'-CH$_2$-2',4'-(CH$_2$)$_2$-2',4'-(CH$_2$)$_3$-2',4'-(CH$_2$)$_2$—O-2',4'-CH$_2$—O—N(R)-2' and 4'-CH$_2$—N(R)—O-2'- wherein each R is, independently, H, a protecting group or $C_1$-$C_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include, but are not limited to, (A) α-L-methyleneoxy (4'-CH$_2$—O-2') BNA, (B) β-D-methyleneoxy (4'-CH$_2$—O-2') BNA, (C) ethyleneoxy (4'-(CH$_2$)$_2$—O-2') BNA, (D) aminooxy (4'-CH$_2$—O—N(R)-2') BNA, (E) oxyamino (4'-CH$_2$—N(R)—O-2') BNA, and (F) methyl(methyleneoxy) (4'-CH(CH$_3$)—O-2') BNA, (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, and (J) propylene carbocyclic (4'-(CH$_2$)$_3$-2') BNA as depicted below.

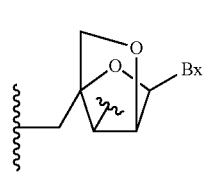

(A)

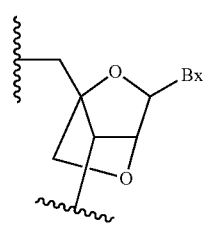

(B)

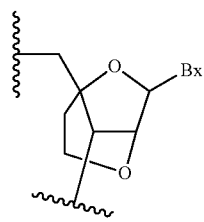

(C)

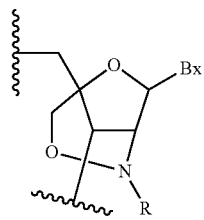

(D)

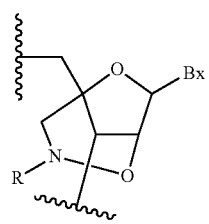

(E)

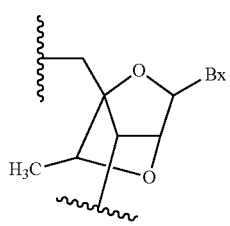

(F)

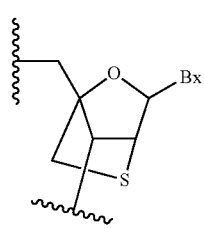

(G)

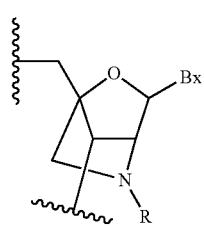

(H)

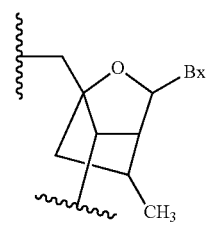

(I)

-continued

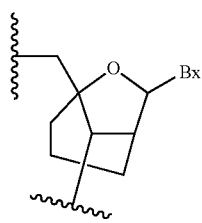

(J)

wherein Bx is the base moiety and R is independently H, a protecting group or $C_1$-$C_{12}$ alkyl.

In certain embodiments, bicyclic nucleosides are provided having Formula I:

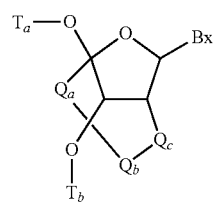

I wherein:

Bx is a heterocyclic base moiety;

-$Q_a$-$Q_b$-$Q_c$- is —$CH_2$—N($R_c$)—$CH_2$—, —C(=O)—N($R_c$)—$CH_2$—, —$CH_2$—O—N($R_c$)—, —$CH_2$—N($R_c$)—O— or —N($R_c$)—O—$CH_2$;

$R_c$ is $C_1$-$C_{12}$ alkyl or an amino protecting group; and $T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides are provided having Formula II:

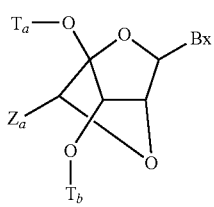

II wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, OC(=X)$J_c$, and $NJ_eC(=X)NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides are provided having Formula III:

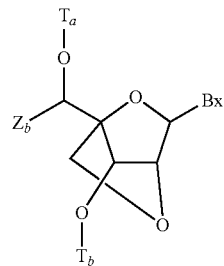

III wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides are provided having Formula IV:

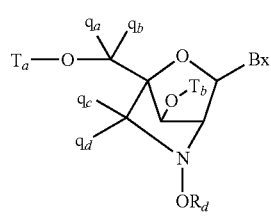

IV wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides are provided having Formula V:

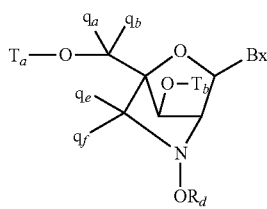

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SOJ_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$;

or $q_e$ and $q_f$ together are =C($q_g$)($q_h$);

$q_g$ and $q_h$ are each, independently, H, halogen, $C_1$-$C_{12}$ alkyl or substituted $C_1$-$C_{12}$ alkyl.

The synthesis and preparation of the methyleneoxy (4'-$CH_2$—O-2') BNA monomers adenine, cytosine, guanine, 5-methyl-cytosine, thymine and uracil, along with their oligomerization, and nucleic acid recognition properties have been described (Koshkin et al., *Tetrahedron*, 1998, 54, 3607-3630). BNAs and preparation thereof are also described in WO 98/39352 and WO 99/14226.

Analogs of methyleneoxy (4'-$CH_2$—O-2') BNA and 2'-thio-BNAs, have also been prepared (Kumar et al., *Bioorg. Med. Chem. Lett.*, 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel comformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides are provided having Formula VI:

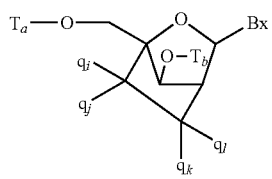

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SOJ_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-($CH_2$)$_3$-2' bridge and the alkenyl analog bridge 4'-CH=CH—$CH_2$-2' have been described (Freier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.*, 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: O[($CH_2$)$_n$O]$_m$$CH_3$, O($CH_2$)$_n$$NH_2$, O($CH_2$)$_n$$CH_3$, O($CH_2$)$_n$F, O($CH_2$)$_n$$ONH_2$, $OCH_2$C(=O)N(H)$CH_3$, and O($CH_2$)$_n$ON[($CH_2$)$_n$$CH_3$]$_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, $SCH_3$, OCN, Cl, Br, CN, F, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., *J. Biol. Chem.*, 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.*, 2002, 10, 841-854), fluoro HNA (F-HNA) or those compounds having Formula VII:

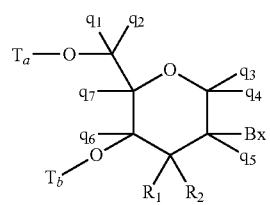

VII wherein independently for each of said at least one tetrahydropyran nucleoside analog of Formula VII:

Bx is a heterocyclic base moiety;

$T_a$ and $T_b$ are each, independently, an internucleoside linking group linking the tetrahydropyran nucleoside analog to the antisense compound or one of $T_a$ and $T_b$ is an internucleoside linking group linking the tetrahydropyran nucleoside analog to the antisense compound and the other of $T_a$ and $T_b$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and each of $R_1$ and $R_2$ is selected from hydrogen, hydroxyl, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is fluoro. In certain embodiments, $R_1$ is fluoro and $R_2$ is H; $R_1$ is methoxy and $R_2$ is H, and $R_1$ is H and $R_2$ is methoxyethoxy.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2' substituents, such as allyl, amino, azido, thio, O-allyl, O—$C_1$-$C_{10}$ alkyl, —$OCF_3$, O—$(CH_2)_2$—O—$CH_3$, 2'-O$(CH_2)_2SCH_3$, O—$(CH_2)_2$—O—N$(R_m)(R_n)$, or O—$CH_2$—C(=O)—N$(R_m)(R_n)$, where each $R_m$ and $R_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position.

As used herein, "2'-OMe" or "2'-$OCH_3$" or "2'-O-methyl" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see for example review article: Leumann, *Bioorg. Med. Chem.*, 2002, 10, 841-854).

Such ring systems can undergo various additional substitutions to enhance activity.

Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-$CH(CH_3)$—O-2') bridging group. In certain embodiments, the (4'-$CH(CH_3)$—O-2') modified nucleosides are arranged throughout the wings of a gapmer motif.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to a Factor 12 nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a Factor 12 nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of Factor 12 nucleic acids can be tested in vitro in a variety of cell types. Cell types used for such analyses are available from commercial vendors (e.g. American Type Culture Collection, Manassus, Va.; Zen-Bio, Inc., Research Triangle Park, N.C.; Clonetics Corporation, Walkersville, Md.) and are cultured according to the vendor's instructions using commercially available reagents (e.g. Invitrogen Life Technologies, Carlsbad, Calif.). Illustrative cell types include, but are not limited to, HepG2 cells, Hep3B cells, and primary hepatocytes.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, Calif.). Antisense oligonucleotides are mixed with LIPOFECTIN in OPTI-MEM 1 (Invitrogen, Carlsbad, Calif.) to achieve the desired final concentration of antisense oligonucleotide and a LIPOFECTIN concentration that typically ranges 2 to 12 ug/mL per 100 nM antisense oligonucleotide.

Another reagent used to introduce antisense oligonucleotides into cultured cells includes LIPOFECTAMINE (Invitrogen, Carlsbad, Calif.). Antisense oligonucleotide is mixed with LIPOFECTAMINE in OPTI-MEM 1 reduced serum medium (Invitrogen, Carlsbad, Calif.) to achieve the desired concentration of antisense oligonucleotide and a LIPOFECTAMINE concentration that typically ranges 2 to 12 ug/mL per 100 nM antisense oligonucleotide.

Another technique used to introduce antisense oligonucleotides into cultured cells includes electroporation.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL Reagent (Invitrogen, Carlsbad, Calif.) according to the manufacturer's recommended protocols.

Analysis of Inhibition of Target Levels or Expression

Inhibition of levels or expression of a Factor 12 nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN (Invitrogen, Inc. Carlsbad, Calif.). Cyclophilin A expression is quantified by real time PCR, by being run simultaneously with the target, multiplexing, or separately. Total RNA is quantified using RIBOGREEN RNA quantification reagent (Invetrogen, Inc. Eugene, Oreg.). Methods of RNA quantification by RIBOGREEN are taught in Jones, L. J., et al, (Analytical Biochemistry, 1998, 265, 368-374). A CYTOFLUOR 4000 instrument (PE Applied Biosystems) is used to measure RIBOGREEN fluorescence.

Probes and primers are designed to hybridize to a Factor 12 nucleic acid. Methods for designing real-time PCR probes and primers are well known in the art, and may include the use of software such as PRIMER EXPRESS Software (Applied Biosystems, Foster City, Calif.).

Analysis of Protein Levels

Antisense inhibition of Factor 12 nucleic acids can be assessed by measuring Factor 12 protein levels. Protein levels of Factor 12 can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of mouse, rat, monkey, and human Factor 12 are commercially available.

In Vivo Testing of Antisense Compounds

Antisense compounds, for example, antisense oligonucleotides, are tested in animals to assess their ability to inhibit expression of Factor 12 and produce phenotypic changes, such as, reduced inflammation, edema/swelling, vascular permeability, and vascular leakage. In certain embodiments, inflammation is measured by measuring the increase or decrease of edema, temperature, pain, color of tissue, and abdominal function in the animal. Testing may be performed in normal animals, or in experimental disease models. For administration to animals, antisense oligonucleotides are formulated in a pharmaceutically acceptable diluent, such as phosphate-buffered saline. Administration includes parenteral routes of administration, such as intraperitoneal, intravenous, and subcutaneous. Calculation of antisense oligonucleotide dosage and dosing frequency is within the abilities of those skilled in the art, and depends upon factors such as route of administration and animal body weight. Following a period of treatment with antisense oligonucleotides, RNA is isolated from liver tissue and changes in Factor 12 nucleic acid expression are measured.

Certain Indications

In certain embodiments, the invention provides methods of treating an individual comprising administering one or more pharmaceutical compositions of the present invention. In certain embodiments, the individual has an inflammatory condition. In certain embodiments, the individual is at risk for developing an inflammatory condition, including, but not limited to, hereditary angioedema (HAE), edema, angioedema, swelling, angioedema of the lids, ocular edema, macular edema, and cerebral edema. This includes individuals with an acquired problem, disease, or disorder that leads to a risk of inflammation, for example, genetic predisposition to an inflammatory condition, environmental factors, and exposure to certain medications, including, for example, ACE inhibitors and ARBs. In certain embodiments, the individual has been identified as in need of anti-inflammation therapy. Examples of such individuals include, but are not limited to those having a mutation in the genetic code for complement 1 esterase inhibitor (i.e., C1-INH) or Factor 12. In certain embodiments, an abnormal code can lead to a deficiency in C1-INH (i.e., type I HAE), an inability of existing C1-INH to function properly (type II HAE), or hyperfunctional Factor 12 (i.e., type III HAE). In certain embodiments the invention provides methods for prophylactically reducing Factor 12 expression in an individual. Certain embodiments include treating an individual in need thereof by administering to an individual a therapeutically effective amount of an antisense compound targeted to a Factor 12 nucleic acid.

In one embodiment, administration of a therapeutically effective amount of an antisense compound targeted to a Factor 12 nucleic acid is accompanied by monitoring of Factor 12 levels in the serum of an individual, to determine an individual's response to administration of the antisense compound. An individual's response to administration of the antisense compound is used by a physician to determine the amount and duration of therapeutic intervention.

In certain embodiments, administration of an antisense compound targeted to a Factor 12 nucleic acid results in reduction of Factor 12 expression by at least 15, 20, 25, 30, 35, 40, 45, 50, 55, 60, 65, 70, 75, 80, 85, 90, 95 or 99%, or a range defined by any two of these values. In certain embodiments, administration of an antisense compound targeted to a Factor 12 nucleic acid results in a change in a measure of inflammation, swelling, hypertension, and/or vascular permeability. In certain embodiments, administration of a Factor 12 antisense compound increases the measure by at least 15, 20, 25, 30, 35, 40, 45, 50, 55, 60, 65, 70, 75, 80, 85, 90, 95 or 99%, or a range defined by any two of these values. In some embodiments, administration of a Factor 12 antisense compound decreases the measure by at least 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to Factor 12 are used for the preparation of a medicament for treating a patient suffering or susceptible to an inflammatory condition including hereditary angioedema (HAE).

Certain Combination Therapies

In certain embodiments, one or more pharmaceutical compositions of the present invention are co-administered with one or more other pharmaceutical agents. In certain embodiments, such one or more other pharmaceutical agents are designed to treat the same disease, disorder, or condition as the one or more pharmaceutical compositions of the present invention. In certain embodiments, such one or more other pharmaceutical agents are designed to treat a different disease, disorder, or condition as the one or more pharmaceutical compositions of the present invention. In certain embodiments, such one or more other pharmaceutical agents are designed to treat an undesired side effect of one or more pharmaceutical compositions of the present invention. In certain embodiments, one or more pharmaceutical compositions of the present invention are co-administered with another pharmaceutical agent to treat an undesired effect of that other pharmaceutical agent. In certain embodiments, one or more pharmaceutical compositions of the present invention are co-administered with another pharmaceutical agent to produce a combinational effect. In certain embodiments, one or more pharmaceutical compositions of the present invention are co-administered with another pharmaceutical agent to produce a synergistic effect.

In certain embodiments, one or more pharmaceutical compositions of the present invention and one or more other pharmaceutical agents are administered at the same time. In certain embodiments, one or more pharmaceutical compositions of the present invention and one or more other pharmaceutical agents are administered at different times. In certain embodiments, one or more pharmaceutical compositions of the present invention and one or more other pharmaceutical agents are prepared together in a single formulation. In certain embodiments, one or more pharmaceutical compositions of the present invention and one or more other pharmaceutical agents are prepared separately.

In certain embodiments, pharmaceutical agents that may be co-administered with a pharmaceutical composition of the present invention include anticoagulant or antiplatelet agents. In certain embodiments, pharmaceutical agents that may be co-administered with a pharmaceutical composition of the present invention include serine protease inhibitor C1-INH recombinant protein, kallikrein antisense oligonucleotide, CINRYZE, BERINERT, KALBITOR, Icatibant, Ecallantide, attenuated androgens, anabolic steroids, and antifibrinolytic agents (e.g., epsilon-aminocaproic acid and tranexamic acid).

In certain embodiments, pharmaceutical agents that may be co-administered with a Factor 12 specific inhibitor of the present invention include, but are not limited to, an additional Factor 12 inhibitor. In certain embodiments, the co-administered pharmaceutical agent is administered prior to administration of a pharmaceutical composition of the present invention. In certain embodiments, the co-administered pharmaceutical agent is administered following administration of a pharmaceutical composition of the present invention. In certain embodiments the co-administered pharmaceutical agent is administered at the same time as a pharmaceutical composition of the present invention. In certain embodiments the dose of a co-administered pharmaceutical agent is the same as the dose that would be administered if the co-administered pharmaceutical agent was administered alone. In certain embodiments the dose of a co-administered pharmaceutical agent is lower than the dose that would be administered if the co-administered pharmaceutical agent was administered alone. In certain embodiments the dose of a co-administered pharmaceutical agent is greater than the dose that would be administered if the co-administered pharmaceutical agent was administered alone.

In certain embodiments, the co-administration of a second compound enhances the anti-inflammatory effect of a first compound, such that co-administration of the compounds results in an anti-inflammatory effect that is greater than the effect of administering the first compound alone. In other embodiments, the co-administration results in anti-inflammatory effects that are additive of the effects of the compounds when administered alone. In certain embodiments, the co-administration results in anti-inflammatory effects that are supra-additive of the effects of the compounds when administered alone. In certain embodiments, the first compound is an antisense compound. In certain embodiments, the second compound is an antisense compound.

EXAMPLES

Non-Limiting Disclosure and Incorporation by Reference

While certain compounds, compositions, and methods described herein have been described with specificity in accordance with certain embodiments, the following examples serve only to illustrate the compounds described herein and are not intended to limit the same. Each of the references recited in the present application is incorporated herein by reference in its entirety.

Example 1

Antisense Inhibition of Murine Factor 12 mRNA

Antisense oligonucleotides targeted to a murine Factor 12 nucleic acid were tested for their effects on Factor 12 mRNA in vitro. Cultured mouse primary hepatocytes at a density of 10,000 cells per well were transfected using Cytofectin reagent with 100 nM antisense oligonucleotide. After a treatment period of approximately 24 hours, RNA was isolated from the cells and mouse Factor 12 mRNA levels were measured by quantitative real-time PCR using the murine primer probe set RTS2959 (forward sequence CAAAGGAGGGACATGTATCAACAC, designated herein as SEQ ID NO: 22; reverse sequence CTGGCAATGTTTCCCAGTGA, designated herein as SEQ ID NO: 23; probe sequence CCCAATGGGCCACACTGTCTCTGC, designated herein as SEQ ID NO: 24). Factor 12 mRNA levels were adjusted according to total RNA content, as measured by RIBOGREEN.

ISIS 410944 (SEQ ID NO: 36), which was one of the antisense oligonucleotides tested in the assay, was designed as a 5-10-5 MOE gapmer, and is 20 nucleosides in length, wherein the central gap segment is comprised of ten 2'-deoxynucleosides and is flanked on both sides (in the 5' and 3' directions) by wings comprising 5 nucleosides each. Each nucleoside in the 5' wing segment and each nucleoside in the 3' wing segment has a 2'-MOE modification. The internucleoside linkages throughout the gapmer are phosphorothioate (P=S) linkages. All cytosine residues throughout the gapmer are 5-methylcytosines. ISIS 410944 is targeted to nucleobases 980 to 999 of mouse Factor 12 mRNA (GENBANK Accession No. NM_021489.2), incorporated herein as SEQ ID NO: 11. ISIS 410944 inhibited murine Factor 12 mRNA by 68%.

C57BL/6J-Tyrc-2J mice were treated with 2.5 mg/kg, 5 mg/kg, 10 mg/kg, 20 mg/kg, 40 mg/kg, or 80 mg/kg (corresponding to 5 mg/kg, 10 mg/kg, 20 mg/kg, 40 mg/kg, 80 mg/kg, or 160 mg/kg per week) of ISIS 410944 administered subcutaneously twice a week for 3 weeks. Factor 12 mRNA and protein expression was reduced in a dose dependent manner. Factor 12 mRNA was reduced by greater than 90% inhibition at a dose of 160 mg/kg per week.

Example 2

In Vivo Effect of Antisense Inhibition of Murine Factor 12 in an Angioedema Mouse Model Hereditary angioedema (HAE) is characterized by local swelling and increase in vascular permeability in subcutaneous tissues (Morgan, B. P. N. Engl. J. Med. 363: 581-83, 2010). It is caused by a deficiency of the C1 inhibitor, a protein of the complement system. Two mouse models were used in this study, including, an established mouse model of C1-INH deficiency and a captopril-induced edema model, both of which cause vascular permeability, a hallmark of HAE. Reversal of vascular permeability is accompanied by increased plasma levels of high molecular weight kininogen (HMWK).

In the first model, angioedema was induced by treatment with Captopril, a known antihypertensive agent, which increases vascular permeability in mice and replicates the pathology of hereditary angioedema.

In the second model, angioedema was induced by treatment with ISIS 461756, an antisense oligonucleotide which targets murine C1 inhibitor mRNA, which increases vascular permeability in mice and replicates the pathology of hereditary angioedema. ISIS 461756 (SEQ ID NO: 37; AAAGTGGTTGATACCCTGGG) is a 5-10-5 MOE gapmer targeting nucleosides 1730-1749 of NM_009776.3 (SEQ ID NO: 21).

The effect of HOE-140 and ISIS 410944, an antisense oligonucleotide inhibitor of Factor 12, were evaluated in the Captopril and ISIS 461756-induced mouse models of vascular permeability. Some of the murine groups were treated with HOE-140, a selective antagonist of the bradykinin B2 receptor, which blocks vasodilation and vascular permeability (Cruden and Newby, Expert Opin. Pharmacol. 9: 2383-90, 2008). Other mice were treated with ISIS 410944, which inhibits Factor 12 mRNA expression. The effect of treatment with HOE-140 was compared with the effect of treatment with ISIS 410944.

Treatment

The various treatment groups for this assay are presented in Table 1.

Group 1 consisted of 4 C57BL/6J-Tyrc-2J mice treated with PBS administered subcutaneously twice a week for 4 weeks. No other treatment was administered to Group 1, which served as a control group to measure the basal level of vascular permeability.

Group 2 consisted of 8 C57BL/6J-Tyrc-2J mice treated with PBS administered subcutaneously twice a week for 4 weeks. At the end of the treatment, the mice were intraperitoneally administered 20 µg of captopril. Group 2 served as a PBS control group for captopril-induced vascular permeability.

Group 3 consisted of 8 C57BL/6J-Tyrc-2J mice treated with PBS administered subcutaneously twice a week for 4 weeks. On day 14, the mice were treated with 50 mg/kg of the antisense oligonucleotide targeting C1 inhibitor, ISIS 461756, administered subcutaneously twice a week for 2 weeks. At the end of the treatment period, the mice were intraperitoneally administered 20 µg of captopril. Group 3 served as a PBS control group for captopril and ISIS 461756-induced vascular permeability.

Group 4 consisted of 8 C57BL/6J-Tyrc-2J mice treated with PBS administered subcutaneously twice a week for 4 weeks. On day 14, the mice were treated with 50 mg/kg of the antisense oligonucleotide targeting C1 inhibitor, ISIS 461756, administered subcutaneously twice a week for 2 weeks. At the end of the treatment period, the mice were intraperitoneally administered 20 µg of captopril. The mice were then also intraperitoneally administered 30 µg of HOE-140. Group 4 served as a positive control for inhibition of vascular permeability with HOE-140.

Group 5 consisted of 8 C57BL/6J-Tyrc-2J mice treated with 40 mg/kg of control oligonucleotide ISIS 141923, a 5-10-5 MOE gapmer with no known murine target, (CCTTCCCTGAAGGTTCCTCC; SEQ ID NO: 38) administered subcutaneously twice a week for 4 weeks. On day 14, the mice were treated with 50 mg/kg of the antisense oligonucleotide targeting C1 inhibitor, ISIS 461756, administered subcutaneously twice a week for 2 weeks. At the end of the treatment period, the mice were intraperitoneally administered 20 µg of captopril. Group 5 served as a control group for captopril and ISIS 461756-induced vascular permeability.

Group 6 consisted of 8 C57BL/6J-Tyrc-2J mice and was treated with 40 mg/kg of oligonucleotide ISIS 410944, a 5-10-5 MOE gamper targeting murine Factor 12, administered subcutaneously twice a week for 4 weeks. At the end of the treatment period, the mice were intraperitoneally administered 20 µg of captopril. Group 6 served as the experimental group for examining the effect of Factor 12 ASO on captopril-induced vascular permeability.

Group 7 consisted of 8 C57BL/6J-Tyrc-2J mice treated with 40 mg/kg of oligonucleotide ISIS 410944 administered subcutaneously twice a week for 4 weeks. On day 14, the mice were treated with 50 mg/kg of the antisense oligonucleotide targeting C1 inhibitor, ISIS 461756, administered subcutaneously twice a week for 2 weeks. At the end of the treatment period, the mice were intraperitoneally administered 20 µg of captopril. Group 7 served as the experimental group for examining the effect of Factor 12 ASO on captopril and ISIS 461756-induced vascular permeability.

All the groups were then injected with 30 mg/kg of Evans Blue solution into the tail vein. The mice were sacrificed 30 min after the Evans Blue solution administration and colons, feet, ears, and intestines were harvested. Blood samples were taken through cardiac puncture.

TABLE 1

Treatment groups

| Group No. | Treatment | Captopril | ISIS 461756 | HOE-140 |
|---|---|---|---|---|
| 1. (N = 4) | PBS | No | No | No |
| 2. (N = 8) | PBS | Yes | No | No |
| 3. (N = 8) | PBS | Yes | Yes | No |
| 4. (N = 8) | PBS | Yes | Yes | Yes |
| 5. (N = 8) | ISIS 141923 | Yes | Yes | No |
| 6. (N = 8) | ISIS 410944 | Yes | No | No |
| 7. (N = 8) | ISIS 410944 | Yes | Yes | No |

Evans Blue Dye Quantification

The harvested tissues from the feet, colon, ears, and intestines were placed separately in formamide solution overnight to leach out the Evans Blue dye. The formamide solution containing ear and feet tissue was heated to 55° C. and left overnight. The color intensity of the dye-infused formamide solution was then measured at $OD_{600nm}$ and is presented in Table 2. Mice displaying any manifestation of angioedema take up more dye and, therefore, demonstrate high OD values.

As shown in Table 2, mice treated with ISIS 410944 and a vascular permeability inducing agent (Groups 6 and 7) have reduced vascular permeability as compared to those mice treated with a vascular permeability agent and no anti-vascular permeability agent (Groups 2 and 3).

As presented in Table 2, treatment with ISIS 410944 prevents vascular permeability in mice treated with captopril (Group 6) and in mice treated with captopril and ISIS 461756 (Group 7) compared to the respective PBS control groups (Groups 2 and 3). Measures of vascular permeability in mice of Groups 6 and 7 were also reduced in comparison to the mice treated with the control oligonucleotide, ISIS 141923 (Group 5), where vascular permeability was induced with captopril and ISIS 461756. Measures of vascular permeability in the colon and feet tissues of both the treatment groups (Groups 6 and 7) were also reduced compared to basal levels, as observed in mice treated with only PBS (Group 1). Reduced vascular permeability in mice treated with ISIS 410944 was comparable to that seen in mice treated with the bradykinin 2 receptor antagonist, HOE140, which served as a positive control in this assay.

Therefore, antisense inhibition of Factor 12 mRNA may be beneficial for the treatment and prevention of vascular permeability, which is symptomatic of HAE.

TABLE 2

$OD_{600 nm}$ of Evans Blue dye to measure vascular permeability

| Group No. | Treatment | Captopril | ISIS 461756 | HOE-140 | Colons | Intestines | Feet | Ears |
|---|---|---|---|---|---|---|---|---|
| 1 | PBS | No | No | No | 0.26 | 0.16 | 0.11 | 0.02 |
| 2 | PBS | Yes | No | No | 0.49 | 0.29 | 0.12 | 0.07 |

TABLE 2-continued

OD$_{600\,nm}$ of Evans Blue dye to measure vascular permeability

| Group No. | Treatment | Captopril | ISIS 461756 | HOE-140 | Colons | Intestines | Feet | Ears |
|---|---|---|---|---|---|---|---|---|
| 3 | PBS | Yes | Yes | No | 0.49 | 0.34 | 0.11 | 0.12 |
| 4 | PBS | Yes | Yes | Yes | 0.14 | 0.18 | 0.07 | 0.09 |
| 5 | ISIS 141923 | Yes | Yes | No | 0.44 | 0.29 | 0.14 | 0.08 |
| 6 | ISIS 410944 | Yes | No | No | 0.18 | 0.25 | 0.05 | 0.14 |
| 7 | ISIS 410944 | Yes | Yes | No | 0.20 | 0.28 | 0.06 | 0.06 |

Quantification of High Molecular Weight Kininogen (HMWK)

Western blot quantification of HMWK from blood samples are presented in FIG. 1.

As shown in FIG. 1, samples from Groups 1 and 2 have low levels of HMWK as compared to Groups 6 and 7 indicating that vascular permeability is reversed in Groups 6 and 7. Also as shown in FIG. 1, samples from Groups 1 and 2 have increased HMWK cleavage product as compared to Groups 6 and 7. Thus, lack of HMWK is caused by kallikrein cleavage of HMWK into cleavage products (including bradykinin and HKa).

Example 3

In Vivo Effect of Antisense Inhibition of Murine Factor 12 on Basal Permeability and Captopril-Induced Permeability in Mice Basal permeability is the level of vascular permeability occurring in the tissues of naïve, untreated mice. The effect of ISIS 410944 in the prevention of vascular permeability, either basal or captopril-induced, was evaluated.

Treatment

The various treatment groups for this assay are presented in Table 3.

Group 1 consisted of 8 mice and was treated with PBS administered subcutaneously twice a week for 4 weeks. No other treatment was administered to Group 1 which served as a control group to measure the basal levels of vascular permeability.

Group 2 consisted of 8 mice and was treated with PBS administered subcutaneously twice a week for 4 weeks. At the end of the treatment period, the mice were intraperitoneally administered 20 µg of captopril. Group 2 served as the negative control group for captopril-induced vascular permeability.

Group 3 consisted of 8 mice and was treated with PBS administered subcutaneously twice a week for 4 weeks. At the end of the treatment period, the mice were intraperitoneally administered 30 µg of HOE-140. Group 3 served as a positive control for inhibition of basal vascular permeability.

Group 4 consisted of 8 mice and was treated with PBS administered subcutaneously twice a week for 4 weeks. At the end of the treatment period, the mice were intraperitoneally administered 20 µg of captopril. The mice were also intraperitoneally administered 30 µg of HOE-140. Group 4 served as a positive control for inhibition of captopril-induced vascular permeability.

Group 5 consisted of 8 mice and was treated with 40 mg/kg of ISIS 410944 administered subcutaneously twice a week for 4 weeks. Group 5 served as an experimental treatment group for examining the effect of ISIS 410944 on basal vascular permeability.

Group 6 consisted of 8 mice and was treated with 40 mg/kg of ISIS 410944 administered subcutaneously twice a week for 4 weeks. At the end of the treatment period, the mice were intraperitoneally administered 20 µg of captopril. Group 6 served as an experimental treatment group for examining the effect of ISIS 410944 on captopril-induced vascular permeability.

All the groups were then injected with 30 mg/kg of Evans Blue solution. The mice were sacrificed 30 min after the Evans Blue solution administration and colons, feet, ears, and intestines were harvested.

TABLE 3

Treatment groups

| Group No. | Treatment | Captopril | HOE-140 |
|---|---|---|---|
| 1. (N = 8) | PBS | No | No |
| 2. (N = 8) | PBS | Yes | No |
| 3. (N = 8) | PBS | No | Yes |
| 4. (N = 8) | PBS | Yes | Yes |
| 5. (N = 8) | ISIS 410944 | No | No |
| 6. (N = 8) | ISIS 410944 | Yes | No |

Evans Blue Dye Quantification

The harvested tissues from the feet, colon, ears, and intestine were placed separately in formamide solution overnight to leach out the Evans Blue dye. The formamide solution containing ears and feet tissue was heated to 55° C. and left overnight. The color intensity of the dye-infused formamide solution was then measured at OD$_{600nm}$, and is presented in Table 4. Mice displaying any manifestation of angioedema take up more dye and, therefore, demonstrate high OD values.

As presented in Table 4, mice treated with ISIS 410944 demonstrated reduced basal vascular permeability compared to the PBS control (Group 5 vs Group 1). The reduction in basal vascular permeability by treatment with ISIS 410944 was comparable to that caused by treatment with HOE140 (Group 3, which served as the positive control). Mice treated with ISIS 410944 also demonstrated reduced captopril-induced vascular permeability in most tissues compared to the PBS control (Group 6 vs. Group 2). The reduction in captopril-induced vascular permeability by treatment with ISIS 410944 was comparable to that caused by treatment with HOE140 (Group 4, which served as the positive control).

TABLE 4

OD$_{600\,nm}$ of Evans Blue dye to measure vascular permeability

| Group No. | Treatment | Captopril | HOE-140 | Colon | Feet | Intestine | Ears |
|---|---|---|---|---|---|---|---|
| 1 | PBS | No | No | 0.27 | 0.08 | 0.23 | 0.06 |
| 2 | PBS | Yes | No | 0.61 | 0.08 | 0.24 | 0.01 |
| 3 | PBS | No | Yes | 0.18 | 0.06 | 0.21 | 0.03 |

TABLE 4-continued

OD$_{600 nm}$ of Evans Blue dye to measure vascular permeability

| Group No. | Treatment | Captopril | HOE-140 | Colon | Feet | Intestine | Ears |
|---|---|---|---|---|---|---|---|
| 4 | PBS | Yes | Yes | 0.29 | 0.03 | 0.14 | 0 |
| 5 | ISIS 410944 | No | No | 0.19 | 0.06 | 0.22 | 0.04 |
| 6 | ISIS 410944 | Yes | No | 0.29 | 0.04 | 0.13 | 0.005 |

Example 4

Dose-Dependent Effect of Antisense Inhibition of Murine Factor 12 on Vascular Permeability in an Angioedema Mouse Model The effect of varying doses on ISIS 410944 on captopril-induced vascular permeability was evaluated.

Treatment

The various treatment groups for this assay are presented in Table 5.

Group 1 consisted of 4 mice and was treated with PBS administered subcutaneously twice a week for 3 weeks. No other treatment was administered to Group 1 which served as a control group to measure the basal levels of vascular permeability.

Group 2 consisted of 8 mice and was treated with PBS administered subcutaneously twice a week for 3 weeks. At the end of the treatment period, the mice were intraperitoneally administered 20 µg of captopril. Group 2 served as the control group for captopril-induced vascular permeability.

Group 3 consisted of 4 mice and was treated with PBS administered subcutaneously twice a week for 3 weeks. At the end of the treatment period, the mice were intraperitoneally administered 20 µg of captopril. The mice were also intraperitoneally administered 30 µg of HOE-140. Group 3 served as a positive control for inhibition of captopril-induced vascular permeability.

Groups 4, 5, 6, 7, 8, and 9 consisted of 8 mice each and were treated with 2.5 mg/kg, 5 mg/kg, 10 mg/kg, 20 mg/kg, 40 mg/kg, or 80 mg/kg (corresponding to 5 mg/kg, 10 mg/kg, 20 mg/kg, 40 mg/kg, 80 mg/kg, or 160 mg/kg per week), respectively, of ISIS 410944 administered subcutaneously twice a week for 3 weeks. At the end of the treatment period, the mice of all the groups were intraperitoneally administered 20 µg of captopril. Groups 4-9 served as the experimental treatment groups for examining the effect of varying doses of ISIS 410944 on captopril-induced vascular permeability.

All the groups were then injected with 30 mg/kg of Evans Blue solution in the tail vein. The mice were sacrificed 30 min after the Evans Blue solution administration and colons, feet, ears, and intestines were harvested. Blood samples were taken through cardiac puncture.

TABLE 5

Treatment groups

| Group No. | Treatment | Dose (mg/kg/wk) | Captopril | HOE-140 |
|---|---|---|---|---|
| 1. (N = 4) | PBS | — | No | No |
| 2. (N = 8) | PBS | — | Yes | No |
| 3. (N = 4) | PBS | — | Yes | Yes |
| 4. (N = 8) | ISIS 410944 | 160 | Yes | No |
| 5. (N = 8) | ISIS 410944 | 80 | Yes | No |
| 6. (N = 8) | ISIS 410944 | 40 | Yes | No |
| 7. (N = 8) | ISIS 410944 | 20 | Yes | No |
| 8. (N = 8) | ISIS 410944 | 10 | Yes | No |
| 9. (N = 8) | ISIS 410944 | 5 | Yes | No |

Quantification of Vascular Permeability

The harvested tissues were placed in formamide solution overnight to leach out the Evans Blue dye. The formamide solution containing feet tissue was heated to 55° C. and left overnight. The color intensity of the dye-infused formamide solution was then measured at OD$_{600nm}$, and is presented in Table 6. Mice displaying any manifestation of angioedema take up more dye and, therefore, demonstrate high OD values.

As presented in Table 6, mice treated with higher doses of ISIS 410944 (Groups 4 and 5) had reduced levels of captopril-induced vascular permeability compared to the corresponding PBS control group (Group 2). The reduction in vascular permeability in mice of these treatment groups (Groups 4 and 5) were comparable to the levels of basal vascular permeability (as shown in Group 1) as well as in mice treated with HOE140 (Group 3).

TABLE 6

OD$_{600 nm}$ of Evans Blue dye to measure vascular permeability

| Group No. | Treatment | Dose (mg/kg) | Captopril | HOE-140 | Colon | Feet | Intestine |
|---|---|---|---|---|---|---|---|
| 1 | PBS | — | No | No | 0.23 | 0.15 | 0.11 |
| 2 | PBS | — | Yes | No | 0.45 | 0.19 | 0.16 |
| 3 | PBS | — | Yes | Yes | 0.24 | 0.09 | 0.10 |
| 4 | ISIS 410944 | 160 | Yes | No | 0.20 | 0.10 | 0.13 |
| 5 | ISIS 410944 | 80 | Yes | No | 0.22 | 0.12 | 0.14 |
| 6 | ISIS 410944 | 40 | Yes | No | 0.39 | 0.19 | 0.16 |
| 7 | ISIS 410944 | 20 | Yes | No | 0.45 | 0.18 | 0.19 |
| 8 | ISIS 410944 | 10 | Yes | No | 0.58 | 0.14 | 0.20 |
| 9 | ISIS 410944 | 5 | Yes | No | 0.48 | 0.19 | 0.16 |

Quantification of Vascular Leakage

The blood drawn through cardiac puncture was immediately mixed with 3 times the volume of ice-cold ethanol. The solution was centrifuged at 15,000 g for 20 minutes at 4° C. to remove cell debris and precipitated plasma proteins. The ethanol extracts were further purified by ultra-filtration through a 10 kDa MWCO filter. The color intensity of the ethanol extracted plasma solution was then measured at OD$_{620nm}$. The results are presented in Table 7 as percentage increase or decrease of the OD values of the Group 1 PBS control. Mice displaying any manifestation of angioedema take up more dye and, therefore, demonstrate high OD values. Mice treated with 160 mg/kg/week and 80 mg/kg/week of ISIS 410944 (Groups 4 and 5) demonstrated less vascular leakage compared to the PBS negative control treated with captopril (Group 2). The results from Groups 4 and 5 were comparable to the positive control treated with HOE140 (Group 3).

TABLE 7

Percentage of OD$_{620 nm}$ of Evans Blue dye compared to the PBS basal control to measure vascular leakage

| Group No. | Treatment | Dose (mg/kg) | Captopril | HOE-140 | Plasma |
|---|---|---|---|---|---|
| 2 | PBS | — | Yes | No | -37 |
| 3 | PBS | — | Yes | Yes | 70 |
| 4 | ISIS 410944 | 160 | Yes | No | 36 |
| 5 | ISIS 410944 | 80 | Yes | No | 42 |
| 6 | ISIS 410944 | 40 | Yes | No | -20 |
| 7 | ISIS 410944 | 20 | Yes | No | -11 |
| 8 | ISIS 410944 | 10 | Yes | No | -19 |
| 9 | ISIS 410944 | 5 | Yes | No | -1 |

Example 5

Dose-Dependent Effect of Antisense Inhibition of Murine Factor 12 on Basal Permeability in Mice The effect of varying doses on ISIS 410944 on basal vascular permeability was evaluated.

Treatment

The various treatment groups for this assay are presented in Table 8.

Group 1 consisted of 8 mice and was treated with PBS administered subcutaneously twice a week for 3 weeks. No other treatment was administered to Group 1 which served as a control group to measure the basal levels of vascular permeability.

Group 2 consisted of 4 mice and was treated with PBS administered subcutaneously twice a week for 3 weeks. At the end of the treatment period, the mice were intraperitoneally administered 30 µg of HOE-140. Group 2 served as a positive control for inhibition of basal vascular permeability.

Groups 3, 4, 5, 6, 7, and 8 consisted of 8 mice each and were treated with 2.5 mg/kg, 5 mg/kg, 10 mg/kg, 20 mg/kg, 40 mg/kg, or 80 mg/kg (corresponding to 5 mg/kg, 10 mg/kg, 20 mg/kg, 40 mg/kg, 80 mg/kg, or 160 mg/kg per week), respectively, of ISIS 410944 administered subcutaneously twice a week for 3 weeks. Groups 4-9 served as the experimental treatment groups for examining the effect of varying does of ISIS 410944 on basal vascular permeability.

All the groups were then injected with 30 mg/kg of Evans Blue solution in the tail vein. The mice were sacrificed 30 min after the Evans Blue solution administration and colons, feet, ears, and intestines were harvested. Blood samples were taken through cardiac puncture.

TABLE 8

Treatment groups

| Group No. | Treatment | Dose (mg/kg/week) | HOE-140 |
|---|---|---|---|
| 1. (N = 8) | PBS | — | No |
| 2. (N = 4) | PBS | — | Yes |
| 3. (N = 8) | ISIS 410944 | 160 | No |
| 4. (N = 8) | ISIS 410944 | 80 | No |
| 5. (N = 8) | ISIS 410944 | 40 | No |
| 6. (N = 8) | ISIS 410944 | 20 | No |
| 7. (N = 8) | ISIS 410944 | 10 | No |
| 8. (N = 8) | ISIS 410944 | 5 | No |

Quantification of Vascular Permeability

The harvested tissues from the feet, colon, and ears were placed in formamide solution overnight to leach out the Evans Blue dye. The formamide solution containing feet and ear tissue was heated to 55° C. and left overnight. The color intensity of the dye-infused formamide solution was then measured at $OD_{600nm}$, and is presented in Table 9. Higher OD values are associated with higher levels of permeability.

As presented in Table 9, mice treated with ISIS 410944 at all doses (Groups 3-8) demonstrated reduced basal vascular permeability compared to the PBS control (Group 1). The reduction in basal vascular permeability of the ISIS oligonucleotide-treated groups was comparable to the same demonstrated in the positive control group treated with HOE140 (Group 2).

TABLE 9

$OD_{600\,nm}$ of Evans Blue dye to measure vascular permeability

| Group No. | Treatment | Dose (mg/kg/week) | HOE-140 | Colon | Feet | Ears | Intestines |
|---|---|---|---|---|---|---|---|
| 1 | PBS | — | No | 0.31 | 0.12 | 0.007 | 0.16 |
| 2 | PBS | — | Yes | 0.27 | 0.06 | 0.05 | 0.11 |
| 3 | ISIS 410944 | 160 | No | 0.25 | 0.07 | 0.011 | 0.14 |
| 4 | ISIS 410944 | 80 | No | 0.24 | 0.06 | 0.009 | 0.11 |
| 5 | ISIS 410944 | 40 | No | 0.27 | 0.06 | 0.006 | 0.13 |
| 6 | ISIS 410944 | 20 | No | 0.27 | 0.07 | 0.004 | 0.15 |
| 7 | ISIS 410944 | 10 | No | 0.28 | 0.06 | 0.005 | 0.14 |
| 8 | ISIS 410944 | 5 | No | 0.33 | 0.08 | 0.008 | 0.15 |

Quantification of Vascular Leakage

The blood drawn through cardiac puncture was immediately mixed with 3 times the volume of ice-cold ethanol. The solution was centrifuged at 15,000 g for 20 minutes at 4° C. to remove cell debris and precipitated plasma proteins. The ethanol extracts were further purified by ultra-filtration through a 10 kDa MWCO filter. The color intensity of the ethanol extracted plasma solution was then measured at $OD_{620nm}$. The results are presented in Table 10 as percentage increase or decrease of the OD values of the Group 1 PBS control. It was expected that treatment groups may display higher OD values due to reduced vascular leakage. All the mice in the ISIS oligonucleotide-treated groups demonstrated significantly reduced vascular leakage compared to the PBS negative control.

TABLE 10

Percentage of $OD_{620\,nm}$ of Evans Blue dye compared to the PBS basal control to measure vascular leakage

| Group No. | Treatment | Dose (mg/kg/week) | HOE-140 | Plasma |
|---|---|---|---|---|
| 3 | ISIS 410944 | 160 | No | 92 |
| 4 | ISIS 410944 | 80 | No | 79 |
| 5 | ISIS 410944 | 40 | No | 84 |
| 6 | ISIS 410944 | 20 | No | 68 |
| 7 | ISIS 410944 | 10 | No | 44 |

Quantification of High Molecular Weight Kininogen (HMWK)

Figure 2:
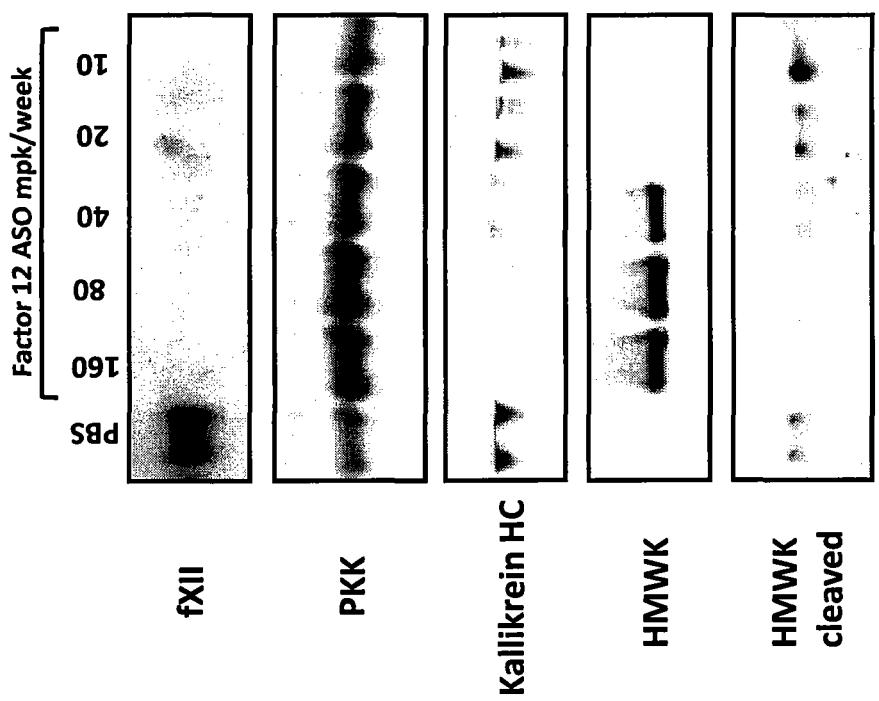

Western blot quantification of HMWK from blood samples are presented in FIG. 2 and Tables 11 and 12. As shown in Table 11, Groups treated with 410944 have higher levels of HMWK as compared to PBS control, increasing in a dose-dependent manner. Treatment with Factor 12 antisense oligonucleotide results in stabilization of HMWK. Thus, vascular permeability is reduced in ISIS 410944-treated groups in a dose-dependent manner. As shown in Table 12, Groups treated with 410944 have lower HMWK cleavage product as compared to PBS control, decreasing in a dose-dependent manner. Thus, reduced HMWK is caused by kallikrein cleavage of HMWK into cleavage products (including bradykinin and HKa). Data are presented in Intensity Units as measured by densitometer.

TABLE 11

Quantification of HMWK by densitometer

| Group No | Treatment | Dose (mg/kg/week) | Intensity Units |
|---|---|---|---|
| 1 | PBS | — | 2362 |
| 3 | ISIS 410944 | 160 | 577753 |
| 4 | ISIS 410944 | 80 | 426446 |

TABLE 11-continued

Quantification of HMWK by densitometer

| Group No | Treatment | Dose (mg/kg/week) | Intensity Units |
|---|---|---|---|
| 5 | ISIS 410944 | 40 | 298551 |
| 6 | ISIS 410944 | 20 | 114112 |
| 7 | ISIS 410944 | 10 | 30893 |

TABLE 12

Quantification of HMWK cleavage product by densitometer

| Group No | Treatment | Dose (mg/kg/week) | Intensity Units |
|---|---|---|---|
| 1 | PBS | — | 26038 |
| 3 | ISIS 410944 | 160 | 1859 |
| 4 | ISIS 410944 | 80 | 8001 |
| 5 | ISIS 410944 | 40 | 14710 |
| 6 | ISIS 410944 | 20 | 20553 |
| 7 | ISIS 410944 | 10 | 29037 |

Example 6

Combination Therapy of Antisense Oligonucleotides Targeting Factor 12 and Kallikrein on Captopril-Induced Vascular Permeability in Mice Mice were treated with varying doses of ISIS 482584, a 5-10-5 MOE gapmer targeting kallikrein (KLKB1) (GGCATATTGGTTTTTGGAAT; SEQ ID NO: 39) and ISIS 410944 in a captopril-induced vascular permeability model.

Treatment

The various treatment groups for this assay are presented in Table 13.

Group 1 consisted of 4 mice and was treated with PBS administered subcutaneously twice a week for 3 weeks. No other treatment was administered to Group 1 which served as a control group to measure the basal levels of vascular permeability.

Group 2 consisted of 8 mice and was treated with PBS administered subcutaneously twice a week for 3 weeks. At the end of the treatment period, the mice were intraperitoneally administered 20 µg of captopril. Group 2 served as the control group for captopril-induced vascular permeability.

Group 3 consisted of 4 mice and was treated with PBS administered subcutaneously twice a week for 3 weeks. At the end of the treatment period, the mice were intraperitoneally administered 20 µg of captopril. The mice were also intraperitoneally administered 30 µg of HOE-140. Group 3 served as a positive control for inhibition of captopril-induced vascular permeability.

Groups 4, 5, 6, 7, and 8 consisted of 8 mice each and were treated with 2.5 mg/kg, 5 mg/kg, 10 mg/kg, 20 mg/kg, or 40 mg/kg (corresponding to 5 mg/kg, 10 mg/kg, 20 mg/kg, 40 mg/kg, or 80 mg/kg per week), respectively, of ISIS 410944 and ISIS 482584 each administered subcutaneously twice a week for 3 weeks. At the end of the treatment period, the mice of all the groups were intraperitoneally administered 20 µg of captopril. Groups 4-8 served as the experimental treatment groups for examining the effect of ISIS 410944 and ISIS 482584 on captopril-induced vascular permeability.

All the groups were then injected with 30 mg/kg of Evans Blue solution in the tail vein. The mice were sacrificed 30 min after the Evans Blue solution administration and colons, feet, ears, and intestines were harvested.

TABLE 13

Treatment groups

| Group No. | Treatment | Dose (mg/kg/wk) | Captopril | HOE-140 |
|---|---|---|---|---|
| 1. (N = 4) | PBS | — | No | No |
| 2. (N = 8) | PBS | — | Yes | No |
| 3. (N = 4) | PBS | — | Yes | Yes |
| 4. (N = 8) | ISIS 410944 + ISIS 482584 | 80 | Yes | No |
| 5. (N = 8) | ISIS 410944 + ISIS 482584 | 40 | Yes | No |
| 6. (N = 8) | ISIS 410944 + ISIS 482584 | 20 | Yes | No |
| 7. (N = 8) | ISIS 410944 + ISIS 482584 | 10 | Yes | No |
| 8. (N = 8) | ISIS 410944 + ISIS 482584 | 5 | Yes | No |

Quantification of Vascular Permeability

The harvested tissues from the feet, colon, and ears were placed in formamide solution overnight to leach out the Evans Blue dye. The formamide solution containing feet and ear tissue was heated to 55° C. and left overnight. The color intensity of the dye-infused formamide solution was then measured at $OD_{600nm}$, and is presented in Table 14. Mice displaying any manifestation of angioedema take up more dye and, therefore, demonstrate high OD values. As presented in Table 14, most of the tissues of mice treated with a combination of ISIS 410944 and ISIS 482584 at all doses (Groups 3-8) demonstrated reduced vascular permeability compared to the PBS control (Group 1). The reduction in vascular permeability of the ISIS oligonucleotide-treated groups was comparable to the same demonstrated in the basal PBS control (Group 1), as well as the positive control group treated with HOE140 (Group 2). Combination of Factor 12 and KLKB1 antisense oligonucleotides results in synergistic decrease in permeability. As expected, a corresponding synergistic decrease in vascular leakage was also observed.

TABLE 14

$OD_{600\,nm}$ of Evans Blue dye to measure vascular permeability

| Group No. | Treatment | Dose (mg/kg/wk) | Captopril | HOE-140 | Colon | Feet | Intestines | Ears |
|---|---|---|---|---|---|---|---|---|
| 1 | PBS | — | No | No | 0.24 | 0.11 | 0.13 | 0.01 |
| 2 | PBS | — | Yes | No | 0.38 | 0.15 | 0.11 | 0.05 |
| 3 | PBS | — | Yes | Yes | 0.23 | 0.06 | 0.15 | 0.04 |
| 4 | ISIS 410944 + ISIS 482584 | 80 | Yes | No | 0.19 | 0.07 | 0.11 | 0.04 |
| 5 | ISIS 410944 + ISIS 482584 | 40 | Yes | No | 0.19 | 0.07 | 0.12 | 0.03 |
| 6 | ISIS 410944 + ISIS 482584 | 20 | Yes | No | 0.22 | 0.08 | 0.12 | 0.04 |

TABLE 14-continued

OD$_{600\,nm}$ of Evans Blue dye to measure vascular permeability

| Group No. | Treatment | Dose (mg/kg/wk) | Captopril | HOE-140 | Colon | Feet | Intestines | Ears |
|---|---|---|---|---|---|---|---|---|
| 7 | ISIS 410944 + ISIS 482584 | 10 | Yes | No | 0.38 | 0.13 | 0.13 | 0.05 |
| 8 | ISIS 410944 + ISIS 482584 | 5 | Yes | No | 0.53 | 0.12 | 0.13 | 0.03 |

Example 7

Combination Therapy of Antisense Oligonucleotides Targeting Factor 12 and KLKB1 on Basal Vascular Permeability in Mice Mice were treated with varying doses of ISIS 482584, an antisense oligonucleotide targeting kallikrein (KLKB1) and ISIS 410944 in a basal vascular permeability model.

Treatment

The various treatment groups for this assay are presented in Table 15.

Group 1 consisted of 8 mice and was treated with PBS administered subcutaneously twice a week for 3 weeks. No other treatment was administered to Group 1 which served as a control group to measure the basal levels of basal vascular permeability.

Group 2 consisted of 4 mice and was treated with PBS administered subcutaneously twice a week for 3 weeks. At the end of the treatment period, the mice were intraperitoneally administered 30 µg of HOE-140. Group 2 served as a positive control for inhibition of basal vascular permeability.

Groups 3, 4, 5, 6, and 7 consisted of 8 mice each and were treated with 2.5 mg/kg, 5 mg/kg, 10 mg/kg, 20 mg/kg, or 40 mg/kg (corresponding to 5 mg/kg, 10 mg/kg, 20 mg/kg, 40 mg/kg, or 80 mg/kg per week), respectively, of ISIS 410944 and ISIS 482584 each administered subcutaneously twice a week for 3 weeks. Groups 3-7 served as the experimental treatment groups for examining the effect of ISIS 410944 and ISIS 482584 on basal vascular permeability.

All the groups were then injected with 30 mg/kg of Evans Blue solution in the tail vein. The mice were sacrificed 30 min after the Evans Blue solution administration and colons, feet, ears, and intestines were harvested.

TABLE 15

Treatment groups

| Group No. | Treatment | Dose (mg/kg/wk) | HOE-140 |
|---|---|---|---|
| 1. (N = 8) | PBS | — | No |
| 2. (N = 4) | PBS | — | Yes |
| 3. (N = 8) | ISIS 410944 + ISIS 482584 | 80 | No |
| 4. (N = 8) | ISIS 410944 + ISIS 482584 | 40 | No |
| 5. (N = 8) | ISIS 410944 + ISIS 482584 | 20 | No |
| 6. (N = 8) | ISIS 410944 + ISIS 482584 | 10 | No |
| 7. (N = 8) | ISIS 410944 + ISIS 482584 | 5 | No |

Quantification of Vascular Permeability

The harvested tissues from the feet, colon, and ears were placed in formamide solution overnight to leach out the Evans Blue dye. The formamide solution containing feet and ear tissue was heated to 55° C. and left overnight. The color intensity of the dye-infused formamide solution was then measured at OD$_{600nm}$, and is presented in Table 16. Higher OD values are associated with higher levels of permeability. As presented in Table 16, most of the tissues of mice treated with a combination of ISIS 410944 and ISIS 482584 at all doses (Groups 2-7) demonstrated reduced vascular permeability compared to the PBS control (Group 1). The reduction in vascular permeability of the ISIS oligonucleotide-treated groups was comparable to the same demonstrated in positive control group treated with HOE140 (Group 2). Treatment with a combination of Factor 12 and KLKB1 antisense oligonucleotides resulted in a synergistic decrease in permeability. As expected, a corresponding synergistic decrease in vascular leakage was also observed.

TABLE 16

OD$_{600\,nm}$ of Evans Blue dye to measure vascular permeability

| Group No. | Treatment | Dose (mg/kg/wk) | HOE-140 | Colon | Feet | Intestines | Ears |
|---|---|---|---|---|---|---|---|
| 1 | PBS | — | No | 0.19 | 0.08 | 0.10 | 0.004 |
| 2 | PBS | — | Yes | 0.14 | 0.04 | 0.08 | 0.008 |
| 3 | ISIS 410944 + ISIS 482584 | 80 | No | 0.14 | 0.04 | 0.09 | 0.01 |
| 4 | ISIS 410944 + ISIS 482584 | 40 | No | 0.15 | 0.05 | 0.10 | 0.006 |
| 5 | ISIS 410944 + ISIS 482584 | 20 | No | 0.15 | 0.04 | 0.10 | 0.007 |
| 6 | ISIS 410944 + ISIS 482584 | 10 | No | 0.15 | 0.06 | 0.10 | 0.004 |
| 7 | ISIS 410944 + ISIS 482584 | 5 | No | 0.14 | 0.05 | 0.13 | 0.002 |

Example 8

Inhibition of Factor 12 Protein Activation by ISIS 482584

The effect of antisense inhibition of kallikrein (KLKB1) mRNA on Factor 12 protein activation was evaluated.

Treatment

The various treatment groups for this assay are presented in Table 17.

Group 1 consisted of 8 mice and was treated with PBS administered subcutaneously twice a week for 3 weeks. No other treatment was administered to Group 1 which served as a control group to measure Factor 12 activation.

Groups 2, 3, 4, 5, and 6 consisted of 8 mice each and were treated with 2.5 mg/kg, 5 mg/kg, 10 mg/kg, 20 mg/kg, or 40 mg/kg (corresponding to 5 mg/kg, 10 mg/kg, 20 mg/kg, 40 mg/kg, or 80 mg/kg per week), respectively of ISIS 482584 administered subcutaneously twice a week for 3 weeks. Groups 2-6 served as the treatment groups for measuring the effect of ISIS 482584 on Factor 12 activation.

At the end of the treatment period, plasma was harvested from the mice for the Spectrozyme® Factor 12a based amidolytic assay for Factor 12 in plasma.

TABLE 17

Treatment groups

| Group No. | Treatment | Dose (mg/kg/wk) |
|---|---|---|
| 1. (N = 8) | PBS | — |
| 2. (N = 8) | ISIS 482584 | 80 |
| 3. (N = 8) | ISIS 482584 | 40 |
| 4. (N = 8) | ISIS 482584 | 20 |
| 5. (N = 8) | ISIS 482584 | 10 |
| 6. (N = 8) | ISIS 482584 | 5 |

Assay for Factor 12 Activation in Plasma

Plasma (5 µL) was added to 85 µL of PBS with 1 ug/ml dextran sulfate (500 kDa) in a 96 well polypropelene microplate and the solution was incubated for 5 minutes at room temperature. Spectrozyme® FXIIa (10 µL of a 2 mM solution) and 0.2 mM KALLISTOP™ solution was added and the absorbance kinetic was measured at 405 nm. Factor 12 activation was measured in the linear phase of absorbance accumulation. The results are presented in Table 18 as a percentage of Factor 12 activation measured in the PBS control sample. As observed in Table 18, inhibition of kallikrein (KLKB1) by ISIS 482584 results in decreased activation of Factor 12 by its substrate, implying that PKK is required for proper factor 12 activation.

TABLE 18

Percentage Factor 12 activation compared to the PBS control

| Dose (mg/kg/wk) | % F12 activation |
|---|---|
| 80 | 14 |
| 40 | 24 |
| 20 | 47 |
| 10 | 63 |
| 5 | 82 |

Example 9

In Vivo Effect of Antisense Inhibition of Murine Factor 12 in a C1-INH Antisense Oligonucleotide-Induced Angioedema Model Vascular permeability induced by ISIS 461756, an antisense oligonucleotide which targets murine C1 inhibitor mRNA, increases vascular permeability in mice and replicates the pathology of hereditary angioedema. The effect of ISIS 410944 on this model was evaluated.

Treatment

One group of 8 mice was treated with 40 mg/kg ISIS 410944 administered subcutaneously twice a week for 3 weeks (weekly dose of 80 mg/kg). A second group of 8 mice was treated with 40 mg/kg of the control oligonucleotide, ISIS 141923, administered subcutaneously twice a week for 3 weeks (weekly dose of 80 mg/kg). A third group of 8 mice was treated with PBS administered subcutaneously twice a week for 3 weeks. On day 14, all the groups were treated with 12.5 mg/kg ISIS 461756 administered subcutaneously twice a week for 3 weeks (weekly dose of 25 mg/kg). A control group of mice was treated with PBS administered subcutaneously twice a week for 3 weeks but was not administered ISIS 461756.

At the end of the treatment period, all the groups were injected with 30 mg/kg of Evans Blue solution into the tail vein. The mice were sacrificed 30 min after the Evans Blue solution administration and colons, feet, ears, and intestines were harvested. The liver was also harvested for RNA analysis.

RNA Analysis

RNA was isolated from the liver for RT-PCR analysis of C1-INH and Factor 12 mRNAs. The primer probe set for C1-INH is RTS3218 (forward sequence GAGTCCCCCAGAGCCTACAGT, designated herein as SEQ ID NO: 25; reverse sequence TGTCATTTGTTATTGTGATGGCTACA, designated herein as SEQ ID NO: 26; probe sequence CTGCCCTCTACCTGGCCAACAACCA, designated herein as SEQ ID NO: 27). The primer probe set for Factor 12 is RTS2959 (forward sequence CAAAGGAGGGACATGTATCAACAC, designated herein as SEQ ID NO: 28; reverse sequence CTGGCAATGTTTCCCAGTGA, designated herein as SEQ ID NO: 29; probe sequence CCCAATGGGCCACACTGTCTCTGC, designated herein as SEQ ID NO: 30). The results are presented in Table 19 as percent inhibition compared to the PBS control not treated with ISIS 461756. The data indicates that ISIS 461756 significantly reduced C1-INH mRNA expression and that treatment with ISIS 410944 significantly reduced Factor 12 expression.

TABLE 19

Percent inhibition of mRNA expression in mice treated with ISIS 461756 compared to the untreated PBS control

| Treatment | C1-INH mRNA | Factor 12 mRNA |
|---|---|---|
| PBS | 76 | 0 |
| ISIS 141923 | 79 | 0 |
| ISIS 410944 | 77 | 95 |

Quantification of Vascular Permeability

The harvested tissues from the feet, colon, and intestine were placed in formamide solution overnight to leach out the Evans Blue dye. The formamide solution containing feet tissue was heated to 55° C. and left overnight. The color intensity of the dye-infused formamide solution was then measured at $OD_{600nm}$. The data is presented in Table 20 as percent increase or reduction compared to the PBS control not treated with ISIS 461756. The data indicates that treatment with ISIS 410944 prevented vascular permeability induced by ISIS 461756.

TABLE 20

Percent change in vascular permeability in mice treated with ISIS 461756 compared to the untreated PBS control

| Treatment | Colon | Feet | Intestines |
|---|---|---|---|
| PBS | 13 | 70 | 27 |
| ISIS 141923 | 2 | 80 | 14 |
| ISIS 410944 | −24 | −1 | −10 |

What is claimed is:

1. A method comprising,
prophylactically treating hereditary angioedema (HAE) in an animal identified as having HAE by administering to the animal a therapeutically effective amount of a compound comprising a modified oligonucleotide consisting of 12 to 30 linked nucleosides, wherein the modified oligonucleotide is at least 90% complementary to a Factor 12 nucleic acid.

2. The method of claim 1, wherein the prophylactic administering of the compound comprising a modified oligonucleotide prevents or ameliorates edema.

3. The method of claim 1, wherein the prophylactic administering of the compound comprising a modified oligonucleotide prevents or ameliorates vascular permeability.

4. The method of claim 1, wherein the prophylactic administering of the compound comprising a modified oligonucleotide prevents or ameliorates vascular leakage.

5. The method of claim 1, wherein the prophylactic administering of the compound comprising a modified oligonucleotide prevents or ameliorates inflammation.

6. The method of claim 1, wherein the animal is a human.

7. The method of claim 1, wherein the Factor 12 nucleic acid is a human Factor 12 nucleic acid.

8. The method of claim 7, wherein the human Factor 12 nucleic acid is SEQ ID NO: 1, SEQ ID NO: 2, SEQ ID NO: 3, SEQ ID NO: 4, SEQ ID NO: 5, SEQ ID NO: 6, SEQ ID NO: 7, or the complement of SEQ ID NO: 8.

9. The method of claim 8, wherein the modified oligonucleotide is 100% complementary to a human Factor 12 nucleic acid.

10. The method of claim 9, wherein the modified oligonucleotide is a single-stranded oligonucleotide.

11. The method of claim 10, wherein the modified oligonucleotide comprises at least one modified internucleoside linkage.

12. The method of claim 11, wherein the modified internucleoside linkage is a phosphorothioate internucleoside linkage.

13. The method of claim 8, comprising at least one nucleoside having a modified sugar.

14. The method of claim 13, wherein the modified sugar is a bicyclic sugar.

15. The method of claim 14, wherein the bicyclic sugar comprises a 4'-CH(CH$_3$)—O-2' bridge.

16. The method of claim 13, wherein the modified sugar comprises a 2'-O-methoxyethyl group.

17. The method of claim 8, wherein at least one nucleoside comprises a modified nucleobase.

18. The method of claim 17, wherein the modified nucleobase is a 5-methylcytosine.

19. The method of claim 8, comprising co-administering the compound comprising a modified oligonucleotide and any of the group selected from a serine protease inhibitor C1-INH recombinant protein, CINRYZE, BERINERT, KALBITOR, Icatibant, Ecallantide, attenuated androgens, anabolic steroids, antifibrinolytic agents, epsilon-aminocaproic acid, tranexamic acid.

20. The method of claim 8, wherein the administering is parenteral administration.

21. The method of claim 20, wherein the parenteral administration is any of subcutaneous or intravenous administration.

22. The method of claim 8, wherein the compound comprises a conjugate.

\* \* \* \* \*

SEQUENCE LISTING

<160> NUMBER OF SEQ ID NOS: 43

<210> SEQ ID NO 1
<211> LENGTH: 2060
<212> TYPE: DNA
<213> ORGANISM: Homo sapiens
<220> FEATURE:
<221> NAME/KEY: CDS
<222> LOCATION: (50)..(1897)

<400> SEQUENCE: 1

```
ctattgatct ggactcctgg ataggcagct ggaccaacgg acggatgcc atg agg gct        58
                                                     Met Arg Ala
                                                       1 ctg ctg ctc ctg ggg ttc ctg ctg gtg agc ttg gag tca aca ctt tcg        106
Leu Leu Leu Leu Gly Phe Leu Leu Val Ser Leu Glu Ser Thr Leu Ser
      5                  10                  15 att cca cct tgg gaa gcc ccc aag gag cat aag tac aaa gct gaa gag        154
Ile Pro Pro Trp Glu Ala Pro Lys Glu His Lys Tyr Lys Ala Glu Glu
 20                  25                  30                  35 cac aca gtc gtt ctc act gtc acc ggg gag ccc tgc cac ttc ccc ttc        202
His Thr Val Val Leu Thr Val Thr Gly Glu Pro Cys His Phe Pro Phe
                 40                  45                  50 cag tac cac cgg cag ctg tac cac aaa tgt acc cac aag ggc cgg cca        250
Gln Tyr His Arg Gln Leu Tyr His Lys Cys Thr His Lys Gly Arg Pro
             55                  60                  65 ggc cct cag ccc tgg tgt gct acc acc ccc aac ttt gat cag gac cag        298
Gly Pro Gln Pro Trp Cys Ala Thr Thr Pro Asn Phe Asp Gln Asp Gln
         70                  75                  80 cga tgg gga tac tgt ttg gag ccc aag aaa gtg aaa gac cac tgc agc        346
Arg Trp Gly Tyr Cys Leu Glu Pro Lys Lys Val Lys Asp His Cys Ser
     85                  90                  95 aaa cac agc ccc tgc cag aaa gga ggg acc tgt gtg aac atg cca agc        394
Lys His Ser Pro Cys Gln Lys Gly Gly Thr Cys Val Asn Met Pro Ser
100                 105                 110                 115 ggc ccc cac tgt ctc tgt cca caa cac ctc act gga aac cac tgc cag        442
Gly Pro His Cys Leu Cys Pro Gln His Leu Thr Gly Asn His Cys Gln
                120                 125                 130 aaa gag aag tgc ttt gag cct cag ctt ctc cgg ttt ttc cac aag aat        490
Lys Glu Lys Cys Phe Glu Pro Gln Leu Leu Arg Phe Phe His Lys Asn
            135                 140                 145 gag ata tgg tat aga act gag caa gca gct gtg gcc aga tgc cag tgc        538
Glu Ile Trp Tyr Arg Thr Glu Gln Ala Ala Val Ala Arg Cys Gln Cys
        150                 155                 160 aag ggt cct gat gcc cac tgc cag cgg ctg gcc agc cag gcc tgc cgc        586
Lys Gly Pro Asp Ala His Cys Gln Arg Leu Ala Ser Gln Ala Cys Arg
    165                 170                 175 acc aac ccg tgc ctc cat ggg ggt cgc tgc cta gag gtg gag ggc cac        634
Thr Asn Pro Cys Leu His Gly Gly Arg Cys Leu Glu Val Glu Gly His
180                 185                 190                 195
```

```
                                                  -continued cgc ctg tgc cac tgc ccg gtg ggc tac acc gga gcc ttc tgc gac gtg    682
Arg Leu Cys His Cys Pro Val Gly Tyr Thr Gly Ala Phe Cys Asp Val
            200                 205                 210 gac acc aag gca agc tgc tat gat ggc cgc ggg ctc agc tac cgc ggc    730
Asp Thr Lys Ala Ser Cys Tyr Asp Gly Arg Gly Leu Ser Tyr Arg Gly
            215                 220                 225 ctg gcc agg acc acg ctc tcg ggt gcg ccc tgt cag ccg tgg gcc tcg    778
Leu Ala Arg Thr Thr Leu Ser Gly Ala Pro Cys Gln Pro Trp Ala Ser
            230                 235                 240 gag gcc acc tac cgg aac gtg act gcc gag caa gcg cgg aac tgg gga    826
Glu Ala Thr Tyr Arg Asn Val Thr Ala Glu Gln Ala Arg Asn Trp Gly
            245                 250                 255 ctg ggc ggc cac gcc ttc tgc cgg aac ccg gac aac gac atc cgc ccg    874
Leu Gly Gly His Ala Phe Cys Arg Asn Pro Asp Asn Asp Ile Arg Pro
260                 265                 270                 275 tgg tgc ttc gtg ctg aac cgc gac cgg ctg agc tgg gag tac tgc gac    922
Trp Cys Phe Val Leu Asn Arg Asp Arg Leu Ser Trp Glu Tyr Cys Asp
                    280                 285                 290 ctg gca cag tgc cag acc cca acc cag gcg gcg cct ccg acc ccg gtg    970
Leu Ala Gln Cys Gln Thr Pro Thr Gln Ala Ala Pro Pro Thr Pro Val
            295                 300                 305 tcc cct agg ctt cat gtc cca ctc atg ccc gcg cag ccg gca ccg ccg   1018
Ser Pro Arg Leu His Val Pro Leu Met Pro Ala Gln Pro Ala Pro Pro
            310                 315                 320 aag cct cag ccc acg acc cgg acc ccg cct cag tcc cag acc ccg gga   1066
Lys Pro Gln Pro Thr Thr Arg Thr Pro Pro Gln Ser Gln Thr Pro Gly
325                 330                 335 gcc ttg ccg gcg aag cgg gag cag ccg cct tcc ctg acc agg aac ggc   1114
Ala Leu Pro Ala Lys Arg Glu Gln Pro Pro Ser Leu Thr Arg Asn Gly
340                 345                 350                 355 cca ctg agc tgc ggg cag cgg ctc cgc aag agt ctg tct tcg atg acc   1162
Pro Leu Ser Cys Gly Gln Arg Leu Arg Lys Ser Leu Ser Ser Met Thr
                360                 365                 370 cgc gtc gtt ggc ggg ctg gtg gcg cta cgc ggg gcg cac ccc tac atc   1210
Arg Val Val Gly Gly Leu Val Ala Leu Arg Gly Ala His Pro Tyr Ile
            375                 380                 385 gcc gcg ctg tac tgg ggc cac agt ttc tgc gcc ggc agc ctc atc gcc   1258
Ala Ala Leu Tyr Trp Gly His Ser Phe Cys Ala Gly Ser Leu Ile Ala
            390                 395                 400 ccc tgc tgg gtg ctg acg gcc gct cac tgc ctg cag gac cgg ccc gca   1306
Pro Cys Trp Val Leu Thr Ala Ala His Cys Leu Gln Asp Arg Pro Ala
405                 410                 415 ccc gag gat ctg acg gtg gtg ctc ggc cag gaa cgc cgt aac cac agc   1354
Pro Glu Asp Leu Thr Val Val Leu Gly Gln Glu Arg Arg Asn His Ser
420                 425                 430                 435 tgt gag ccg tgc cag acg ttg gcc gtg cgc tcc tac cgc ttg cac gag   1402
Cys Glu Pro Cys Gln Thr Leu Ala Val Arg Ser Tyr Arg Leu His Glu
                440                 445                 450 gcc ttc tcg ccc gtc agc tac cag cac gac ctg gct ctg ttg cgc ctt   1450
Ala Phe Ser Pro Val Ser Tyr Gln His Asp Leu Ala Leu Leu Arg Leu
            455                 460                 465 cag gag gat gcg gac ggc agc tgc gcg ctc ctg tcg cct tac gtt cag   1498
Gln Glu Asp Ala Asp Gly Ser Cys Ala Leu Leu Ser Pro Tyr Val Gln
            470                 475                 480 ccg gtg tgc ctg cca agc ggc gcc gcg cga ccc tcc gag acc acg ctc   1546
Pro Val Cys Leu Pro Ser Gly Ala Ala Arg Pro Ser Glu Thr Thr Leu
            485                 490                 495
```

```
tgc cag gtg gcc ggc tgg ggc cac cag ttc gag ggg gcg gag gaa tat      1594
Cys Gln Val Ala Gly Trp Gly His Gln Phe Glu Gly Ala Glu Glu Tyr
500                 505                 510                 515 gcc agc ttc ctg cag gag gcg cag gta ccg ttc ctc tcc ctg gag cgc      1642
Ala Ser Phe Leu Gln Glu Ala Gln Val Pro Phe Leu Ser Leu Glu Arg
            520                 525                 530 tgc tca gcc ccg gac gtg cac gga tcc tcc atc ctc ccc ggc atg ctc      1690
Cys Ser Ala Pro Asp Val His Gly Ser Ser Ile Leu Pro Gly Met Leu
        535                 540                 545 tgc gca ggg ttc ctc gag ggc ggc acc gat gcg tgc cag ggt gat tcc      1738
Cys Ala Gly Phe Leu Glu Gly Gly Thr Asp Ala Cys Gln Gly Asp Ser
    550                 555                 560 gga ggc ccg ctg gtg tgt gag gac caa gct gca gag cgc cgg ctc acc      1786
Gly Gly Pro Leu Val Cys Glu Asp Gln Ala Ala Glu Arg Arg Leu Thr
565                 570                 575 ctg caa ggc atc atc agc tgg gga tcg gcc tgt ggt gac cgc aac aag      1834
Leu Gln Gly Ile Ile Ser Trp Gly Ser Gly Cys Gly Asp Arg Asn Lys
580                 585                 590                 595 cca ggc gtc tac acc gat gtg gcc tac tac ctg gcc tgg atc cgg gag      1882
Pro Gly Val Tyr Thr Asp Val Ala Tyr Tyr Leu Ala Trp Ile Arg Glu
                600                 605                 610 cac acc gtt tcc tga ttgctcaggg actcatcttt ccctccttgg tgattccgca      1937
His Thr Val Ser
            615 gtgagagagt ggctggggca tggaaggcaa gattgtgtcc cattccccca gtgcggccag      1997 ctccgcgcca ggatggcgca ggaactcaat aaagtgcttt gaaaatgctg agaaaaaaaa      2057 aaa                                                                    2060

<210> SEQ ID NO 2
<211> LENGTH: 1480
<212> TYPE: DNA
<213> ORGANISM: Homo sapiens

<400> SEQUENCE: 2
ctccgcccca gggctccggg ctcccggcgc tctaacggcg cccgtcgtg tggctacagg        60 aacccggaca cgacatccg cccgtggtgc ttcgtgctga accgcgaccg gctgagctgg       120
gagtactgcg acctggcaca gtgccagacc ccaacccagg cggcgcctcc gaccccggtg      180
tcccctaggc ttcatgtccc actcatgccc gcgcagccgg caccgccgaa gcctcagccc      240
acgacccgga ccccgcctca gtcccagacc ccgggagcct tgccggcgaa gcgggagcag      300
ccgccttccc tgaccaggaa cggcccactg agctgcgggc agcggctccg caagagtctg      360
tcttcgatga cccgcgtcgt tggcgggctg gtggcgctac gcggggcgca ccctacatc       420 gccgcgctgt actggggcca cagtttctgc gccggcagcc tcatcgcccc ctgctgggtg      480
ctgacggccg ctcactgcct gcaggaccgg cgagtacccg cccgcccaga gccgcccag       540 gggccgcggc tcctccgtct cccagcgcag cttccacgct gcacccgaac ccgtgcccta      600
ccttctcccg ccccaccctt ctttccacgc ccctccggag ctcccgggga ggaagctgga      660
acacgggatt ggggttcggg agcaggggc ttccccagaa cgcttgtggc caggtctgag       720
agcgctgcct ctcccctacc cccccgcag gccgcaccc gaggatctga cggtggtgct        780
cggccaggaa cgccgtaacc acagctgtga gccgtgccag acgttggccg tgcgctccta      840
ccgcttgcac gaggccttct cgccgtcag ctaccagcac gacctggctc tgttgcgcct       900
tcaggaggat gcggacggca gctgcgcgct cctgtcgcct tacgttcagc cggtgtgcct      960
gccaagcggc gccgcgcgac cctccgagac cacgctctgc caggtggccg gctggggcca     1020
```

```
ccagttcgag ggggcggagg aatatgccag cttcctgcag gaggcgcagg taccgttcct    1080
ctccctggag cgctgctcag ccccggacgt gcacggatcc tccatcctcc ccggcatgct    1140
ctgcgcaggg ttcctcgagg gcggcaccga tgcgtgccag ggtgattccg gaggcccgct    1200
ggtgtgtgag gaccaagctg cagagcgccg gctcaccctg caaggcatca tcagctgggg    1260
atcgggctgt ggtgaccgca acaagccagg cgtctacacc gatgtggcct actacctggc    1320
ctggatccgg gagcacaccg tttcctgatt gctcagggac tcatctttcc ctccttggtg    1380
attccgcagt gagagagtgg ctggggcatg aaggcaaga ttgtgtccca ttcccccagt     1440
gcggccagct ccgcgccagg atggcgcagg aactcaataa                           1480
```

<210> SEQ ID NO 3
<211> LENGTH: 1572
<212> TYPE: DNA
<213> ORGANISM: Homo sapiens

<400> SEQUENCE: 3

```
ctccgcccca gggctccggg ctcccggcgc tctaacggcg cccgtcgtg tggctacagg       60 aacccggaca cgacatccg cccgtggtgc ttcgtgctga accgcgaccg gctgagctgg      120
gagtactgcg acctggcaca gtgccagacc ccaacccagg cggcgcctcc gaccccggtg    180 tccctaggc ttcatgtccc actcatgccc gcgcagccgg caccgccgaa gcctcagccc     240
acgacccgga ccccgcctca gtcccagacc ccgggaggtt aggaagtggg gggggaagga    300
ggagccgaga gggcgccggg cgagctagat tccggccagc cggccgcggg ctccccgtcc    360
tcagcccctg ctcctccaca gccttgccgg cgaagcggga gcagccgcct tccctgacca    420
ggaacggccc actgagctgc gggcagcggc tccgcaagag tctgtcttcg atgaccgcg     480 tcgttggcgg gctggtggcg ctacgcgggg cgcaccccta catcgccgcg ctgtactggg    540
gccacagttt ctgcgccggc agcctcatcg cccctgctg ggtgctgacg gccgctcact     600
gcctgcagga ccggcgagta cccgcccgcc cagagccgcc caggggccg cggctcctcc     660 gtctcccagc gcagcttcca cgctgcaccc gaacccgtgc cctaccttct cccgccccac    720
ccttctttcc acgcccctcc ggagctcccg gggaggaagc tggaacacgg gattgggggtt   780 cgggagcagg gggcttcccc agaacgcttg tggccaggtc tgagagcgct gcctctcccc    840
tacccccccc gcaggcccgc acccgaggat ctgacggtgt tgctcggcca ggaacgccgt    900
aaccacagct gtgagccgtg ccagacgttg ccgtgcgct cctaccgctt gcacgaggcc     960
ttctcgcccc tcagctacca gcacgacctg gctctgttgc gccttcagga ggatgcggac   1020
ggcagctgcg cgctcctgtc gccttacgtt cagccggtgt gcctgccaag cggcgccgcg   1080
cgaccctccg agaccacgct ctgccaggtg gccggctggg gccaccagtt cgaggggcg    1140 gaggaatatg ccagcttcct gcaggaggcg caggtaccgt tcctctcccct ggagcgctgc  1200 tcagccccgg acgtgcacgg atcctccatc ctccccggca tgctctgcgc agggttcctc   1260
gagggcggca ccgatgcgtg ccagggtgat tccggaggcc cgctggtgtg tgaggaccaa   1320
gctgcagagc gccggctcac cctgcaaggc atcatcagct ggggatcggg ctgtggtgac   1380
cgcaacaagc caggcgtcta caccgatgtg gcctactacc tggcctggat ccgggagcac   1440
accgtttcct gattgctcag ggactcatct ttccctcctt ggtgattccg cagtgagaga   1500
gtggctgggg catggaaggc aagattgtgt cccattcccc cagtgcggcc agctccgcgc   1560
caggatggcg ca                                                       1572
```

<210> SEQ ID NO 4
<211> LENGTH: 632
<212> TYPE: DNA
<213> ORGANISM: Homo sapiens

<400> SEQUENCE: 4

| cccacgcgtc | cggcgtgggg | ctgggtgacc | cctccgcccc | agggctccgg | gctcccggcg | 60 |
| ctctaacggc | gccccgtcgt | gtggctacag | gaacccggac | aacgacatcc | gcccgtggtg | 120 |
| cttcgtgctg | aaccgcgacc | ggctgagctg | ggagtactgc | gacctggcac | agtgccagac | 180 |
| cccaacccag | gcggcgcctc | cgaccccggt | gtcccctagg | cttcatgtcc | cactcatgcc | 240 |
| cgcgcagccg | gcaccgccga | agcctcagcc | cacgacccgg | accccgcctc | agtcccagac | 300 |
| cccgggagcc | ttgccggcga | agcgggagca | gccgccttcc | ctgaccagga | acggcccact | 360 |
| gagctgcggg | cagcggctcc | gcaagagtct | gtcttcgatg | accgcgtcg | ttggcgggct | 420 |
| ggtggcgcta | cgcggggcgc | accctacat | cgccgcgctg | tactgggcc | acagtttctg | 480 |
| cgccggcagc | ctcatcgccc | cctgctgggt | gctgacggcc | gctcactgcc | tgcaggaccg | 540 |
| gcccgcaccc | gaggatctga | cggtggtgct | cggccaggaa | cgccgtaacc | acagctgtga | 600 |
| gccgtgccag | acgttggccg | tgcgctccta | cc | | | 632 |

<210> SEQ ID NO 5
<211> LENGTH: 952
<212> TYPE: DNA
<213> ORGANISM: Homo sapiens
<220> FEATURE:
<221> NAME/KEY: misc_feature
<222> LOCATION: (646)..(646)
<223> OTHER INFORMATION: n is a, c, g, or t

<400> SEQUENCE: 5

| gcttctttcc | acgcccctcc | ggagctcccg | gggaggaagc | tggaacacgg | gattggggtt | 60 |
| cgggagcagg | gggcttcccc | agaacgctgt | ggccaggtct | gagagcgctg | cctctcccct | 120 |
| accctccccg | caggcccgca | cccgaggatc | tgacggtggt | gctcggccag | gaacgccgta | 180 |
| accacagctg | tgagccgtgc | cagacgttgg | ccgtgcgctc | ctaccgcttg | cacgaggcct | 240 |
| tctcgcccgt | cagctaccag | cacgacctgg | gtgcgtgggg | gcgccccgcg | gggacgggaa | 300 |
| gagagcttgg | ggccccggcg | tccccgcctc | acgctcctct | ccgcccgggt | tagctctgtt | 360 |
| gcgccttcag | gaggatgcgg | acggcagctg | cgcgctcctg | tcgccttacg | ttcagccggt | 420 |
| gtgcctgcca | gcggcgccg | cgcgacccte | cgagaccacg | ctctgccagg | tggccggctg | 480 |
| gggccaccag | ttcgagggg | cggaggaata | tgccagcttc | ctgcaggagg | cgcaggtacc | 540 |
| gttcctctcc | ctggagcgct | gctcagcccc | ggacgtgcac | ggatcctcca | tcctccccgg | 600 |
| catgctctgc | gcagggttcc | tcgagggcgg | accgatgcgt | gcaggntgat | tccggaggcc | 660 |
| cgctggtgtg | tgaggaccaa | gctgcagagc | gccggtcacc | tgcaaggcat | caatcagtgg | 720 |
| ggatcgggct | gtggtgaccg | aacgatgcag | gcgttacacc | gatgtggcta | tactggctgg | 780 |
| atccggagcc | accggttcct | gattgtcagg | actcatcttt | cctcctgggg | gatccgcaga | 840 |
| gaaatggtgg | cgctgacagg | cacattgtcc | ccatcccagt | gggcaaccgc | gcagagggcg | 900 |
| gaacacaaag | gctgaagctc | acacaaacac | acccaaacac | cggtctttgg | gc | 952 |

<210> SEQ ID NO 6
<211> LENGTH: 250
<212> TYPE: DNA
<213> ORGANISM: Homo sapiens

<400> SEQUENCE: 6

| | | | | | |
|---|---|---|---|---|---|
| tttttttttgc | tgagaaggaa | agctcttttc | ttcatgggtc | ccgccgggaa | atgccaagac | 60 |
| agaaaagcga | ttcacagctt | ctccacagct | ctcagagaac | aaggtctatg | agatcttaac | 120 |
| gtgcaaaatc | tagatgccag | cccagctaat | gtttactgag | cctaggatac | tgtataccaa | 180 |
| gccctgtgca | aggagaagct | gcatgttatt | ccttatgaga | aactaacatt | tgtttacag | 240 |
| agcagtagtt | | | | | | 250 |

<210> SEQ ID NO 7
<211> LENGTH: 746
<212> TYPE: DNA
<213> ORGANISM: Homo sapiens

<400> SEQUENCE: 7

| | | | | | |
|---|---|---|---|---|---|
| ccgggaagga | gagctctctg | ggggggtctt | taggcccagg | gtggctcact | gcgttccctc | 60 |
| cccaagcctg | ccgcaccaac | ccgtgcctcc | atggggtcg | ctgcctagag | gtggagggcc | 120 |
| accgcctgtg | ccactgcccg | gtgggctaca | ccggacccct | ctgcgacgtg | ggaacccgga | 180 |
| caacgacatc | cgcccgtggt | gcttcgtgct | gaaccgcgac | cggctgagct | gggagtactg | 240 |
| cagacctggc | acagtgccag | accccaaccc | aggcggcgcc | tccgaccccg | tgtcccccta | 300 |
| ggcttcatgt | cccactcatg | cccgcgcagc | cggcaccgcc | gaagcctcag | cccacgaccc | 360 |
| ggaccccgcc | tcagtcccag | accccgggag | ccttgccggc | gaagcgggag | cagccgcctt | 420 |
| ccctgaccag | gaacggccca | ctgagctgcg | ggcagcggct | ccgcaagagt | ctgtcttcga | 480 |
| tgacccgcgt | cgttggcggg | ctggtggcgc | tacgcgggc | gcaccctac | atcgccgcgc | 540 |
| tgtactgggg | ccagagtttc | tgcgccggca | gcctcatcgc | ccctgctgg | gtgctgacgg | 600 |
| cgctcactgc | ctgcaggacc | ggcccgcacc | cgaggatctg | acggtggtgc | tcgggcagga | 660 |
| accgccgtaa | ccacagctgt | gagcccgtgc | cagacgttgg | ccgtgcgctc | ctacgcttgc | 720 |
| acgaggcctt | ctcgccgtca | gtacca | | | | 746 |

<210> SEQ ID NO 8
<211> LENGTH: 13000
<212> TYPE: DNA
<213> ORGANISM: Homo sapiens

<400> SEQUENCE: 8

| | | | | | |
|---|---|---|---|---|---|
| acctgggctt | ggaagtccaa | caccctcact | tctgccatat | tttttttttt | tttgagacag | 60 |
| tccctgtcgc | ccaggctgga | gtgcaatggc | acaatctctg | ctcactacaa | cctccacttc | 120 |
| ctgggttcaa | gcgattctcc | tgcctcagcc | tcacgggtag | ctgggattac | aggcacacgc | 180 |
| cactacgccc | ggctaatttt | tgtattttc | atagagatgg | ggtttggcca | acacgttggc | 240 |
| caggccggtc | ttgaactcct | gacctagagt | gatctgcctg | ccttggcatc | ccaaagtgct | 300 |
| gggattacag | gtgtgagcca | ccacacccag | ccacttctgt | catattctga | tggacacaca | 360 |
| gaacagccct | aactcaatgt | gggaagacac | catacaaggg | catgaatcct | aggtggtgag | 420 |
| gatcaatggg | ggctgtcttt | gaggctgtct | accacagcat | ctttccatcc | ttcctgccct | 480 |
| gtttgctttg | ctttttcctat | gtgtaggctt | cattctcaaa | caggccctcc | ctagagagtg | 540 |
| acaaaggtga | tcatcaatgt | gttcagaccc | acatgctctg | tgcttagtaa | ccccagtgca | 600 |
| acttttttgc | tttcccaaaa | gttctggcaa | agtccaag | ctagcacttt | aattggccta | 660 |
| aattgtgtat | atgcttatct | ctgaaccaat | cactgtggat | tagagatgtc | atgctctgat | 720 |

-continued

```
tgaccagacc taggccacat ctctagccct agctctgagg gtagagttgg cagcactaga      780
gcccatggaa gaagtaagag aggagtcgtt gctaaaggaa aaatcaaagt gtcattaccg      840
aaccaggaca gatgctgggc agcacatgtg cacccgtct tcttctcatg ttccagctgc       900
acatcttagt gccccttggt ttagcacttt tctcattaaa tcatttgctt tcttgcctca      960
cttcctgtgg ttggtagaat gctaagatgg ccccaagatc tctacccctg gtgtttgcac     1020
acctcccagt tattctgtca aacatgaatg tagatgcttc tgtgaaagaa ttttgcacat     1080
gtaatttaag tcccaaattg tttgacctta aataaggag aatggcaggg ccaggcatgg      1140
tggctcatac ctgtaatccc agcactttgg gaggccaagg cgggcagatc acgaggtcag     1200
gagatcgaga ccatcctggc taacacagtg aaaccccatc tctactaaaa atacaaaaaa     1260
ttagctgggc gtggtggcgg gtgcctgtat tccagctac ccaggaggct gaggcaggag      1320
aatggcgtga acccgggagg cgtagcttgc agtgagccaa gatcgtgcca ctgcactcca     1380
gcctgggtga cagagccaga ctctgtctca aaaaaaaaa aaaaaaggag aatggctttg      1440
gtgggcctga cctagtcagg tgagttctta aaaggcgaca catggcccgg tgcagtggct     1500
caggcctgta atcccagcac tttgggaggc cgaggcgggt ggatcacgag gtcaggagat     1560
cgagaccatc ctggctaaca tggtgaaacc ccgtctctac taaaaagaca aaaaattagc     1620
tgggcgtggt ggtgggctcc tgtagtccca gctactcggg aggctgaggc aggagaatgg     1680
cgtgaacccg ggaggcggag cttgcagtga gcggagattg cgccactgca ctccagcctg     1740
ggcgacagag cgagactccg tctcaaaaaa aaaaaaaa aaagaaaat taaaagtggg       1800 tattgttgta agatgctgag tttatggtag tttgttacat gacaatagaa aatgaacaca     1860
cttcacagtg gactccaaga tccccatgat ctttgatctc cttaacctcc tgatctccac     1920
aggacccaga gcataagaat gtcccttctt ctgcttccag tcccactatc tagaaaagag     1980
aggaggagcc cagctcttca tttcaccccc acccacaaac tcccaacttt ccggccctca     2040
aggggtgacc aaggaagttg ctccacttgg ctttccacaa acagcctgtg ccccaccagg     2100
ctcaggaggg cagcttgacc aatctctatt tccaagacct ttggccagtc ctattgatct     2160
ggactcctgg ataggcagct ggaccaacgg acggatgcca tgagggctct gctgctcctg     2220
gggttcctgc tggtgagctt ggagtcaaca cttttcggtga gtgctgtggg aaccaggatt    2280
gtcccaggat tgttctgggg ggtcgctatc acagccatga ccatggcct ctgctcatga      2340 cctgtgggtc caggtgacta ggaggcctat gtggaaaggt gaggccagcc cggaaggccc     2400
aggcagagga gacagacaac cagactgggt ggatacaagg gcacagcctg catttctggg     2460
ggagatgggc cttaagaaga caacgggggg aggtagaaag ggtttgggtc ttgggaagaa     2520
atctctgcat ttctgggctg tgagaggaag ctgcagacta gcaacagatc ggtggcaggc     2580
tatgacttat agtcagttcc ctgccttctt ctctcccttg tagattccac cttgggaagc     2640
ccccaaggag cataagtaca aagctgaaga gcacacagtc ggtaagtggc ctggctcctc     2700
ctcccgggaa cccttgggtg gggatgtgta tggtgcagtg tgtgcagtct cagggcagtc    2760
tagtctagtg cctacctggt gctaggtctt atgcccatgg gcactagagt gatcgtgagc     2820
tgtgtgatcc ttgagggcag ggtatgggct gtgtctaagt gccacgagc ctggctcgga     2880 gcaggtgctt gagatatgtg ctgctggcgc catcacacct gggctcctgc cagccttcct     2940
cagtttcccc agcttctccc cttctttttc tttcccagt acgtctcatg ggcatcattc     3000
atgccacaca gaggccaggg ccttcaatgg gcaaggaagg atcaagagct tgtctctggc     3060
atctgaatgc ctctgaagcc cagctttatc acttatgagc tgggtgactc tgggcgaggg     3120
```

```
atttgagttc tccaagcttc aatttcccct tctgtgaaac caggttgata acagtaaacc   3180
tcttagggtt gttgagaagg gaaacccatg tgaggtattc agcccatcac ctggtgcatg   3240
gaaatgcttt acaaatatta gcttttatta tgaaactacc ttttagatga agggtacctg   3300
ccatttcccc cttcctcaag ctctgccata gctccccatt gctttcattc ttccagacac   3360
taaattacct acatgccagg catggtggct catgcctgta atcccagcac tttgggaggc   3420
caaggtcggt ggatcatgag gtcaggagtt cgagaccagc ctggccaaca tggtgaaatg   3480
ctgtctctac taaaagtaca aaaattagcc aggcatggtg gcatgcgcca gtagtcccag   3540
ctactcggga ggctgaggca gaagaattgc ttgaacctgg gaggtgaagg ttgcagtgaa   3600
cgaagatcac accattgcac tccagcttgg gcaacacagc aagactccgt ctcaaaaaaa   3660
aaaaaaaaat ttacctagag tgtggcacat agcagggcct gtgaaccaga tggaccttac   3720
cctggtgggc ctgacttggt ggggttgagt ctctaagcat ggcgttgagg cccagcacat   3780
tccaaccctg gactccctca gcctcctctc ttcaccccac acccaaaagt ttctcctctc   3840
tcttgcctta cccaaacttg gtgccctatc cttgcctaat cccctgccta aggtccccct   3900
cctctctgtc cgtccatccc atctgcatct tttttttttt ttgagatgga gtctcgctct   3960
gtcccctagg ctagagtgca atggcgcgat cttggctcat gcaacctcc gcctcctggg   4020 ttcaagcgat tctctgcctc agcctcccga gttgctggga ttacaggcac acaacttcat   4080
gctcagctaa ttttttgtatt ttttagtaga cagggtttt caccatgttg gccaggctgg   4140
tctcgaactc ctgccctcag gtggtccgcc caccttagcc tcccaaagtg ctgggattac   4200
aggcgtgagc caccgcgcct ggcccccatt tgcatcttaa aggtccatct cagatccatt   4260
tccatttact gtcctagttc tggttttggtc cttggcaagt gcactttgcc ttgaacaaaa   4320
tagtggcaaa agcttattga gcaggtactt tgtgccagac actgctcagc atttcatggc   4380
attatctcat gaagccccac gacaattcct ctgaagaaga cacaggcaat tctcattatt   4440
cgcgatggtt atgttctata aaatcacagt gaacattgaa ctagcaaaca gtattaggtt   4500
cctgtgagcc tctggtcaca acattttcat caaccaacag catataatct ggttttatgt   4560
atgattctgt ttaaagacat tttatttagt atatgtgttg ctgattcatc aatgctaagc   4620
tgatggcact atagcacaca cctgaatcaa gtgtctaaca cacgctttct ccctaaggta   4680
gccttcttgt gctaggaac tacacagctc ttcagcagga ggctcagagg ccatttccaa   4740
aagccaaatc cccagcaaaa gcacaaagtg tgaaaaacgt tgcactaagt agactgagaa   4800
ggacactcat tcaataggag agctgaaaca agcagcagca gcgtgacgcc ttgttgaacc   4860
ttaactggga atgtgcaaat ttttcactgc tctgtgcatg cccacaaatg gccatgaaaa   4920
catttcaagt attgacttgg gagttacaaa taaaattcag caagtaggca cattctcaat   4980
gtagaaccag agaagaatga ggatcaactg tactattatt actgccgttt tacagataag   5040
gaaaccaagg ctcagatcag agtggttaac agtgacttca acattcaaca agtattatta   5100
agtgcctact ttgtggcaag tgctcttcct ggccttggga ctgaagactt acccaaggtc   5160
acacagctag caggttgtgg agtcaggagt ctactccagc tatctgactc ctgaacccaa   5220
gttttttttt ttttctttaa gatggagtct cactctgtca cccaggctgg agtgcagtgg   5280
cgcgatctcg gctcactgca agctccgcct cccgggttca ccattctc ctgcctcggc   5340 ctcccgagta gctgggacta caggcacctg ccaccacccc cagctaattt ttttgtattt   5400
ttagtagaga ggggggtttca ctgtattagc caggatggtc ttgatctcct gacctcgtga   5460
```

```
tctgcccgcc ttggcctccc aaagtgctgg gattacaggc ttgagccacc gcgcccggcc    5520
ctgaacccaa cttttagagc agaaagtgtt ttcaatgcac agcgaccttt ttgagggtct    5580
gtccttttcc tgaccagacc ctgagggaca gtgcctgagc agttgagtac aggggaagtc    5640
ctcagagagt gtgttgtccc tgcagttctc actgtcaccg gggagccctg ccacttcccc    5700
ttccagtacc accggcagct gtaccacaaa tgtacccaca agggccggcc aggccctcag    5760
ccctggtaag actacgcaga ggagttggag caggggcctg ggagacatgt accctgcctg    5820
tccttctgtc caaggaactc tgcttggaga gaggggactg tgatagggca gggtgggcca    5880
ggcccctggg tagagcaggg aagccttgtc tctttctaca ggtgtgctac cacccccaac    5940
tttgatcagg accagcgatg gggatactgt ttggagccca agaaagtgaa aggtgctaca    6000
cacagcctct ggggtggcct ggggctctct cctcccgcct cattactctc ctggtatcac    6060
cagaccccac acacctggga ttctggaccc agcccttct ctccctccac aatacccttt     6120
ggaagtccag agggagagtt ctgggaagga gtggtcccat tttgcaggtg ggtaaaccaa    6180
gcttggaaac ttggagtagc aaggtcacaa ggcaagtagg ttcaagaagg gccttggccc    6240
ccagctgtgt gactcagctc cctgctcttc cttccaccat gtccatctct cagaccactg    6300
cagcaaacac agccctgcc agaaaggagg gacctgtgtg aacatgccaa gcggccccca     6360
ctgtctctgt ccacaacacc tcactggaaa ccactgccag aaaggtgagg agatgtggag    6420
gacctgggcg gggtgctggg ggacagggc aaccctgggc ctacagaata ggttgctgga    6480
tactcggaga cttggcatgg tcctagactc tcctgagacc actatccctc tttgtcccca    6540
gagaagtgct ttgagcctca gcttctccgg ttttccaca agaatgagat atggtataga     6600
actgagcaag cagctgtggc cagatgccag tgcaagggtc ctgatgccca ctgccagcgg    6660
ctggccagcc aggtgagca gatggttggg aacgggccag ggaggagcgt caggaagaca     6720
ggctggcagg aggccgggtg gtgtgccagg aaggagagct ctctgggggg gtctttaggc    6780
ccaggggtgg ctcactgcgt tccctcccca agcctgccgc accaacccgt gcctccatgg    6840
gggtcgctgc ctagaggtgg agggccaccg cctgtgccac tgcccggtgg gctacaccgg    6900
agccttctgc gacgtgggtg agtgagggtc tggggcaagc agaaggccag cccccaggtg    6960
ggacgggctt gccaggaagg aggagggaga gtgcggaaag cagatgagag ggaggcagga    7020
gagcccagcc ttggctgccc agggagcccc ctttctcctc agacaccaag gcaagctgct    7080
atgatggccg cgggctcagc taccgcggcc tggccaggac cacgctctcg ggtgcgccct    7140
gtcagccgtg ggcctcggag gccacctacc ggaacgtgac tgccgagcaa gcgcggaact    7200
ggggactggg cggccacgcc ttctgccggt gcgccgcgtg gggctgggtg acccctccgc    7260
cccagggctc cgggctcccg gcgctctaac ggcgccccgt cgtgtggcta caggaacccg    7320
gacaacgaca tccgcccgtg gtgcttcgtg ctgaaccgcg accggctgag ctgggagtac    7380
tgcgacctgg cacagtgcca gaccccaacc caggcggcgc ctccgacccc ggtgtcccct    7440
aggcttcatg tcccactcat gcccgcgcag ccggcaccgc cgaagcctca gcccacgacc    7500
cggaccccgc ctcagtccca gaccccggga ggttaggaag tggggggggg aaggaggagc    7560
cgagagggcg ccgggcgagc tagattccgg ccagccggcc gcgggctctc cgtcctcagc    7620
ccctgctcct ccacagcctt gccggcgaag cgggagcagc cgccttccct gaccaggaac    7680
ggcccactga gctgcgggca gcggctccgc aagagtctgt cttcgatgac ccgcgtcgtt    7740
ggcgggctgt tggcgctacg cggggcgcac ccctacatcg ccgcgctgta ctggggccac    7800
agtttctgcg ccggcagcct catcgccccc tgctgggtgc tgacggccgc tcactgcctg    7860
```

```
caggaccggc gagtacccgc ccgcccagag ccgccccagg ggccgcggct cctccgtctc    7920
ccagcgcagc ttccacgctg cacccgaacc cgtgccctac cttctcccgc cccacccttc    7980
tttccacgcc cctccggagc tcccggggag gaagctggaa cacgggattg gggttcggga    8040
gcaggggct tccccagaac gcttgtggcc aggtctgaga gcgctgcctc tccctaccc     8100
cccccgcagg cccgcacccg aggatctgac ggtggtgctc ggccaggaac gccgtaacca    8160
cagctgtgag ccgtgccaga cgttggccgt gcgctcctac cgcttgcacg aggccttctc    8220
gcccgtcagc taccagcacg acctgggtgc gtggggcgc cccgcgggga cgggaagaga    8280
gcttgggcc ccggcgtccc cgcctcacgc tcctctccgc ccgggttagc tctgttgcgc     8340
cttcaggagg atgcggacgg cagctgcgcg ctcctgtcgc cttacgttca gccggtgtgc    8400
ctgccaagcg gcgccgcgcg accctccgag accacgctct gccaggtggc cggctggggc    8460
caccagttcg agggtaggca caactgctag ggcaggggt aggggaggag acctttgatc     8520
actgggttag gcggaagaag cccgcgactt tggtatcgtt ccgggtgcct acagaatggg    8580
tggcgctgac ctgatgggtt gtgagaatgt gtaggtgaat cccaggtaga atcccagggc    8640
ctgggattca ctgctgggat ccccaaatct cctggggata cagggagaat cgaacttgct    8700
cttggttccc tctgggcgcc gggctgcaaa ggccaactag gacgctggcc ccgcgctccg    8760
ggctagtgtg ggagccaggt tctgcgactc tggatgggtg gtgggggagg ggtttctgtt    8820
tccgctccgc ccattcaaat cctggctttt ctctggacct cagcctcctt gcctatgaaa    8880
ttgaattaat ggcacctcct cccctttcggg cttgctgcga gagaggaagg gcatgagtgg    8940
gtttacaagc gcctggagca gctttgtcca tcgtccgggc ggcaagcgtt gtcagatggg    9000
gtgtgaagaa ggcgctctgt gttcgcaggg gcggaggaat atgccagctt cctgcaggag    9060
gcgcaggtac cgttcctctc cctggagcgc tgctcagccc cggacgtgca cggatcctcc    9120
atcctccccg gcatgctctg cgcagggttc ctcgagggcg gcaccgatgc gtgccaggtg    9180
agctcttagc ccggttggcg ccctcccccg aggccgtcag gcacaaatct caggtccaca    9240
gcgctgagct gcgtgtttcc gacccagggt gattccggag gccgctggt gtgtgaggac     9300
caagctgcag agcgccggct caccctgcaa ggcatcatca gctggggatc gggctgtggt    9360
gaccgcaaca agccaggcgt ctacaccgat gtggcctact acctggcctg gatccgggag    9420
cacaccgttt cctgattgct cagggactca tctttccctc cttggtgatt ccgcagtgag    9480
agagtggctg gggcatggaa ggcaagattg tgtcccattc ccccagtgcg gccagctccg    9540
cgccaggatg gcgcaggaac tcaataaagt gctttgaaaa tgctgagaag gaaagctctt    9600
ttcttcatgg gtcccgccgg gaaatgccaa gacagaaaag cgattcacag cttctccaca    9660
gctctcagag aacaaggtct atgagatctt aacgtgcaaa atctagatgc cagcccagct    9720
aatgtttact gagcctagga tactgtatac caagccctgt gcaaggagaa gctgcatgtt    9780
attccttatg agaaactaac attttgttta cagagcagta gttctcagac catacattaa    9840
gatcacttgg ggagcgtttt gagccaatct atgcccaagt tccacctcag accaattaaa    9900
tcagtatgtc tagggatggg gcatgggtag tggtatattt gtaaaactcc ccagataatt    9960
ccatgtacag ccaaggttga aatcgtggt tagaaatact tagcattggc cgggcgcggt    10020
ggctcacgcc tgtaatccta gcactttaag aggccaaggc aggtggattg ctcaggagtt    10080
cgaaaccagc ctgggcaaca cgatgaaacc ccgtctctac taaaatacaa gaaattagcc    10140
gggcacggcg gcgtgcgcct gtagtcccag ctactcagga ggctgaggca ggagaatcac    10200
```

```
ttgaaccggc aggaaggaag gaaggaagga acagagggag ggaaagagag agacagaaag    10260
aaaagaaaaa agaaaataga aaaaaagagc attgactgtg gcgtggaccc taagggctgg    10320
gtgacatatc gttgtcccca ccccaacacg cactagtgta gtgggtctga gagtcccttg    10380
gctagcagta ccatcaccag ggaacttgtt acacataaca aattctcggg ctacacttta    10440
tactgctgaa cagaaagtct ggggtggggc ccagcaatct gtttaacagc cttgcggggg    10500
attctgatgt tctctcatgc ttaagaacca caatctgggg gttgaatggt tggttccctt    10560
acaagtgaag gtctggctgt ccagacacaa catcctttt tcacaaaacc agctttttaa    10620
aattaaaaat agattggcca gatgcggtgg ttcacgcctg taatctcgtc actttgagag    10680
gctgaggcgg gaggattgtt tgagctcaag acttcctgac ccgcctgggc aacatagtga    10740
gacctcatct caaaaaaatt tttttaatt aaaatttgtt tttgcttttt tagagacggg    10800
gcctcgctct gtggctcagg ctggcgtgca gcgacacgat cctataatag tttactataa    10860
tctcgctact gagttcaagc gatccgcccg cctcggcctc ccaaagcgct gggattacag    10920
gagtgagccg ctgcgctctg ccaaacccat cctacaggat aaccttagaa ctgcgacagc    10980
actaaacgcc cacgcccac gtgccccagc ctgggtggtc gctccgggac ggcgccttgt    11040
gtgacgtcac agccccgccc agcctgcctc acagcgccgc aggccttccc cgcgtggcgc    11100
ctctatattt ccccgagagg tgcgaggcgg ctgggcgcac tcggagcgcg atgggcgact    11160
ggaaggtcta catcagtgca gtgctgcggg accagcgcat cgacgacgtg gccatcgtgg    11220
gccatgcgga caacagctgc gtgtgggctt cgcggcccgg gggcctgctg gcggccatct    11280
cgccgcagga ggtgggcgtg ctcacggggc cggacaggca caccttcctg caggcgggcc    11340
tgagcgtggg gggccgccgc tgctgcgtca tccgcgacca cctgctggcc gagggtgacg    11400
gcgtgctgga cgcacgcacc aaggggctgg acgcgcgcgc cgtgtgcgtg ggccgtgcgc    11460
cgcgcgcgct cctggtgcta atgggccgac gcggcgtaca tgggggcatc ctcaacaaga    11520
cggtgcacga actcatacgc gggctgcgca tgcaggcgc ctagccggcc agccaggccg    11580
cccactggta gcgcgggcca aataaactgt gacctgggcg cggctggctc ctcctccact    11640
tgcgcggtgg ggggagttgt aaataaggaa actggtcttt gcaagacggt tacctggtgg    11700
agccgggatt ttgagtctag aggctgccag gcccctgtgc cctacaccct gctctcccat    11760
ggacgccttg cagaggctcc tggcctgact gctgctcctt ggcgcgttcc cagggtccta    11820
gggactccgc agctgaggaa gagtccaagg gtggggctt ctcaaagtct gtttcagcct    11880
tagcgtcctt tctcagagat attcccacac attaggcagg acaagtaaag ggagcccct    11940 ccccatcccg cgaacacctc tccccatcag ggtgtcaggc tggaggccaa tttgctcctc    12000 cccccctccac tcatacctca agcactagca agttgtgagt gggtgacagg atgggcttgg    12060
tggcttgtaa agcagttctg gggctcacag gcctctgcat ctctgcccac attcctccaa    12120
ggggagccta ctgagagggc tcatgtccaa gaccatcgca attgggtttg agacctttaca    12180 tcctgccttc cccaggcctt cgaaaaggcc ccgcaggagt ccctgactga gggaggaa    12240 ctctggcatc cctacccggg agtctcactc tgcaggcctc agtttcaggg tgacctatgg    12300
aggaggggga attgaaaagc ttgggtaagt ttgaggcctg gtttattgcc caaagatagt    12360
ggacaaaagt gggagggagg gtgtctggtc cctgccctcc atgtgctggg gcccagggca    12420
tggcctctct tgcccacccc cacccttccc gtccctctcc ccagcggccc tgatggcaga    12480
ccccacctgt cacttattct ggagccctga tcttatccca gcaggaagga gtgatgtgtg    12540
gctgaggtgg gtgaatttag agggcagagg gagaccagag gaagttcagc caggtggggg    12600
```

```
tcagggggtg ggggtgcaga atcctcctta cacttgcctt gggggtggcc ccaggcctag    12660
gaggggcttc cagggagttt gaattgtggt ttggactcac taaggtaggg ccaggcagat    12720
ggttggggtg agcctgcagg gctggcttct ctggaactgc acctggcctg gcagggcag     12780 gctgctcttg cagccagtct ttgagggag atggtgctgc tgaacccct ggcttggtct      12840 tcccttttgcc attgatggag agcaaaaaga cttccgaatg cctgaggaga gttttaattc   12900
ctttgttttt tttccatcag gcaagtgttg ggaagggaat taattgtggt ggtgccgaag    12960
acctgggtta ggatgaggag atggtatctt ggaggaagga                          13000
```

<210> SEQ ID NO 9
<211> LENGTH: 882
<212> TYPE: DNA
<213> ORGANISM: Mus musculus
<220> FEATURE:
<221> NAME/KEY: misc_feature
<222> LOCATION: (680)..(680)
<223> OTHER INFORMATION: n is a, c, g, or t

<400> SEQUENCE: 9

```
ggctcgagga cactgacacg gaccgaagga gtagaaaact cctgggcagg cagcggggcc      60
atcggcagac gccatgacgg ctctgttgtt cctggggtct ctgctgatga gtctggatct     120
gacactttcg gctccaccat ggaaagactc caagaaattt aaggacgcac ctgatgggcc     180
cacagtggtt ctcactgtgg atgggaggct ctgccatttt ccctttcagt accaccgtca    240
gctacaccac aaatgcatcc acaaaaggcg gccaggctcc cgcccctggt gtgctaccac    300
ccccaacttt gatgaagatc agcaatgggg atactgcttg gagcccaaga agtgaaaga     360 ccattgcagc aaaacacaacc cgtgccacaa aggaggaca tgtatcaaca cccccaatgg    420
gccacactgt ctctgccctg aacacctcac tgggaaacat tgccagaaag agaaaatgct    480
ttgagcctca gcttctcaag ttcttccacg agaatgagct atggtttaga acggggccag    540
gaggtgtggc caggtgcgag tgcaaaggtt ctgaggctca ctgcaagccg gtggccagcc    600
aggcctgcag catcaatccg tgccttaatg ggggcagctg cctcctcgtg gaggaccccc    660
actgtgccgt tgccctacan gctacactgg atattttttgc gacttggacc tttgggcgac   720
ctgctatgaa agcaggggc tcaactacgg gggccggctg ggactaacca atccggtgcc     780
catgtcaccg gtggaacggg gggggccccc tcccggtaca tgacttgaaa accaaccct    840 taactgtggg cctgggccac cacgcatttt tgccggaacc ca                       882
```

<210> SEQ ID NO 10
<211> LENGTH: 1968
<212> TYPE: DNA
<213> ORGANISM: Mus musculus
<220> FEATURE:
<221> NAME/KEY: CDS
<222> LOCATION: (26)..(1819)

<400> SEQUENCE: 10

```
ggcagcgggg ccatcggcag acgcc atg acg gct ctg ttg ttc ctg ggg tct       52
                           Met Thr Ala Leu Leu Phe Leu Gly Ser
                             1               5 ctg ctg atg agt ctg gat ctg aca ctt tcg gct cca cca tgg aaa gac      100
Leu Leu Met Ser Leu Asp Leu Thr Leu Ser Ala Pro Pro Trp Lys Asp
 10              15                  20                  25 tcc aag aaa ttt aag gac gca cct gat ggg ccc aca gtg gtt ctc act      148
Ser Lys Lys Phe Lys Asp Ala Pro Asp Gly Pro Thr Val Val Leu Thr
             30                  35                  40
```

```
gtg gat ggg agg ctc tgc cat ttt ccc ttt cag tac cac cgt cag cta      196
Val Asp Gly Arg Leu Cys His Phe Pro Phe Gln Tyr His Arg Gln Leu
         45                  50                  55 cac cac aaa tgc atc cac aaa agg cgg cca ggc tcc cgc ccc tgg tgt      244
His His Lys Cys Ile His Lys Arg Arg Pro Gly Ser Arg Pro Trp Cys
         60                  65                  70 gct acc acc ccc aac ttt gat gaa gat cag caa tgg gga tac tgc ttg      292
Ala Thr Thr Pro Asn Phe Asp Glu Asp Gln Gln Trp Gly Tyr Cys Leu
         75                  80                  85 gag ccc aag aaa gtg aaa gac cat tgc agc aaa cac aac ccg tgc cac      340
Glu Pro Lys Lys Val Lys Asp His Cys Ser Lys His Asn Pro Cys His
 90                  95                 100                 105 aaa gga ggg aca tgt atc aac acc ccc aat ggg cca cac tgt ctc tgc      388
Lys Gly Gly Thr Cys Ile Asn Thr Pro Asn Gly Pro His Cys Leu Cys
                    110                 115                 120 cct gaa cac ctc act ggg aaa cat tgc cag aaa gag aaa tgc ttt gag      436
Pro Glu His Leu Thr Gly Lys His Cys Gln Lys Glu Lys Cys Phe Glu
                    125                 130                 135 cct cag ctt ctc aag ttc ttc cac gag aat gag cta tgg ttt aga acg      484
Pro Gln Leu Leu Lys Phe Phe His Glu Asn Glu Leu Trp Phe Arg Thr
            140                 145                 150 ggg cca gga ggt gtg gcc agg tgc gag tgc aaa ggt tct gag gct cac      532
Gly Pro Gly Gly Val Ala Arg Cys Glu Cys Lys Gly Ser Glu Ala His
            155                 160                 165 tgc aag ccg gtg gcc agc cag gcc tgc agc atc aat ccg tgc ctt aat      580
Cys Lys Pro Val Ala Ser Gln Ala Cys Ser Ile Asn Pro Cys Leu Asn
170                 175                 180                 185 ggg gga agc tgc ctc ctc gtg gag gac cac cca ctg tgc cgt tgc cct      628
Gly Gly Ser Cys Leu Leu Val Glu Asp His Pro Leu Cys Arg Cys Pro
                    190                 195                 200 aca ggc tac act gga tat ttt tgc gac ttg gac ctt tgg gcg acc tgc      676
Thr Gly Tyr Thr Gly Tyr Phe Cys Asp Leu Asp Leu Trp Ala Thr Cys
                    205                 210                 215 tat gaa ggc agg ggg ctc agc tac cgg ggc cag gct gga act acg caa      724
Tyr Glu Gly Arg Gly Leu Ser Tyr Arg Gly Gln Ala Gly Thr Thr Gln
            220                 225                 230 tcg ggt gcg cca tgt cag cgg tgg acc gtg gag gcc acc tac cgg aac      772
Ser Gly Ala Pro Cys Gln Arg Trp Thr Val Glu Ala Thr Tyr Arg Asn
235                 240                 245 atg act gag aag caa gcg cta agc tgg ggc ctg ggc cac cac gca ttt      820
Met Thr Glu Lys Gln Ala Leu Ser Trp Gly Leu Gly His His Ala Phe
250                 255                 260                 265 tgc cgg aac cca gat aat gac aca cgt cca tgg tgc ttc gtc tgg agt      868
Cys Arg Asn Pro Asp Asn Asp Thr Arg Pro Trp Cys Phe Val Trp Ser
            270                 275                 280 ggc gac agg ctg agc tgg gac tat tgc ggc ctg gag cag tgc cag acg      916
Gly Asp Arg Leu Ser Trp Asp Tyr Cys Gly Leu Glu Gln Cys Gln Thr
            285                 290                 295 cca acg ttt gca cct cta gtt gtc cct gag agt cag gag gag tcc ccg      964
Pro Thr Phe Ala Pro Leu Val Val Pro Glu Ser Gln Glu Glu Ser Pro
            300                 305                 310 tcc cag gca cca tct ctg tcc cat gca cca aat gac tcg acc gat cat     1012
Ser Gln Ala Pro Ser Leu Ser His Ala Pro Asn Asp Ser Thr Asp His
            315                 320                 325 cag act tct ctg tcc aag acc aac acg atg ggc tgc gga cag agg ttc     1060
Gln Thr Ser Leu Ser Lys Thr Asn Thr Met Gly Cys Gly Gln Arg Phe
330                 335                 340                 345
```

```
cgc aag gga ctg tcc tcg ttc atg cgc gtg gtg ggc gga cta gtg gct    1108
Arg Lys Gly Leu Ser Ser Phe Met Arg Val Val Gly Gly Leu Val Ala
            350                 355                 360 ctg cct ggg tcg cac ccc tac atc gct gca ctg tac tgg ggt aac aac    1156
Leu Pro Gly Ser His Pro Tyr Ile Ala Ala Leu Tyr Trp Gly Asn Asn
        365                 370                 375 ttc tgc gcg ggc agt ctc atc gcc ccc tgt tgg gtg ctg acc gcg gct    1204
Phe Cys Ala Gly Ser Leu Ile Ala Pro Cys Trp Val Leu Thr Ala Ala
    380                 385                 390 cac tgc ctg cag aat cgg cca gcg ccc gag gaa ctg aca gtg gta ctt    1252
His Cys Leu Gln Asn Arg Pro Ala Pro Glu Glu Leu Thr Val Val Leu
395                 400                 405 ggt caa gat cgc cac aac cag agc tgc gag tgg tgc cag act ctg gct    1300
Gly Gln Asp Arg His Asn Gln Ser Cys Glu Trp Cys Gln Thr Leu Ala
410                 415                 420                 425 gtg cgc tcc tac cgc ctt cac gag ggc ttc tcc tcc atc acc tac cag    1348
Val Arg Ser Tyr Arg Leu His Glu Gly Phe Ser Ser Ile Thr Tyr Gln
                430                 435                 440 cac gac ttg gct ctg ctg cgc ctg cag gaa agc aaa acc aac agt tgc    1396
His Asp Leu Ala Leu Leu Arg Leu Gln Glu Ser Lys Thr Asn Ser Cys
            445                 450                 455 gcg atc ctg tca cct cac gtt cag cct gtg tgt cta ccc agc ggc gcg    1444
Ala Ile Leu Ser Pro His Val Gln Pro Val Cys Leu Pro Ser Gly Ala
        460                 465                 470 gcc cca ccc tct gag aca gtg ctc tgc gag gtg gcc ggc tgg ggt cac    1492
Ala Pro Pro Ser Glu Thr Val Leu Cys Glu Val Ala Gly Trp Gly His
    475                 480                 485 cag ttc gag ggg gct gaa gaa tac tcc acc ttc ctg cag gag gca cag    1540
Gln Phe Glu Gly Ala Glu Glu Tyr Ser Thr Phe Leu Gln Glu Ala Gln
490                 495                 500                 505 gtt ccc ttt atc gcc ctg gat cgc tgc tcc aac tct aac gtg cac gga    1588
Val Pro Phe Ile Ala Leu Asp Arg Cys Ser Asn Ser Asn Val His Gly
                510                 515                 520 gac gcc att ctc cct ggg atg ctt tgc gct ggc ttc ttg gag gga ggc    1636
Asp Ala Ile Leu Pro Gly Met Leu Cys Ala Gly Phe Leu Glu Gly Gly
            525                 530                 535 acc gat gcc tgc cag ggt gac tcc ggg ggc cct ctg gtg tgt gag gaa    1684
Thr Asp Ala Cys Gln Gly Asp Ser Gly Gly Pro Leu Val Cys Glu Glu
        540                 545                 550 gga act gca gaa cat cag ctc acc ctg cgc gga gtc atc agc tgg ggc    1732
Gly Thr Ala Glu His Gln Leu Thr Leu Arg Gly Val Ile Ser Trp Gly
    555                 560                 565 tcc ggc tgt ggt gac cgc aac aag ccc gga gtc tac aca gac gtg gcc    1780
Ser Gly Cys Gly Asp Arg Asn Lys Pro Gly Val Tyr Thr Asp Val Ala
570                 575                 580                 585 aac tac ctg gct tgg atc cag aag cat att gct tca taa ctaaccagcc    1829
Asn Tyr Leu Ala Trp Ile Gln Lys His Ile Ala Ser
                590                 595 tttatccttc cctccttgtg tgctccttgg gatgggacga tgaatgtggc atgctgggtc    1889
acagtgaagc tagtgccccg acactggggg cacagaaact caataaagtg ctttgaaaac    1949
gttaaaaaaa aaaaaaaaa                                                 1968

<210> SEQ ID NO 11
<211> LENGTH: 1961
<212> TYPE: DNA
<213> ORGANISM: Mus musculus

<400> SEQUENCE: 11
```

| | | |
|---|---|---|
| tcctgggcag gcagcggggc catcggcaga cgcc atg acg gct ctg ttg ttc ctg<br>                                                              Met Thr Ala Leu Leu Phe Leu<br>                                                              1                  5 | 55 |
| ggg tct ctg ctg atg agt ctg gat ctg aca ctt tcg gct cca cca tgg<br>Gly Ser Leu Leu Met Ser Leu Asp Leu Thr Leu Ser Ala Pro Pro Trp<br>          10                         15                      20 | 103 |
| aaa gac tcc aag aaa ttt aag gac gca cct gat ggg ccc aca gtg gtt<br>Lys Asp Ser Lys Lys Phe Lys Asp Ala Pro Asp Gly Pro Thr Val Val<br> 25                         30                      35 | 151 |
| ctc act gtg gat ggg agg ctc tgc cat ttt ccc ttt cag tac cac cgt<br>Leu Thr Val Asp Gly Arg Leu Cys His Phe Pro Phe Gln Tyr His Arg<br>40                       45                      50                      55 | 199 |
| cag cta cac cac aaa tgc atc cac aaa agg cgg cca ggc tcc cgc ccc<br>Gln Leu His His Lys Cys Ile His Lys Arg Arg Pro Gly Ser Arg Pro<br>                  60                      65                      70 | 247 |
| tgg tgt gct acc acc ccc aac ttt gat gaa gat cag caa tgg gga tac<br>Trp Cys Ala Thr Thr Pro Asn Phe Asp Glu Asp Gln Gln Trp Gly Tyr<br>          75                         80                      85 | 295 |
| tgc ttg gag ccc aag aaa gtg aaa gac cat tgc agc aaa cac aac ccg<br>Cys Leu Glu Pro Lys Lys Val Lys Asp His Cys Ser Lys His Asn Pro<br>        90                       95                    100 | 343 |
| tgc cac aaa gga ggg aca tgt atc aac acc ccc aat ggg cca cac tgt<br>Cys His Lys Gly Gly Thr Cys Ile Asn Thr Pro Asn Gly Pro His Cys<br>105                    110                    115 | 391 |
| ctc tgc cct gaa cac ctc act ggg aaa cat tgc cag aaa gag aaa tgc<br>Leu Cys Pro Glu His Leu Thr Gly Lys His Cys Gln Lys Glu Lys Cys<br>120                      125                    130                    135 | 439 |
| ttt gag cct cag ctt ctc aag ttc ttc cac gag aat gag cta tgg ttt<br>Phe Glu Pro Gln Leu Leu Lys Phe Phe His Glu Asn Glu Leu Trp Phe<br>                 140                    145                    150 | 487 |
| aga acg ggg cca gga ggt gtg gcc agg tgc gag tgc aaa ggt tct gag<br>Arg Thr Gly Pro Gly Gly Val Ala Arg Cys Glu Cys Lys Gly Ser Glu<br>                      155                    160                    165 | 535 |
| gct cac tgc aag ccg gtg gcc agc cag gcc tgc agc atc aat ccg tgc<br>Ala His Cys Lys Pro Val Ala Ser Gln Ala Cys Ser Ile Asn Pro Cys<br>                 170                    175                    180 | 583 |
| ctt aat ggg ggc agc tgc ctc ctc gtg gag gac cac cca ctg tgc cgt<br>Leu Asn Gly Gly Ser Cys Leu Leu Val Glu Asp His Pro Leu Cys Arg<br>185                    190                    195 | 631 |
| tgc cct aca ggc tac act gga tat ttt tgc gac ttg gac ctt tgg gcg<br>Cys Pro Thr Gly Tyr Thr Gly Tyr Phe Cys Asp Leu Asp Leu Trp Ala<br>200                    205                    210                    215 | 679 |
| acc tgc tat gaa ggc agg ggg ctc agc tac cgg ggc cag gct gga act<br>Thr Cys Tyr Glu Gly Arg Gly Leu Ser Tyr Arg Gly Gln Ala Gly Thr<br>                    220                    225                    230 | 727 |
| acg caa tcg ggt gcg cca tgt cag cgg tgg acc gtg gag gcc acc tac<br>Thr Gln Ser Gly Ala Pro Cys Gln Arg Trp Thr Val Glu Ala Thr Tyr<br>                 235                    240                    245 | 775 |
| cgg aac atg act gag aag caa gcg cta agc tgg ggc ctg ggc cac cac<br>Arg Asn Met Thr Glu Lys Gln Ala Leu Ser Trp Gly Leu Gly His His<br>                    250                    255                    260 | 823 |
| gca ttt tgc cgg aac cca gat aat gac aca cgt cca tgg tgc ttc gtc<br>Ala Phe Cys Arg Asn Pro Asp Asn Asp Thr Arg Pro Trp Cys Phe Val<br>265                      270                    275 | 871 |
| tgg agt ggc gac agg ctg agc tgg gac tat tgc ggc ctg gag cag tgc<br>Trp Ser Gly Asp Arg Leu Ser Trp Asp Tyr Cys Gly Leu Glu Gln Cys<br>280                      285                    290                    295 | 919 |
| cag acg cca acg ttt gca cct cta gtt gtc cct gag agt cag gag gag<br>Gln Thr Pro Thr Phe Ala Pro Leu Val Val Pro Glu Ser Gln Glu Glu<br>                    300                    305                    310 | 967 |

| | | |
|---|---|---|
| tcc ccg tcc cag gca cca tct ctg tcc cat gca cca aat gac tcg acc<br>Ser Pro Ser Gln Ala Pro Ser Leu Ser His Ala Pro Asn Asp Ser Thr<br>                315                    320                    325 | 1015 |
| gat cat cag act tct ctg tcc aag acc aac acg atg ggc tgc gga cag<br>Asp His Gln Thr Ser Leu Ser Lys Thr Asn Thr Met Gly Cys Gly Gln<br>    330                    335                    340 | 1063 |
| agg ttc cgc aag gga ctg tcc tcg ttc atg cgc gtg gtg ggc gga cta<br>Arg Phe Arg Lys Gly Leu Ser Ser Phe Met Arg Val Val Gly Gly Leu<br>345                    350                    355 | 1111 |
| gtg gct ctg cct ggg tcg cac ccc tac atc gct gca ctg tac tgg ggt<br>Val Ala Leu Pro Gly Ser His Pro Tyr Ile Ala Ala Leu Tyr Trp Gly<br>360                    365                    370                    375 | 1159 |
| aac aac ttc tgc gcg ggc agt ctc atc gcc ccc tgt tgg gtg ctg acc<br>Asn Asn Phe Cys Ala Gly Ser Leu Ile Ala Pro Cys Trp Val Leu Thr<br>                380                    385                    390 | 1207 |
| gcg gct cac tgc ctg cag aat cgg cca gcg ccc gag gaa ctg aca gtg<br>Ala Ala His Cys Leu Gln Asn Arg Pro Ala Pro Glu Glu Leu Thr Val<br>    395                    400                    405 | 1255 |
| gta ctt ggt caa gat cgc cac aac cag agc tgc gag tgg tgc cag act<br>Val Leu Gly Gln Asp Arg His Asn Gln Ser Cys Glu Trp Cys Gln Thr<br>410                    415                    420 | 1303 |
| ctg gct gtg cgc tcc tac cgc ctt cac gag ggc ttc tcc tcc atc acc<br>Leu Ala Val Arg Ser Tyr Arg Leu His Glu Gly Phe Ser Ser Ile Thr<br>425                    430                    435 | 1351 |
| tac cag cac gac ttg gct ctg ctg cgc ctg cag gaa agc aaa acc aac<br>Tyr Gln His Asp Leu Ala Leu Leu Arg Leu Gln Glu Ser Lys Thr Asn<br>440                    445                    450                    455 | 1399 |
| agt tgc gcg atc ctg tca cct cac gtt cag cct gtg tgt cta ccc agc<br>Ser Cys Ala Ile Leu Ser Pro His Val Gln Pro Val Cys Leu Pro Ser<br>                460                    465                    470 | 1447 |
| ggc gcg gcc cca ccc tct gag aca gtg ctc tgc gag gtg gcc ggc tgg<br>Gly Ala Ala Pro Pro Ser Glu Thr Val Leu Cys Glu Val Ala Gly Trp<br>                    475                    480                    485 | 1495 |
| ggt cac cag ttc gag ggg gct gaa gaa tac tcc acc ttc ctg cag gag<br>Gly His Gln Phe Glu Gly Ala Glu Glu Tyr Ser Thr Phe Leu Gln Glu<br>        490                    495                    500 | 1543 |
| gca cag gtt ccc ttt atc gcc ctg gat cgc tgc tcc aac tct aac gtg<br>Ala Gln Val Pro Phe Ile Ala Leu Asp Arg Cys Ser Asn Ser Asn Val<br>505                    510                    515 | 1591 |
| cac gga gac gcc att ctc cct ggg atg ctt tgc gct ggc ttc ttg gag<br>His Gly Asp Ala Ile Leu Pro Gly Met Leu Cys Ala Gly Phe Leu Glu<br>520                    525                    530                    535 | 1639 |
| gga ggc acc gat gcc tgc cag ggt gac tcc ggg ggc cct ctg gtg tgt<br>Gly Gly Thr Asp Ala Cys Gln Gly Asp Ser Gly Gly Pro Leu Val Cys<br>                540                    545                    550 | 1687 |
| gag gaa gga act gca gaa cat cag ctc acc ctg cgc gga gtc atc agc<br>Glu Glu Gly Thr Ala Glu His Gln Leu Thr Leu Arg Gly Val Ile Ser<br>    555                    560                    565 | 1735 |
| tgg ggc tcc ggc tgt ggt gac cgc aac aag ccc gga gtc tac aca gac<br>Trp Gly Ser Gly Cys Gly Asp Arg Asn Lys Pro Gly Val Tyr Thr Asp<br>570                    575                    580 | 1783 |
| gtg gcc aac tac ctg gct tgg atc cag aag cat att gct tca taa<br>Val Ala Asn Tyr Leu Ala Trp Ile Gln Lys His Ile Ala Ser<br>585                    590                    595 | 1828 |
| ctaaccaggc tttatccttc cctccttgtg tgctccttgg gatgggacga tgaatgtggc | 1888 |
| atgctgggtc acagtgaagc tagtgccccg acactggggg cacagaaact caataaagtg | 1948 |
| ctttgaaaac gtt | 1961 |

<210> SEQ ID NO 12
<211> LENGTH: 478
<212> TYPE: DNA
<213> ORGANISM: Mus musculus

<400> SEQUENCE: 12

| | | | | | | |
|---|---|---|---|---|---|---|
| cggcagacgc | catgacggct | ctgttgttcc | tggggtctct | gctgatgagt | ctggatctga | 60 |
| cactttcggc | tccaccatgg | aaagactcca | agaaatttaa | ggacgcacct | gatgggccca | 120 |
| cagtggggc | tgaagaatac | tccaccttcc | tgcaggaggc | acaggttccc | tttatcgccc | 180 |
| tggatcgctg | ctccaactct | aacgtgcacg | gagacgccat | tctccctggg | atgctttgcg | 240 |
| ctggcttctt | gtagggaggc | accgatgcct | gccaggtga | ctccggggc | cctctggtgt | 300 |
| gtgaggaagg | aactgcagaa | catcagctca | ccctgcgcgg | agtcatcagc | tgggctccg | 360 |
| gctgtggtga | ccgcaacaag | cccggagtct | acacagacgt | ggccaactac | ctggcttgga | 420 |
| tccagaagca | tattgcttca | taactaacca | ggctttatcc | ttccctcctt | gtgtgctc | 478 |

<210> SEQ ID NO 13
<211> LENGTH: 849
<212> TYPE: DNA
<213> ORGANISM: Mus musculus

<400> SEQUENCE: 13

| | | | | | | |
|---|---|---|---|---|---|---|
| ggccaatctt | ctggaggcat | ctcttcgggt | gaggttcctt | ccccccctag | atgactcttg | 60 |
| agtgcgtcaa | attgacagac | agtaacccag | cacaaggatt | acagggagac | ttgaactgtc | 120 |
| ttgtgcttct | tttgggctcc | aaattataaa | ggcttaacca | ggactttgtc | ccatgctgg | 180 |
| agcaatggag | acaatggaga | gaactattct | gggagccagg | ttctgagcca | ctgtgtggaa | 240 |
| gaggatagga | agtgcttcct | gtgttttaag | ccctgctctt | ctctgggctt | cagtgtcctt | 300 |
| gccatgaaat | acttattggc | aggtccctat | cactcaggct | tgctgtgagg | gagcaaagcg | 360 |
| gagtaggtgg | ggaattgtct | ggtagcctgg | cccacgcagc | aagctcaggt | cctcccctct | 420 |
| gatttgcagg | ggctgaagaa | tactccacct | tcctgcagga | ggcacaggtt | ccctttatcg | 480 |
| ccctggatcg | ctgctccaac | tctaacgtgc | acggagacgc | cattctccct | gggatgcttt | 540 |
| gcgctggctt | cttggaggga | ggcaccgatg | cctgccaggt | cagccctggg | gtcctggtag | 600 |
| gtaccttggt | ccctgcctgt | caagcataag | gcaagaacca | cgtgctgcct | gttccccacc | 660 |
| caggttgact | ccgggggccc | tctggtgtgt | gaggaaggaa | ctgcagaaca | tcagtcaccc | 720 |
| tgcgcggagt | catcagctgg | ggctccggtg | tgttgaccgc | aacaagcccg | gagtctacac | 780 |
| cagacgttgg | caataactgg | ttggatccac | gaagcatatt | ggtcataact | taacaggtta | 840 |
| ttcttcctc | | | | | | 849 |

<210> SEQ ID NO 14
<211> LENGTH: 12001
<212> TYPE: DNA
<213> ORGANISM: Mus musculus

<400> SEQUENCE: 14

| | | | | | | |
|---|---|---|---|---|---|---|
| tgaactaaga | aggtaccact | ggcaactctg | gaagcccagg | agggagggag | ggagggaggg | 60 |
| aggaagggag | ggagggaggg | aggaagggag | ggagggaggg | agggagggag | ggagggaggg | 120 |
| agggagggag | ggttggttcc | tactgagcaa | aataaatgct | gggtagaaaa | agccacagtg | 180 |
| tcctgctccc | cacctctgc | ccagcacttc | agctgtaaga | caaggcaatg | ccctttgatt | 240 |
| tagcacttca | ctctggaaag | agtacaattc | tgagatgaca | gcgagatcat | catccctgtg | 300 |

```
tatttctgcc tgctcccagt gacccaagtt gaccgtgatt gaggttattt tgtaaaatat    360
ttccttgagg caccgggaat caaggccatg catcctaggc gagcattctg ccactgagtc    420
tcatgcttcc accgaggagc cacatcccca gtccttttgt aagagaattt gccgatgtag    480
gtggccatgg tggcacagga aattagggag gctgaagcag gcaggagaat cacaattaag    540
tcaacctgag aaacatagtg tctccagagg aaagaatttt gcaactgtga ttaagggccc    600
atattgagtc tggctacaca gccctgacta accagaactc actgtgtaga cagctggctg    660
gcctcgaact catacagacc tacctgcctt tgcatcatgg cagtaaaatc atgtaccgcc    720
atggactctc actctgtggg agtatccttg atgggcctga cccaatcgga tgagccctga    780
aaagggacca gaagtttcct ggcaaagcag acacagtgtg aagcaattca atgcagggac    840
attctctgct ccaccctctg ttttattgct tttaattctt aaaattaatt tatttattct    900
atgtacaatg ttttccctca tgcatgccca tgcaccatgt gcatgcctga tacctgcaga    960
gtccagaaga ggcaatcaga acccctggaa ttggagttat agacagctct gagccctcct    1020
gtaggtagat gggaatagag cctggatcct ttggatctaa agtccatacc tgctgagcga    1080
cacctccagc cctgacactg gctttaaagt tagaggaagt aggtggccag aaatgtagaa    1140
atcacacgta gccgtggtcg acagctgaga agaagctggg acatctgtcc tgcagccaca    1200
tggaagtgag ttctgaccag gacctggggg gggatctcac tttagaggct ccagagactt    1260
cagcttgaac ctcagcgttc tgatgatctg gcagaaaact ctaactatgc agcaccaagt    1320
gtttacccat gggtctgtgc atccgtaaaa gtagttttgg ggggcattgt tttagggtgc    1380
tcagagtgtg gtaattggtc acacagcaga aggaagctgc atgaaggaag gtcacataag    1440
cattctgtaa gattctgaaa gcaggttttg tcccatcatt cttaccttac cctcaacagg    1500
acctggaaca ccatcctagt aaagtcagga aaatggaggg caggaaccta actcttcagt    1560
ccgctactcc caccagtgac tccctgctca aaacacttct acagcgctgt tctgctgggt    1620
ctcccatgaa gcccttgctc ctcagaccca ggagcaagct tgaccaatct ctacctctga    1680
agcttctgag acctttgccc gcatctattg atcctcactc ctgggcaggc agcggggcca    1740
tcggcagacg ccatgacggc tctgttgttc ctggggtctc tgctgatgag tctggatctg    1800
acactttcgg tgaggacggt ggacactggg attgagccag agtggcagtg aggggtccct    1860
gttccggatt tagcctctgc ctgtcacctg ctagttcagg tgactgagag acttgtggtg    1920
ggggtggggg ttgggggaag gcacagctag cccagaagat ccaaacaaag gaggtagcag    1980
cccatgctgg tggatgtgag gacacaggct acttttgtgg gggagtcaat gagaagagaa    2040
aggaaggcta cactttgtga ggaaatcctg tactttggcg aggtggcagg aggttgaggc    2100
ctataggatc aagggaagtc taacattgtg ggcaatgttc ctgccttctc tctcctatag    2160
gctccaccat ggaaagactc caagaaattt aaggacgcac ctgatgggcc cacagtgggt    2220
aagtgatctg gcctcttttc ctaatctact ctgtggggat ggctgtgctt tagcctgcgt    2280
ggtctcaggc tctggagca aggagggatc ctgagccaag ctgttccgtt gacatttaaa    2340
cctgggtgcc tacagattca gatgtgtgcc cggagtgcca ggcttgggct gtcctggatg    2400
cctgtgttag agcctggcag gtactctgta gtgttggaga tgatgtcatc tgatgatgtc    2460
atcacacctg cacaccaaca agtgctcgcc agtttcccca tcttcctccc tttcctttca    2520
acactcctgg agaatgtcag acataaccgg tagagttcag agcttcagtg ggcgatggga    2580
gccagaacag agctttagac tcaccccaaga tcacagacac cccaagttgt ctccaaaccc    2640
```

```
taactttctc acttgtgagt ttactctctg cttcattttt ccctgtctga aaagttagac    2700
gggttgctga ggagaaaggg ttcctcattg ttgtagatgc tgctgccagg aaaatgccct    2760
aacatgttag ctcttaggct agggcatagc tcactggcag agcacttgcc caacatgcac    2820
gcacacacac ctgggtttgg tctgcagcac tgtgagggga aaaaattcct ttttttttta    2880
attttaaaga aaaaattctt tcttaagctg gagagataac tcagaggtta agagcactgg    2940
ctgctcttcc agaggtcctg agttcaattc ccaacaacca catggtggct cacaaccatc    3000
tatctgtact gggatctgat gccttttcct ggtctgtctg aagacagcaa cacatatagt    3060
aaataattaa ttaattaaag aaagaacaat tcttttttaa agatttattt atttattta    3120 tgtatgagtg ttctatctgc atgtacacct gtatgccaga agagggtatc agatctcatt    3180
acagatagct gtgagccacc atgtggttgc tgggagttga actcaggacc tctacaagaa    3240
cagacagtag atctcaaatg ctgagccatt tttccagccc aagaaaaaaa atcttaactt    3300
ttagtaaatt tgacttaggt gaagggttcc accccatcc tgccccaaac cctgctatag    3360
gacttgtgag tacagaactc taccacagtg agccttgtct gtgggtcaa gctgaggctt    3420 gtagtgtgat gtctctcact gaagcccaac tcagtgtgac cctccaggct tctgtcctaa    3480
ccactctaag ccaatcagct gctgtccctt tcaacctgac ccaccatggc ccctgtctc    3540 caagttctag gacccttccc tctctctatc accctgttgc taaattgcca ctaaaaggag    3600
aaaagaagaa gaagaagaag aagaagaaga agaagaagaa gaagaagaag aagaagaaga    3660
ggaagaaaca aaacacattt gttgagcacc tactgagtcc tggactcaat gtcccaagca    3720
ttgccactaa gcctcacggt gttcccctga agtagacagt gatttctttt tcattttctc    3780
tttgagatta taatataatt acatcactgg gcagtggtgg cacatgcctt taatcctagc    3840
acttgggagg cagaggcagg cagatttctg agttcgaggc cagcctgctc tacacagtga    3900
gttccaggac agccagggct acacagagaa accctgtctc gaaacaaaa acaatatata    3960 tatatatata tatatatata tatatataca catatatatg tgtgtgtgtg tgtgtatacg    4020
tatatatata tatacacata tatatataca catatatata tacatatata taatcatatc    4080
atccccctcc ctttcttccc tccaaacccct cccatagccc caataattat ttcttttttt    4140
ttttaagatt tatttattta ttatatgtaa gtacactgta gctgtcctca gatactccag    4200
aagagggcat cagattttgt tacgatggt tgtgagccac catgtggttg ctgggatttg    4260
aactcgggac cttcggaaga gcagtcggcg ctcttaacca ctgagccatc tcgccagccc    4320
caataattat ttcttatgat taactatact tttctcagct accatgaaca tcaagttcac    4380
aaattcagtg attccgttca caaattaggt tccgtgagcc tctggctatg acattttcac    4440
caatcattag catgtaatct tgttacatct ggattctgtt taaagacatt attcagtgtg    4500
catgttgttg atcccttaaa cactaatcta atggccgatg ccactattac tgcctgcctg    4560
acaaggtgtc cctgacacgt tttcttcata aggcgcatac aacttcttgt gttcttgcaa    4620
gtaggagcct caggtaacac ttgggcatac acatagaacc actctgtctc cctgaagtac    4680
tgaggatcga acctagagcc ttgtgtatgc caggcaaatg cttggccact gagttaaaac    4740
tctggccctc tttaaaaaga agtgtgtgtg tatgtgtgtg tgcaagtgca tgtgtgtatg    4800
tgtatgtaca tatgtgtgtg tgtttgtgtg tgtgtatgtg tgtatatgtg tgcgtgtgtg    4860
tgtgcaagta catgtgtgtg tatgtgtgtg tgttcgagca tctttcactg acccattcaa    4920
ttccataaag atcatgaagg cactgtgaac gttggcagtt tctttggctt tctttggcct    4980
tgtgctgact tgtgagcaag cactacacga ctgacctata tcctcagcct gagtcacaag    5040
```

```
tattgggttg gagggggctt acaaataaat gtttacaaag caggcagggg cagtggtggg    5100
ggggtgcctt taatcccagc acttggcagg cagaggcagg tgaatttctg agtttgaggc    5160
cagcctggtc tacacagtga gttccaggac agccagggct acacaaagaa accctgtctt    5220
gggggtgggg gtgggggaac aaaacaaaaa acaaaacaaa acaaagcagg caggttcaca    5280
aatataaagt cagtgaggat tggcagttgc attactgttg ccagtttact aagccaaaaa    5340
tggccaaggg acctaagtgt ttgtttgttt gtttgtttgt ttgtttgttt gtttgtttgt    5400
tttgtagaca ggctatctct gtgtaataga cctggctgtc ctggaactca ttctgtagac    5460
caggctggcc ttgaactcac agagatccgc ctgcctcagc ctcccaaatt ctgggatgaa    5520
aggcgtgtga cctaaatctt taatgagctc aactttgtga catgcacctg tgtttcagac    5580
ttgctcaggg tcagatatct attccagctg tctgactcta gaagcctact ttctaagcag    5640
gatgcagtct tgaatgcata gctgaccttt ttccaaatca ggccctgtga ggcagagggt    5700
gggcagctgg gtctcaggc agggctctga ggtgtggtgt tcctacagtt ctcactgtgg    5760
atgggaggct ctgccatttt cccttcagt accaccgtca gctacaccac aaatgcatcc    5820
acaaaaggcg gccaggctcc cgcccctggt aagacatttt ctaataggggg ttggggggagg    5880
gggctggatg aaatggactc tgtctagcta tctaagcatc gtgtttggtc aaaaggtgtg    5940
tgtgtgtgtg tgtgtgtgtg tgtgtgtgtg tttgtgtgtg tgtgtgaagc aaggctagcc    6000
tagccagcct caggcactgc agggaaacct catctatccc ccaggtgtgc taccacccc    6060
aactttgatg aagatcagca atggggatac tgcttggagc ccaagaaagt gaaaggtatg    6120
tatggcatgc aggccccggg tggctcaagg ctgtgtgtgt cttgctgctc actccgttcc    6180
cacacaccta ctcacctact aagcatcatc agatgccaaa cacttgggat tctgggcccc    6240
gcccttttcc ttctcttaca gcattctttc aaaagtcaga ggaagaattc tggggaaaga    6300
ggccaccatt gtccagatga gcttgagggt ctagaagctt ggggttctat ggtttgatga    6360
caagcaggtg caggcagggt attggtccct acatatgtcc ttccgactcc ggaagtgctt    6420
cgctcttgtt atctacctct cagaccattg cagcaaacac aacccgtgcc acaaaggagg    6480
gacatgtatc aacaccccca atgggccaca ctgtctctgc cctgaacacc tcactgggaa    6540
acattgccag aaaggtaaga ggaactgcct cccagcaaga tgtccctgga gacccggtgc    6600
tttgccatgg tcccattgac ttccttgtgt ccccagagaa atgctttgag cctcagcttc    6660
tcaagttctt ccacgagaat gagctatggt ttagaacggg gccaggaggt gtggccaggt    6720
gcgagtgcaa aggttctgag gctcactgca agccggtggc cagccagggt aagtgggtgt    6780
gcagggactg tggggaggag ggcagagagt caggaacccc tggtagaagg ctgggtgcaa    6840
tgatgtacac aggtaaggct cagtttgcac ctctccccac cccaccccca gcctgcagca    6900
tcaatccgtg ccttaatggg ggcagctgcc tcctcgtgga ggaccaccca ctgtgccgtt    6960
gccctacagg ctacactgga tatttttgcg acttgggtga gtaagacccc gtgtggaaag    7020
gcttgcggag gtggatagag agaatggaag tgaaccagag ggctccaaca gactcatccg    7080
ccgactgcag ggagccatct ctctttctct agacctttgg gcgacctgct atgaaggcag    7140
ggggctcagc taccggggcc aggctggaac tacgcaatcg gtgcgccat gtcagcggtg    7200
gaccgtggag gccacctacc ggaacatgac tgagaagcaa gcgctaagct ggggcctggg    7260
ccaccacgca ttttgccggt tcgcgagaag ggaccgggca ggggaacttg ctttctctta    7320
gggtcctcga gggcctcccc acgttctaac agtgctccct cttgagattg caggaaccca    7380
```

```
gataatgaca cacgtccatg gtgcttcgtc tggagtggcg acaggctgag ctgggactat    7440
tgcggcctgg agcagtgcca gacgccaacg tttgcacctc tagttgtccc tgagagtcag    7500
gaggagtccc cgtcccaggc accatctctg tcccatgcac caaatggtta ggcagaggag    7560
ggggtcccgg cgcagaggac atgggtctct cttattcctg gcagcccgtg ccaggtatcc    7620
atggcctcag ccagtctctc cttccacaga ctcgaccgat catcagactt ctctgtccaa    7680
gaccaacacg atgggctgcg acagaggtt ccgcaaggga ctgtcctcgt tcatgcgcgt     7740
ggtgggcgga ctagtggctc tgcctgggtc gcacccctac atcgctgcac tgtactgggg    7800
taacaacttc tgcgcgggca gtctcatcgc cccctgttgg gtgctgaccg cggctcactg    7860
cctgcagaat cggcaagtgc caccctcggt gacccctag accgctccta ccgtacccgc     7920
accctactct ttccctgccc gccattcttg agctccctcg aggggttgga aactaaggca    7980
cccccagagc atttgtagcc ggtctgagcc tgctgcctgt cccccacccg actgcaggcc    8040
agcgcccgag gaactgacag tggtacttgg tcaagatcgc acaaccaga gctgcgagtg      8100
gtgccagact ctggctgtgc gctcctaccg ccttcacgag ggcttctcct ccatcaccta    8160
ccagcacgac ttgggtgggg tggccctaca gggataggga gaaggatgg cggagggctg      8220
gggccctatg tcgccatcta acctttgcct ctcggggtag ctctgctgcg cctgcaggaa    8280
agcaaaacca acagttgcgc gatcctgtca cctcacgttc agcctgtgtg tctacccagc    8340
ggcgcggccc caccctctga acagtgctc tgcgaggtgg ccggctgggg tcaccagttc      8400
gagggtaggc acaactgttg ggcgctggtt ggagactttt ggttatctag gagcgcagtt    8460
ggtacgcccc gatgaatctg ggggacaagt ttcactgaca tgacagttgt aaaaaacgca    8520
cagagccctt gtctctgtag cgtgactttc ccagattcta gaattctctg tcgagattcc    8580
agagcccctt gaggtttgtt ctagtttttt gccttctatt gtggcgttaa acaccatgac    8640
caaatccagc ttaggcagga aaggttttat ttggcttccg aggttgcagg gtttcttgct    8700
gtccaccatt gaggaagcca caacagggag tggaggcagg aactgaggca ggaaacggaa    8760
agggacactc cttgctgcct ttctcttcat ggcttgttca gctttctttt taaaaaattc    8820
acttatttt attttatgtg catgtgagtc tgcctacaag catatgtgtg caccatatgt     8880
acatctggta caggggaagc cagatctgta atacaggtta aaaaccacgg tgtggggct      8940
gggaacggaa ccaaggccct ctgcaagaac agcaagagct cttaacctct gagctagccc    9000
ccaacacctt gcggcttgct tactttgctt tgcttttctc ttttcctctt cctcttcctc    9060
ttcctcttcc tcctcctcct ctttctcccc ctcttcctct tgttttgttt ttgttttttg    9120
ttttgaaggc agggtttctc tgtgtagtcc cagctgtccg ggagctgtcc aggagctgtc    9180
cagctctgta gaccaggctg ccttcaacct taagcactcc atctgccttt gcctcccaag    9240
tgctgggatt aaaggcttgc acctttctgg ctcagtttct ttcttacaca atccaggccc    9300
acctgttcag ggcggcatca ctcacagtgg gcggggccct ttcacatcaa ccattaatca    9360
agaaaatgcc cggggctggt gagatggctc agtgggtaag agcacccgac tgctcttccg    9420
aaggtccaga gttcaaatcc cagcaaccac atggtggctc acaaccatct gtaacgagat    9480
ctggcgcctt cttctggagt gtctgaagac agctacagtg tacttacata taattaataa    9540
ataaatcttt aaaaaaaaaa aaaagaaaa tgccctacag atattgccct aggccaatct     9600
tctggaggca tctcttcggg tgaggttcct tccccccta gatgactctt gagtgcgtca      9660
aattgacaga cagtaaccca gcacaaggat tacagggaga cttgaactgt cttgtgcttc    9720
ttttgggctc caaattataa aggcttaacc aggactttgt ccccatgctg gagcaatgga    9780
```

```
gacaatggag agaactattc tgggagccag gttctgagcc actgtgtgga agaggatagg   9840
aagtgcttcc tgtgttttaa gccctgctct tctctgggct tcagtgtcct tgccatgaaa   9900
tacttattgg caggtcccta tcactcaggc ttgctgtgag ggagcaaagc ggagtaggtg   9960
gggaattgtc tggtagcctg gcccacgcag caagctcagg tcctcccctc tgatttgcag  10020
gggctgaaga atactccacc ttcctgcagg aggcacaggt tccctttatc gccctggatc  10080
gctgctccaa ctctaacgtg cacggagacg ccattctccc tgggatgctt tgcgctggct  10140
tcttggaggg aggcaccgat gcctgccagg tcagccctgg ggtcctggta ggtaccttgg  10200
tccctgcctg tcaagcataa ggcaagaacc acgtgctgcc tgttcCccac ccagggtgac  10260
tccgggggcc ctctggtgtg tgaggaagga actgcagaac atcagctcac cctgcgcgga  10320
gtcatcagct ggggctccgg ctgtggtgac cgcaacaagc ccggagtcta cacagacgtg  10380
gccaactacc tggcttggat ccagaagcat attgcttcat aactaaccag gctttatcct  10440
tccctccttg tgtgctcctt gggatggac gatgaatgtg gcatgctggg tcacagtgaa   10500
gctagtgccc cgacactggg ggcacagaaa ctcaataaag tgctttgaaa acgttcctca  10560
gaattctgtc ttgaaacgtc aagtgggagc acaggtaagc caactccctc gttgcctgga  10620
caaggcaact agccagatgt cagcataaga ggcgtagact cttgtccgga ccaccatatt  10680
ttctcatcct tactttgggt gagcttttgc cgcccatgtt caagtccacc tgaggtcaat  10740
taactggact ctagggagaa ggcagtcttg gcatattttt aaaacgctac gggtgattcc  10800
ttatgcaata gaggttggga actgtagtta agagtgttcc agacgggaat cgtggtgcgg  10860
atagtagctg ctgagcatgt gtgagaggcc ctgggttaga tcccagcacc accattaaaa  10920
gaagggggag gggttgtgtt gggttgtgtg ggttttgttt gtttgttttg aactttaagc  10980
ctggcatggt ggtgcaagtt ggtgtcaagg aaaatctgag gctgcatctg atgcctctaa  11040
gtacaagctg ggttaggagc cagccagcca gagccttcgg ggatgcggtg actccaaagc  11100
gaggtttgta gttcccttgc aggagaggag cctagttgtc cagatgagta catttcttgc  11160
ttttaaaaat gtccttctgt ttattgattt attgagatat ctgtcgtcct aatgccgaaa  11220
ttataggcct atacaatcac ccagtttatg tggtgcaggg ggatcaatcc caaaactttg  11280
ttcttggtct agccaggccc tctgtcaact gcactgtact gactgcgcta cactcccgt   11340
ccttacaccc atctttgcac agcatcttac tgcatagctt ttgtctggcc tgtgacttgc  11400
taggtagcct tgaacttgta cagatcccct tgcttcatga gtgacaggtt taagtacaag  11460
ccaccatgtc tggctttttt ttttttttt aattaagaaa aaaaatggg gctggtgaga  11520
tggctcagtg ggtaagagca cccaactgct cttctgaagg tctggagttc aaatcccagc  11580
aaccacatgt tggctcacaa ccatccgtaa tgagatctga tgccctcttc tggagcgtct  11640
gaagacagct acagtgtact tacatgtaat aaataaataa ataaataaat aaatcttaaa  11700
aaaaaaaga aaaaatgtg gtttgtgtta tgagtgtgtc acagtgtggt gtgaaggtca  11760
gagcacaact ctgtggagcc agttctctcc ttctgccttt gtgggggctc tggtgataaa  11820
actcaggcca ccaggcttat aagacaatgc accctactg tctgagcctt tttttttttt  11880
ttttatggtt tttcgagaca ggcttctctc tgtgtagccct ggctgtcctg gaactcactt  11940
tgtagaccag gctggcctcg aactcagaaa tccgcccgcc tctgcctcct gaatgctggg  12000
a                                                                 12001
```

<210> SEQ ID NO 15

<211> LENGTH: 2128
<212> TYPE: DNA
<213> ORGANISM: Rattus norvegicus

<400> SEQUENCE: 15

```
caggaaccca tctcggtact ctgcttccac cagccttgcc ctgctcacga gggttcgacg      60
gcgctgttct tctgggcttt ctgtgaagtc tgtgctcctc aggcccagga gggagcttaa     120
ccaatctcca cctctgaggt ttctgagacc tttgcccaca tctattgatc cttactctgg     180
```

| ggc agg cag c tgg gcc att g cgg acg cc atg acg gct ctg ttg ttc ctg ggg | 233 |
|---|---|
| Met Thr Ala Leu Leu Phe Leu Gly | |
| 1               5 | |

| tct ctg ctg atg agt ctg gac ttg aca ctt tcg gcg cca ccg tgg aag | 281 |
|---|---|
| Ser Leu Leu Met Ser Leu Asp Leu Thr Leu Ser Ala Pro Pro Trp Lys | |
| 10              15              20 | |

| tcc aag gag ttc aag gac gga gct ggc gat ccc tct gtg gtt ctc act | 329 |
|---|---|
| Ser Lys Glu Phe Lys Asp Gly Ala Gly Asp Pro Ser Val Val Leu Thr | |
| 25              30              35              40 | |

| gtg gac ggg aag ctc tgc cac ttt ccc ttt cag tac cac cgt cgc ctg | 377 |
|---|---|
| Val Asp Gly Lys Leu Cys His Phe Pro Phe Gln Tyr His Arg Arg Leu | |
|             45              50              55 | |

| tac cac aaa tgc atc cac aaa gga cag cca ggc tcc agg ccc tgg tgt | 425 |
|---|---|
| Tyr His Lys Cys Ile His Lys Gly Gln Pro Gly Ser Arg Pro Trp Cys | |
|     60              65              70 | |

| gct acc acc ccc aac ttt gac gag gac cag caa tgg gga tac tgc ttg | 473 |
|---|---|
| Ala Thr Thr Pro Asn Phe Asp Glu Asp Gln Gln Trp Gly Tyr Cys Leu | |
|     75              80              85 | |

| gag ccc aag aaa gtg aaa gac cat tgc agc aaa cac agc ccc tgc cac | 521 |
|---|---|
| Glu Pro Lys Lys Val Lys Asp His Cys Ser Lys His Ser Pro Cys His | |
| 90              95              100 | |

| aaa gga ggg acg tgt gtc aac acc ccc aac ggc ccg cac tgt ctc tgc | 569 |
|---|---|
| Lys Gly Gly Thr Cys Val Asn Thr Pro Asn Gly Pro His Cys Leu Cys | |
| 105             110             115             120 | |

| cct gaa cac ctc acc ggg aaa cat tgc cag aga gag aaa tgc ttt gag | 617 |
|---|---|
| Pro Glu His Leu Thr Gly Lys His Cys Gln Arg Glu Lys Cys Phe Glu | |
|             125             130             135 | |

| tct cag ctc ctc aag ttc ttc cat gag aat gag ata tgg ttt aga act | 665 |
|---|---|
| Ser Gln Leu Leu Lys Phe Phe His Glu Asn Glu Ile Trp Phe Arg Thr | |
|     140             145             150 | |

| ggg cca gga ggt gtg gcc agg tgc cag tgc aaa ggt cct cag gct gtt | 713 |
|---|---|
| Gly Pro Gly Gly Val Ala Arg Cys Gln Cys Lys Gly Pro Gln Ala Val | |
|     155             160             165 | |

| tgc aag ctg ctg acc agt cag gtt tgc agg gtc aat ccg tgc ctt aat | 761 |
|---|---|
| Cys Lys Leu Leu Thr Ser Gln Val Cys Arg Val Asn Pro Cys Leu Asn | |
| 170             175             180 | |

| gga ggc acc tgc ctc ctc gtg gag gac cac cga ctg tgc cac tgc cct | 809 |
|---|---|
| Gly Gly Thr Cys Leu Leu Val Glu Asp His Arg Leu Cys His Cys Pro | |
| 185             190             195             200 | |

| gca ggc tat gcc gga cct ttt tgc gac tta gac ctt aag gcg act tgc | 857 |
|---|---|
| Ala Gly Tyr Ala Gly Pro Phe Cys Asp Leu Asp Leu Lys Ala Thr Cys | |
|             205             210             215 | |

| tac gaa gac agg ggt ctc agc tac cgg ggc cag gct aaa act act ctg | 905 |
|---|---|
| Tyr Glu Asp Arg Gly Leu Ser Tyr Arg Gly Gln Ala Lys Thr Thr Leu | |
|     220             225             230 | |

| tcg ggt gca cca tgt cag cgg tgg gcc tcg gag gcc acc tac cgg aac | 953 |
|---|---|
| Ser Gly Ala Pro Cys Gln Arg Trp Ala Ser Glu Ala Thr Tyr Arg Asn | |
|     235             240             245 | |

| atg act gag acg caa gct cta agc tgg ggc ctg ggc cac cac gca ttc | 1001 |
|---|---|
| Met Thr Glu Thr Gln Ala Leu Ser Trp Gly Leu Gly His His Ala Phe | |
| 250             255             260 | |

```
tgc cgg aac cca gat aat gac aca cgt cca tgg tgc tac gtc tgg agt         1049
Cys Arg Asn Pro Asp Asn Asp Thr Arg Pro Trp Cys Tyr Val Trp Ser
265                 270                 275                 280 ggc gac agg ctg agc tgg gac tac tgc gac ctg gaa cag tgc cag atg         1097
Gly Asp Arg Leu Ser Trp Asp Tyr Cys Asp Leu Glu Gln Cys Gln Met
                285                 290                 295 cca acg ctc aca tct ccg gtt tcc cct gag agt cac gac atg ctg aag         1145
Pro Thr Leu Thr Ser Pro Val Ser Pro Glu Ser His Asp Met Leu Lys
300                 305                 310 ccc cgg cct ccc ata ttg cag atg cct cag ttc ccg tct ctg tcc gat         1193
Pro Arg Pro Pro Ile Leu Gln Met Pro Gln Phe Pro Ser Leu Ser Asp
            315                 320                 325 gca cta gac aac tcg acc cgt aat cag aat gtt gtg tcc agg acc agt         1241
Ala Leu Asp Asn Ser Thr Arg Asn Gln Asn Val Val Ser Arg Thr Ser
330                 335                 340 acg gtg gtc tgc gga cag agg ttt cgc aag cga ctg tcc tcg ctc agg         1289
Thr Val Val Cys Gly Gln Arg Phe Arg Lys Arg Leu Ser Ser Leu Arg
345                 350                 355                 360 cgc gtg gtg ggc gga cta gtg gct ctg cct gga tcg cat ccc tac atc         1337
Arg Val Val Gly Gly Leu Val Ala Leu Pro Gly Ser His Pro Tyr Ile
                365                 370                 375 gct gca ctg tac tgg ggc gac agc ttc tgc gca ggt agt ctc atc gac         1385
Ala Ala Leu Tyr Trp Gly Asp Ser Phe Cys Ala Gly Ser Leu Ile Asp
            380                 385                 390 ccc tgc tgg gtg ctg acc gct gct cac tgc ttg cag aaa cgg cca gcg         1433
Pro Cys Trp Val Leu Thr Ala Ala His Cys Leu Gln Lys Arg Pro Ala
        395                 400                 405 ccc gag gaa ctg aca gtg gta ctt ggt caa gat cgc cat aac cag agc         1481
Pro Glu Glu Leu Thr Val Val Leu Gly Gln Asp Arg His Asn Gln Ser
410                 415                 420 tgc gag agg tgc cag act ctg gct gtg cac tcc tac cgc ctt cac gag         1529
Cys Glu Arg Cys Gln Thr Leu Ala Val His Ser Tyr Arg Leu His Glu
425                 430                 435                 440 ggc ttc tct tcc aaa acc tac cag cat gat ttg gct ctg ctg cgc ctg         1577
Gly Phe Ser Ser Lys Thr Tyr Gln His Asp Leu Ala Leu Leu Arg Leu
                445                 450                 455 cgg ggg agg aaa aac agc tgc gcg atc ttg tcg cct cat gtc cag ccg         1625
Arg Gly Arg Lys Asn Ser Cys Ala Ile Leu Ser Pro His Val Gln Pro
            460                 465                 470 gtg tgt ctg ccc agc agc gcg gcc cca ccc tct gag aca gtg ctc tgc         1673
Val Cys Leu Pro Ser Ser Ala Ala Pro Pro Ser Glu Thr Val Leu Cys
        475                 480                 485 gag gtg gcc ggc tgg ggt cat cag ttc gag ggg gct gaa gaa tac gcc         1721
Glu Val Ala Gly Trp Gly His Gln Phe Glu Gly Ala Glu Glu Tyr Ala
490                 495                 500 acc ttt ctg cag gag gca cag gta ccc ttc atc tcc ctg gat cgc tgc         1769
Thr Phe Leu Gln Glu Ala Gln Val Pro Phe Ile Ser Leu Asp Arg Cys
505                 510                 515                 520 tcc agc tct aac gtg cac gga gac gcc atc ctg cct ggg atg ctt tgt         1817
Ser Ser Ser Asn Val His Gly Asp Ala Ile Leu Pro Gly Met Leu Cys
                525                 530                 535 gct ggc ttc ttg gag gga ggc gcc gat gcc tgt cag ggt gac tcc ggg         1865
Ala Gly Phe Leu Glu Gly Gly Ala Asp Ala Cys Gln Gly Asp Ser Gly
            540                 545                 550 ggt cct ctg gta tgt gat gaa gga gtt aca gag cgt cag ctc acc ctg         1913
Gly Pro Leu Val Cys Asp Glu Gly Val Thr Glu Arg Gln Leu Thr Leu
        555                 560                 565
```

```
cga gga gtc atc agc tgg ggc tcc ggc tgt ggt gac cgg aac aag ccc      1961
Arg Gly Val Ile Ser Trp Gly Ser Gly Cys Gly Asp Arg Asn Lys Pro
        570                 575                 580 ggg gtc tac act gac gtg gcc aat tac ctg gat tgg atc cag gag cat      2009
Gly Val Tyr Thr Asp Val Ala Asn Tyr Leu Asp Trp Ile Gln Glu His
585                 590                 595                 600 act gct ttc taa gtaaccaggg tcggtccttg cgaagctagt ggctgggccc          2061
Thr Ala Phe cagggacaca gaaactcaat aaagtgcttt gaaaacgtta aaaaaaaaaa aaaaaaaaa     2121 aaaaaaa                                                              2128

<210> SEQ ID NO 16
<211> LENGTH: 14000
<212> TYPE: DNA
<213> ORGANISM: Rattus norvegicus
<220> FEATURE:
<221> NAME/KEY: misc_feature
<222> LOCATION: (1)..(153)
<223> OTHER INFORMATION: n is a, c, g, or t
<220> FEATURE:
<221> NAME/KEY: misc_feature
<222> LOCATION: (10493)..(10542)
<223> OTHER INFORMATION: n is a, c, g, or t

<400> SEQUENCE: 16
nnnnnnnnnn nnnnnnnnnn nnnnnnnnnn nnnnnnnnnn nnnnnnnnnn nnnnnnnnnn     60
nnnnnnnnnn nnnnnnnnnn nnnnnnnnnn nnnnnnnnnn nnnnnnnnnn nnnnnnnnnn    120
nnnnnnnnnn nnnnnnnnnn nnnnnnnnnn nnntaggtag gagaggaagg aggttagagg    180 ggaaagggc ccagacatct ttcagccaac aagatagact atttcctgct aatgagggac     240
attgggttct tggggcaaac aagaggagca gcaaccttcc ctgggccctc ttggggccct    300
cccatttata ccctctccag agtccacgga atcaaactat ctgtaactga caaaactcac    360 accccgtgcta gtgcacgagg caattcacaa tcacctcctg caaagcagcc tctatgttac   420
atgaaataaa aacatatcca cataccataa agtgggtttt taaagaatcc aaaattctca    480
ctacaagggt accagtgaca ggctaaaaaa aaaaaaaaaa aaaaaagatt gagccaagtc    540 taattattg aaccaataag tttgctgaag ttgcttatag gcatacgtgt aagggtcac      600 ttacaggagc atgagtgact caaaggcagc tacatttcca taaaggctgc tccagcatgg    660
ggatgactca gagaagccac atgactagag ctcctggcat ggcttgaaag cagtttgact    720
gtttggagag tagcctctct ctccagcaat tgtttgttgc tttgtaacc ttgaaaacaa     780 aactttataa atcttgtaat tttcaggatc ttcctgggct tcctaagtgt actttttaag    840
tcttaggaat acttccttgt agaggacaca tgtgtagtag acccacattg aacttagagg    900
aatcctacct tacctctgcc ttctgaacac tgtgtttaaa ggaatgtgcc accatgttca    960
gctcatgcta agcctcttgt attgaccaat gactggtttc tactttccct ggggctcagg   1020
agtggacaat gacagatggt agccccgcc cctaaatgc ccaggagtat ccaccattgg     1080
tccatggtat gttatagctt tgagggaaa ggtatcctga tagtaaccaa gggacatcgt    1140
aatgtcatac tcacacaaga gatttattgg gagagataca agaggcagc tgcctctcct    1200 cagtggagaa gcagcaggga atggagcaag ttttatgcag ggttttttgg ggatggagtt   1260
ttccagggca gagatgtcta ggaagggat tggtgggatt ttgagctcag gaattggtgg    1320
taagttttcc aaccctgacg tgatcgtgca tgtgtagggt aaaagctgca catgcagctc    1380
atgatccaac gcctgcttcc cacatggaga cctgtgctca ccacagtcct cctctgactg   1440
```

```
gctgaattta ggctcccgca taaccttgaa gcccttccct cgctttccta ctgtaaaacc      1500
ctctgtgctt gccatggtga tgcacttcta cagttcctac aattaggagg tggagtcagg      1560
gaaatcgcgc agttaggcca gcccagatca agtccctctc tcaaaagcaa acaaagaaa       1620 caaaccacac cctctattgc gcaagcaaac cagttcctct tccctagagt atcggccctc      1680
cccaggagga ggtggtcata gggtcaggtc ctgaggccaa gatctgtgct ggtataatct      1740
ggaactgata gggttctttc actttggtca actctactgc atggctcagt cttgcttttg      1800
tgacagttaa tgttatgatg acagctaact ttatgtctga agttaaaa tgtctgtgct       1860 taagaaaact atgaagcaaa attagacttc caaatgtgaa gggctgttaa ggcttagatt      1920
gtttttaact gctattttgg attctataaa caagcttgtt ttgctccaga ggaccctctg      1980
cttgcgccag aacaaatcgt aactttgtat tctttgcctt tataaagccc tgactgaggt      2040
ggctgggcgc tgcgacaggg agtcccaaat tgcaaatgta gacctggaag cactatctgc      2100 ataaagcct cttcttaacc ctaaccctaa catggtcaga ctggcgagtc tctgaatgac        2160
cccagatcca taacacctgc attatgtcct agtggcggtc accaaaagtt ccttttgaaa      2220 ccaaagttg aataagtgcc ccgttcctcc ggccttctgc ttgcgaagct gaccacagcc       2280
ttcctccctt cccgcagaat caggaacctg ttaccttctg ccttcgttgt ctataaaatg      2340
aaatcacctc tgaggatttt ccatcctccc ttccctgttt gcttggcttt ttcttctcag      2400
actgtcctga tcagcaacag atgcccacta accatcccag actctaatcg gggcggggcc      2460
tggtggcgca cgcctttaat ccctgcattc aggagacaga ggaaagccta ttcctgagtt      2520
gtggtcttga gatgccgaga tgccgtgctc tgattggctc ttgaactgag agggtgccac      2580
gctagcaact atggaagcac aggagggaga gagcgaagga gagagggttc ctatcgagcg      2640
aaatgaatgc tgggtagaaa aagccacagt gcccctaatc ccatctttct cccagctctg      2700
cggctgcaag gcaatgccct ttgatttagc atgttgctct ggaatgaata caattctgag      2760
atgacacgga gatccccatt cccacgtatt tcccctgct cccagtgacc caagttaacc        2820
gtcattgagg ttattttcta gaatattatc ttgaggtgcc aggaatcgag cccatgcaag      2880
ctagactaga attcttccac tgaggagtct catcccctgt cctttgtaa gagaattttg       2940 ccgatgtagt tggccatcat gacacatgat attaaatatt aaggaggctg aagcaagcgg      3000
gagaatccca attaaaggtc agtctgagaa acaatcagaa ggaaaagaat ttgcaaatgt      3060
aattaagggc ctatactggg tctcaataca cagtccttac tagtttggaa ctcactatgt      3120
agaccaggct ggccttgaac tcatagagac ccacctgctt ctgcgtcctg ggactaaagg      3180
tacagctcgt accaccgtgt actcccatgg gagtatcctt gatgggtctg aactaatcag      3240
atgagccctg aaaagggacc agaatttttcc cggcaaagca gagacacagt gtgaagcaat     3300
tcaacccggg aacattctct gctccgggct ctgttttctt gtttgtagtt tttcatatta      3360
atttgtccta tgtacagtgt tcggcctgca tccatgccta tacatcatgt ataggtgcct      3420
gctgcctgcg gaggccagaa gagggcatca gatcccctgg agctggagac aagcagacag      3480
ttctgagtca tcatgcaggc agacaggaat agaacctgga tctaagtgtc cgtcaccgct      3540
gagccacccc tccaaccctg acactggttt taaagttaga ggaagcagat gaccagaaat      3600
gtaggaatca catgtagctg tggtcgacag ctaagaagaa tctgggacat ctgtcctgca      3660
gccatatgga aatgacttct gatgggact gttgagagac ctcggtctga accttaggtt       3720
tctgagggtc tggacagaaa ctctaactat gcagcaccaa gtgtttaacc catgggtctg      3780
cgcgcccgta acattgtttt aggggggaca ttgtttagg gtgctcagag tgtggtaatt       3840
```

```
ggtcattcag cagattgaag ccagaaggct tcccgatagt ctgcaagatt ttgtaagcag    3900
gcttttcttc agccattctt accttaccct caacaggacc tggaacacca tcttagtaaa    3960
atcaatgccc tactgctcag gagagggga gggcaggaac ccatctcggt actctgcttc     4020
caccagcctt gccctgctca cgagggttcg acggcgctgt tcttctgggc tttctgtgaa    4080
gtctgtgctc ctcaggccca ggagggagct taaccaatct ccacctctga ggtttctgag    4140
acctttgccc acatctattg atccttactc tggggcaggc agctgggcca ttggcggacg    4200
ccatgacggc tctgttgttc ctggggtctc tgctgatgag tctggacttg acactttcgg    4260
tgaggactgt agacactggg acacttaaac cagagtgaca gtgcaggggt ggtggggtgg    4320
tggtggtgtc cctgttccag ctttggcctt tgcctgttgc ctgctagttc aggtgaccga    4380
gagacgtgtg ggggaaggca cagctggccc agaaggcccc acaaaggaga tagcagctca    4440
tgctggtgga tatgagaacg caggctacat tgtggggga gacaatgaga agagagagga    4500
aggccacgtc ttgtgaggaa atcctgtact ttggggaggc ggcagcaggt tgaggcctaa    4560
tacaggatca aggaaagttt gacattgtgg gcaatgtccc tgccttctct ctcctgcagg    4620
cgccaccgtg gaagtccaag gagttcaagg acggagctgg cgatccctct gtgggtatgt    4680
gacctggctt ttcctaatct actctgtggg gatgaatgtg ctctaccctg catggcctcc    4740
gcacggcctc aggcctccga agcagaggag ggattctgag caaagctgtt ccagtcatgt    4800
tcagacctgg gtgcctacag atccagatga tagcagatcc agatgtgtgc ctggagggca    4860
gggcgtgggc tctcccggat gcccacatta gagtctggca ggtacacggt agtgtgggac    4920
aatactactg atgatgtcat cacatctgca caccaagtct tcctcagttt ccctaccttc    4980
ctccttttcc tgtcagcaca tctggagaat gtcagacatc ccctgttcag accctcagtg    5040
ggtgatggga gacagaacag agcgtcaggc tcgcccaaga tcacaggcac cgaaatgtct    5100
ccaaaccctc gctttctcgc ttgcgagttt cctctcagct tcacttttc ccctcactgt     5160 aaaactcaac gggttgtgga ggagaaatga gtttctaatc cttggaaaga gctttaccta    5220
ggtgctgctg cccccaaatg ccttaaagct ttagctctta gactaggact gtagctcaca    5280
acacacgcac acacaacacg cacacacgcc tgggtttggt ctgcagcacc atgggaaaat    5340 tcctttttt ttttaattgt aaagaaaaaa attcctgggc tggagagacg gctcagcagt     5400
taagagcatt gactgctctt ccagaggtcc tgagttcaat tcccaacaac cacgtggtgg    5460
ctcacaacca tctgtaatgg ggtctgatgc cctcttctgg tgtctgaaga caactacagt    5520
gtactcacac acataaagta aataaataaa ttaattaatt aattaattaa ttaaaggttt    5580
tagaaagaaa ggaaggaagg aagaattttg tttaaagatt tatttatttt atgtatatga    5640
gtacactgtt gctctcttaa cacataccag aaagggcat cgaatcccac tacagatggc     5700
tgtgagccac cacgtgattg ctgggaattg aactcaggac ctctggaaga gcagtcagtg    5760 cttttaacc actgagccat ctctccagcc caagaattct tttttttttt ttcttttctt     5820 ttttcggag ctggggaccg aacccagggc cttgtgcttg ctaggcaagc gctctaccac     5880
tgagctaaat ccccaacccc cagcccaaga attcttaaac aaggtgtccc tgacacattt    5940
tcttcatgag gcacacatgg cttccttgtgg tcttgcaggt aggagcccca ggtaacactt    6000
gagcaaacac agagaaccac tcttcccctt tctccctgaa gcacgggggg gtcaaaccta    6060
gagcctggtg tatgccaggc aaatgcttgg ccactgagct gaaccgtggc cctcttaaa     6120 aagaagtgtg cttgtgtggg gtgtgtgtgt gtgtgtgtgt gtgtgtgtgt gtgtgtgtgc    6180
```

```
gcgcgcgcgt gtgtgtgttt gagcatcttt cactgatcca cacaattcca cagagacatt      6240
gcaagcattg gcattttctt tggcttcctt ttacctgtgg catcttgtca gcaaacacta      6300
cactactgac ctatatcctc aacctgaatc acaagcattg ggttaggggg gtttacaaat      6360
aaacgtttac aaagcaggca gatttgcaaa tgtaaagcca gtgaatgatg aggcttggca      6420
gttgggttac tgttgccagt ttactaaacc aaaaatggtt aagagtccta ataagtagg       6480 tgtgtgtgta ctggggtttg gggaaaggga gacaggcttt ctctgtgaaa aagccctggc      6540
tgacctggat ctcattctgt ggaccaggct ggccttgaac tcacagagat ccacctgcct      6600
ctgcctccca agttctggga tgaaaggcca gtgacctaaa tatttaataa gtgcaacttt      6660
gtaacaggca cctgggtttc atttgctcag ggtcagggaa ctaagtgttg gaatcagaca      6720
accattccag ttgtctgact ctagaaaccg actttctaag caggatgcgg cctggaatgc      6780
ctagctgtcc tttttcaagc caggcagggt aaggcagcgc ttgggcaact ggacctcagg      6840
gcaggattca gaggtgtgtg ctgttcctac agttctcact gtggacggga agctctgcca      6900
cttttccttt cagtaccacc gtcgcctgta ccacaaatgc atccacaaag gacagccagg      6960
ctccaggccc tggtaagaac ttgtaatagg ggttggggga ggggcctggc tgtctgagaa      7020
tcaatcgtgt ttgggcaaaa gggatgtgtg tgtgtgtgtg tgtgtgtgtg tgtgtgtgtg      7080
tgtgtgtgtg agtgtgtcga agcagggcta gcctagccag cctcaggcag tgcagagaaa      7140
cctcatctct tccccaggtg tgctaccacc cccaactttg acgaggacca gcaatgggga      7200
tactgcttgg agcccaagaa agtgaaaggt atggcatgca ggccccgggt gactcaagac      7260
tgtgtgtgcc ctgctcctca ctccactcgg ttcccacaca ccttctcggg tgccacacac      7320
acacttggga ttcctggccc agccccttcc cttctcctac agagtccttt caaaagtcag      7380
agggagaatt ctgggggaag aggccaccct tgtccagatg agtttaattt aaggtctaga      7440
agcttggggt gccagggttc tatgacaagc aggttcaggc aaggcattag tgtcacttgg      7500
actctgggta cttctttctt tttttttttt aaactccccc cccctggtt ttttttttt       7560 tttttttttt tttttttttt tttttttttt tggagctggg gactgaaccc agggccttgc      7620
gcttgctagg caagcgctct accactgagc taaatcccca accctgggt acttcttct        7680 tgaatcctct ctcagaccat tgcagcaaac acagccctg ccacaaagga gggacgtgtg       7740
tcaacacccc caacggcccg cactgtctct gccctgaaca cctcaccggg aaacattgcc      7800
agagaggtaa gaggaactgc ctcccaggag gaagtccctg gagctttggc ggggtcccac      7860
ttgcttcctt ttgtccccag agaaatgctt tgagtctcag ctcctcaagt tcttccatga      7920
gaatgagata tggtttagaa ctgggccagg aggtgtggcc aggtgccagt gcaaaggtcc      7980
tcaggctgtt tgcaagctgc tgaccagtca gggtaagtgg gtgtgtactc ccgggatggt      8040
ggggaagagg gcagcaagtc aggagcccct ggttgatgta cccagggagg gctcagtttg      8100
caccttcccc ctagtttgca gggtcaatcc gtgccttaat ggaggcacct gcctcctcgt      8160
ggaggaccac cgactgtgcc actgccctgc aggctatgcc ggacctttt gcgacttagg      8220 tgagtaggac cccatgtggg aaaggctttc ggagatggat agagagaatg gaaaagtgaa      8280
ccagagggca ccaacagacc catccctga ctgcagggag ccctctctct ctctctagac       8340
cttaaggcga cttgctacga agacaggggt ctcagctacc ggggccaggc taaaactact      8400
ctgtcgggtg caccatgtca gcggtgggcc tcggaggcca cctaccggaa catgactgag      8460
acgcaagctc taagctgggg cctggccac acgcattct gccggttcgc agggaaggga       8520
caaggcaggg caactcgctt cccttaggg tcctcggggg tccccgtgct ctaacagtgc       8580
```

```
tccctcttga gactgcagga acccagataa tgacacacgt ccatggtgct acgtctggag    8640
tggcgacagg ctgagctggg actactgcga cctggaacag tgccagatgc caacgctcac    8700
atctccggtt tccccctgaga gtcacgacat gctgaagccc cggcctccca tattgcagat    8760
gcctcagttc ccgtctctgt ccgatgcact agacagttag gcggaggagg ggtcccggcg    8820
cagaggacat gggtctcttt tattctaggc agcccgaggt aggtatccgt ggcctcagcc    8880
aatctctcct tccacagact cgacccgtaa tcagaatgtt gtgtccagga ccagtacggt    8940
ggtctgcgga cagaggtttc gcaagcgact gtcctcgctc aggcgcgtgg tgggcggact    9000
agtggctctg cctggatcgc atccctacat cgctgcactg tactggggcg acagcttctg    9060
cgcaggcagt ctcatcgacc cctgctgggt gctgaccgct gctcactgct tgcagaaacg    9120
gcaagcgcca ccctcgggga cccctaatct gctcctaccc tacctgcacc ctactcttcc    9180
ccccatcccc gctattcttg agctccctca aggggttgaa acaggggcg ccccaaaaac     9240
atttgtagcc agtctgaaca cactgtcctc cacccgaccg caggccagcg cccgaggaac    9300
tgacagtggt acttggtcaa gatcgccata accagagctg cgagaggtgc cagactctgg    9360
ctgtgcactc ctaccgcctt cacgagggct tctcttccaa aacctaccag catgatttgg    9420
gtggggtagc cctacaggga tagggagaaa ggatggggag ggttgggggc ctatgtcgcc    9480
atctaaccct tttctcttgg ggtagctctg ctgcgcctgc gggggaggaa aaacagctgc    9540
gcgatcttgt cgcctcatgt ccagccggtg tgtctgccca gcagcgcggc cccaccctct    9600
gagacagtgc tctgcgaggt ggccggctgg ggtcatcagt tcgagggtag gcacaaatgt    9660
tgggggctga ttggagactt ggttatcttg agcctggggg acatgttcca ctgacatgac    9720
agttgtaaaa aaacaaaaaa caaaaaacca ccaccacaac aaacaacaac aaaactcttc    9780
tctgtagagt gattttccca gaatctagaa ttctttgtct ggattccctt gagatttgtt    9840
ctagtttgcc ttctcttcag gcggtctccc attcaagtac taaccaggct ggaccctgct    9900
tagtttccaa catcagacga gaggcaggaa aggctttatt tgacttccaa ggttgctgtc    9960
caccattggg gaaccacag caggaactga ggcgggacat gggaagggac acccccttgct   10020
gcctttctct tcatggctta ttcagctttc tttttaaaat tcatttttt atcttatgtg    10080
catgtgtggc tgcctacatg tctgtgtaag tgccatatgt acaccttgta taggggaagc    10140
cagatcgtta tataggttaa aactgctggg aactgaactc aggtcctctg caagaacagc    10200
aagtgctctt aacctctgag ttatccccaa cacctcggct gggttgtttt ctcttcctcc    10260
tcttcctcct cctcctcctc ttccccctcc cctcctcct cttcctcctc ctcctcctct    10320
tcctcctcct cttcctcttc ctcctcctct tcctcttccc cctcttcctc tttctcctcc    10380
tcctcctcct cttcctcctc ctcttccccc tcctcctcct cctcttcctc tttcctctct    10440
tcctcttcct cctcctcctc ctcctcctcc tcctcctcat catcctcctc ctnnnnnnn    10500
nnnnnnnnn nnnnnnnnnn nnnnnnnnnn nnnnnnnnn nntcctcctc ctcttcctct    10560
ttctcctctt cctcttcctc ctcctcctcc tcctcctctt cctcctcctc ttcctcttcc    10620
tcatcttctt cctcttcctc ctcctcttcc tcttcctcct cctcctcttc ctcttcctcc    10680
tcctcttcct cctcttcctc ctcttcctcc tcctcttcct cttcctcctc ttcctcctct    10740
tcctcctctt cctcctcctc ttcctcctcc tcctcttcct cttcctcctc cttttctttg    10800
tttttggctt ttaagaaacg gtttctctgt gtagtcccag ctgtctagga gctgtccagc    10860
tctgtagacc aggctgccct tgaaatccac ctgcctttgc ctcccaagtg ctaggataaa    10920
```

```
aggcttgcac ttttctggct ccgctttctt tctcatacaa ccaggcccac cttttgaggg    10980
tgactccacc cacagtgggc tgggccccct cacatcaacc gttagtcaag aaaatgcctc    11040
gaagacattg ccctaggcca atcttctgga ggcatctcct caggttgagg gttccttcct    11100
cccagatgat actgggtcct gtcgaattga cagacagaaa ccagcacagg attacagaga    11160
gacttgaact ttcttgtgct tctttggggc tccaaattat aaaggcttaa ccaggacttt    11220
gtctccatgc tggagcaatg gagacaatag ggagaactat tctgggagcc aggttctgag    11280
acactgtgtg ggagaggata agaggtgctt cctgtgtttt aatcctagct ctttctggg     11340 ctccagtgtc cttgtcatga acttcttatt ggcaggtccc tatccctcgg acttgctgtg    11400
agggcgtaaa gggtaggtgg ggaattgtct ggtagcctaa cccacaaagc aaactcaggt    11460
cctcccccac cctctgatct gcaggggctg aagaatacgc cacctttctg caggaggcac    11520
aggtacccct catctccctg atcgctgct ccagctctaa cgtgcacgga gacgccatcc     11580
tgcctgggat gctttgtgct ggcttcttgg agggaggcgc cgatgcctgt caggtcagcc    11640
ctggggtcct ggttggtacc ttgcccctct gcctgtcaac catagggcaa gagccatgtg    11700
ctgcctgttc cccacccagg gtgactccgg gggtcctctg gtatgtgatg aaggagttac    11760
agagcgtcag ctcaccctgc gaggagtcat cagctggggc tccggctgtg gtgaccggaa    11820
caagcccggg gtctacactg acgtggccaa ttacctggat tggatccagg agcatactgc    11880
tttctaagta accagggtcg gtccttgcga agctagtggc tgggcccag ggacacagaa      11940 actcaataaa gtgctttgaa acgttcctc agaattccgt ctcagaacac caagtgggag      12000
cacagatgcg ccaactccct ccatgcctgg acaaggcagc tggccagatc tcagcacaag    12060
aggcttagac tcttcttgtc caggccacca tgttttcaca gacttactct gtgccaagga    12120
ggtcgtgcag attgctcacc agacacgccc attctatgtt tacgaagtag cagggtctca    12180
gcctggactg aatatttccg gatcacctgg gtgagctttt ggcaccagtg ttcaagtcta    12240
cctgagatca gtgaactgga atctccgggg agaaggtagc catgctatat ttttaaaact    12300
caacctcttt ttcgattcct tatgcaaaag aagtcgagaa ccgtggttag aatgttagg     12360 tagggatcgt ggtgcggatg gtaggagctg agcatgtgtg agaccctggg ttagatccca    12420
gcaccaccat tcaaagaaga gggaaggctg gagagatggc tcagcggtta agagcactga    12480
ctgctcttcc aaaggtcctg agttcaattc tcagcaacca catggtggct cacaaccatc    12540
tgtaatggga tctgatgccc tcttctggtg tgtctgaaga cggcgacagt gtactcacat    12600
acataaaata aatctttaag atttattaag aggggagggg tgggcttgcg ttgtgttgt     12660 tttgcacttt gagcctagta tggtggtaca agttggtggc aaggaaaaat ctgaggctgc    12720
atcccatgtc tctaaggaca aactgggta ggagccagca atccgtaaat cttccgggac      12780
acggtgactt cctaaaacga ggttaatggt ccctgcgg gagaggagtc tgggtgtcca       12840
gactagtaca tttcttgctc ttttttttt taagtatttt aatttgtgtt aggtgtcaaa      12900
tccagtacaa atgccaagg tgcctattta ccatatcaaa gtggatctgg ccccctgcc       12960 aggttctccc agcatccctc agtccggagc tggggactga acccagggcc ttgtgcttcc    13020
taggcaagcg ctctaccact gagctaaatc cccaacccac atttcttgct cttaaaaaca    13080
tccttctgtt tattgatttt tgagacatct gccttccag tgccgaaatt atagacctgt     13140
accgtcactc ggtgtatgtg gtgctggggt ccaatctcca cggtactgat tgagctgtag    13200
tctcagtccg tacattcatc gttttcacag catcttacta caaagcttgc ctctggcctg    13260
ggacttgcta tgtagccttg aacttgtaca gatccacttg ctgctgcctc ctgagttgat    13320
```

```
gggcttaagt atatgccacc atgtctggtt ttttttttt  taattaaggg aaaaaaatgt    13380
tgtttgtggg caagtgtgtt aacagtgctg ggcaaaggtc agaggacaac tccgtggagt    13440
catttctctc cttctgcctt tatggggact ccagggatga aactcaggcc accaaactta    13500
caggccaagg cacccttacc ttttgagcca ttttttaaat aattgttttt gtggatatga    13560
gtgcaggtgc gcaagcgggc cagcaggggg caccagtgcg ctgctttacc tgggtgctgg    13620
gaactgaact ctgatcctgt gtgaaaacag atggctctgc cgccggaccc ttttttttt    13680 cttttttaat ttaaattatg tgtgtttgta tgtgagcttg gctaaggagt tgtcagatct    13740
cttgggtggg agttacaggc tttgtaggcc aaaagaagta atgctgggaa cggaactcag    13800
gttctgtgta atgctctttc ttaacgctga gccatctctc tgcagcctct catccatctt    13860
cttccatttc ctcctacatg ctacttttag aatcgctccc cagcccccac caactccacc    13920
accctcacgt tctcctccta gttagatatt ctgtgacgtt cgccttacgt cacagccccg    13980
ccctgagaac ttcgggcgcg                                                14000
```

```
<210> SEQ ID NO 17
<211> LENGTH: 11001
<212> TYPE: DNA
<213> ORGANISM: Macaca mulatta
<220> FEATURE:
<221> NAME/KEY: misc_feature
<222> LOCATION: (1990)..(2670)
<223> OTHER INFORMATION: n is a, c, g, or t
<220> FEATURE:
<221> NAME/KEY: misc_feature
<222> LOCATION: (5259)..(5278)
<223> OTHER INFORMATION: n is a, c, g, or t
<220> FEATURE:
<221> NAME/KEY: misc_feature
<222> LOCATION: (10180)..(11001)
<223> OTHER INFORMATION: n is a, c, g, or t

<400> SEQUENCE: 17
```

```
atgtaattaa agtcccaaat tgaccttaaa ataaggagaa tggcagggct aggtgcgctg      60
gctcacgcct gtaatcccag cgctttggga ggcgaacgcg ggcagaccac gaggtcagga     120
gatcgagacc atcctggcta acacagtgaa actctgtctc tactaaaaat acaaaaaatt     180
agcccggcgt ggtcgtggac acttgtattc ccagctactc gggaggctga ggcagaagaa     240
tggcgtgaac ccgggaggca gagcttgcag tgagctgaga tggcgccact gcactctagc     300
ctgggcgaca gagtgaaact ccatctcaaa aaaaaaaaaa aaaggagac  acatgaccag     360 aaatacaggc ctcagggagc cgaggatagc ccctggctga cagcctgcaa ggaagtaggg     420 acccccattcc tgcaaccata aggaactgaa ttctgcagac aacctgaatg agcttggaag    480
tgaatcttcc ccgtatggga tttttaaact acggagttgt gaattagtaa gtgggtactg     540
gccgggcaca gtggctcacg cctgtaatcc tagcactttg ggaggtcgag gagagtggat     600
cacctgagga caggagttcg agaccagcct ggacaacatg atgaaaccct gtgtctacta     660
aaaatacaaa aatgagctgg gcatggtggt ggttgcctgt aatcccagct acttgggagg     720
ctgaggcagg agaatcgctt gaacccggga ggcagaggct gcagtgagcc aagatcgtgc     780
catttcactc cagctgagca acaagagtga aactctgtct caaaaaaaga aaattaaaaa     840
aaaattgaaa atgggcattg ttgtaagctg ctgagtttat ggcaatttgt tacatgacaa     900
tagaaaacga acacacttcg cagtggactc caagatgccc gtgaaaggga gcttctcttt     960
gatctcctta acctcctcat ctccacagga cccagagcac aagaacgtcc cttctcctgc    1020
```

```
ttctagtccc accgtctaga aaagagagga ggagcccagc tcttcatcat tccaccccca   1080
cccactaact cccaacttcc tggccctcag cgggtgacca aggaagtcag tccacttggc   1140
tttccataaa cagcctgtgc cccaccaggc tcagggggc agcttgacca atccctattt    1200
ccaagacctt tggccaaccc tattgatctg gactcctggg cagacagttg gaccaacgga   1260
cagacgccat gaaggctctg ctgctcctgg ggttcctgct ggtgagcctg gagtcaacac   1320
tttcggtgag tgctgtggga accaggattg tcccaggatg gtcctggggt ggggcggtc    1380 gctatcacag ccatggtctc tgctcatgac ctgtgggttc aggtgactag gaggcctatg   1440
tggaaaggtg aggccagccc cgaaggccca ggcagaggag acagacaacc agactgggtg   1500
gatacaaggg cacagcctac atttctgggg gagatgggcc ttaagaagac aatgggagga   1560
ggtagaaagg gttgggtctt gggaggaaat ctctgcattt ctgggctgtg agaggaagct   1620
gcagactagc aacagatcgg tggcaggcta tgacttctag gcagttccct gccttctctc   1680
ccttgtagat tccaccttgg aaagcgccca aggagcataa gtacaaagct gaagagcaca   1740
cagtcggtaa gtggctcctc ctcctgagaa cccttgggtg gggatgtgta tggtgcagca   1800
tgtgcagtct caagacaatc tagtcttgtg cctacttggt gctaggtctt atgcccatgg   1860
gcaccagagt gatcgtgagc tgtgtgatcc ttgagggcag ggcataactg tgtctaagtg   1920
cccacgagcc tggctcagag caggtgcttg agatatgtgc tgctggtgcc atcacacctg   1980
ggatcctgcn nnnnnnnnn nnnnnnnnnn nnnnnnnnnn nnnnnnnnnn nnnnnnnnnn    2040
nnnnnnnnnn nnnnnnnnnn nnnnnnnnnn nnnnnnnnnn nnnnnnnnnn nnnnnnnnnn   2100
nnnnnnnnnn nnnnnnnnnn nnnnnnnnnn nnnnnnnnnn nnnnnnnnnn nnnnnnnnnn   2160
nnnnnnnnnn nnnnnnnnnn nnnnnnnnnn nnnnnnnnnn nnnnnnnnnn nnnnnnnnnn   2220
nnnnnnnnnn nnnnnnnnnn nnnnnnnnnn nnnnnnnnnn nnnnnnnnnn nnnnnnnnnn   2280
nnnnnnnnnn nnnnnnnnnn nnnnnnnnnn nnnnnnnnnn nnnnnnnnnn nnnnnnnnnn   2340
nnnnnnnnnn nnnnnnnnnn nnnnnnnnnn nnnnnnnnnn nnnnnnnnnn nnnnnnnnnn   2400
nnnnnnnnnn nnnnnnnnnn nnnnnnnnnn nnnnnnnnnn nnnnnnnnnn nnnnnnnnnn   2460
nnnnnnnnnn nnnnnnnnnn nnnnnnnnnn nnnnnnnnnn nnnnnnnnnn nnnnnnnnnn   2520
nnnnnnnnnn nnnnnnnnnn nnnnnnnnnn nnnnnnnnnn nnnnnnnnnn nnnnnnnnnn   2580
nnnnnnnnnn nnnnnnnnnn nnnnnnnnnn nnnnnnnnnn nnnnnnnnnn nnnnnnnnnn   2640
nnnnnnnnnn nnnnnnnnnn nnnnnnnnnn atgagctggg tgactctggg tgagaatcaa   2700
atctgagttc tctaagcttc aatttcccct tctgcgaaac caggttgata atagtaaacc   2760
tcttagggtt gttgagaagg aaaacccatg taaggcattc agcccatcac ctgaatggaa   2820
tggtgcatgg gaatggtgca tggaaatgct ttaaaaatat tagcttttat tggccgggcg   2880
cggtggctca gcctgtaat cccagcactt tgggaggctg aggcgggtgg atcacgaggt    2940
caggagatcg agaccatcct ggctaacatt gtgaaacccc gtctactact aaaatacaaa   3000
aaactagccc ggcatggtgg cgggcgcctg tagtcccagc tactcggagg ctgaggcggg   3060
agaatggcgt gaacccagga ggcggagctt gcagtgagcc gagatcgcgc cactgcactc   3120
cagcctgggc gacagagcga gactccgtct caaaaaaaaa aaaaaattag cttttattat   3180
taaactacct tttagatgag gggtacctgc catttccccc ttcctcaagc cctgccatag   3240 ctccctcattg ctttcattct tccagacact aaattaccta gaggtcaggc atggtggctc   3300
atgcttgtaa tcccagcact ttgggaggcc aaggcgggtg gatcacgagg tcaggagttc   3360
gagactggtc tggccaacat ggtgaaacgc tgtctctact aaaagtacaa aaattagcca   3420
```

```
ggcatggtgg catgtgcctg tagtcccagc tacttgggag gctgaggcag gagaattgct    3480
tgaacccagg aggatgaagg ttgcagtgaa tgaagatcac accattgcac tccagcttgg    3540
gcaaacagag caagagtctg tcaaagtgct gggcaacaga gcaagacact gtctcaaaaa    3600
aaaaagaaaa tttacctaga gcatgccaca tagcagggcc tgtgaaccag acagacccta    3660
acctggtggg cccgacttgg tggggttgag tccctaagca tggcattgag gcccagctca    3720
ttccaaccct ggactccctc agcctcctct cttcacccca cacccaaaag tttctcctcc    3780
ctcttgcctt acccaacctt ggtgccctat gcttgcctaa tgccctgcct agtgttcccc    3840
tcctctctgt ccgtccatcc catttgcatc ttttttttttt gggggggggg atggagtctc    3900
gctctgtccc ctaggctgga gtgtaatggc gccatcttgg ctcattgcaa tctccacctt    3960
ctgggttcaa gcagttttct gcctcagcct cccgagtagc tgggattaca ggaatgcacc    4020
ttcatgctca gctaattttt gtattttta gtggagatga ggtttcacca tgtcggccag    4080
gctggtctca aactcctgcc ctcaggtgat ccacccacct cagcctccca aagtgccggg    4140
attacaggca tgagccaccg cgcccagccg ccatttgcat cttataggtt catctcagat    4200
ccatttccat ttactgtcct ggttctggtt tggtacttgg caagtgcact ttgcctttaa    4260
caaaatagtg gcagaagctt attaagcagg tactatgtgc cagacactgc tcagcatttc    4320
atggcattat ctcatgaagc ctcacgacaa ttcctctgaa aagacacag gcaattctca    4380 ttattcgcgg tgattatgtt ctgtaaaatc acagtgaaca ttgaactggc aaacagtatt    4440
aggttcctgt gagcttctga tcacaacatt ttcatcaacc aacagtatat aatctcgttt    4500
tatgtgtgat tctgtttaaa gacgttttat ttaatatatg tgttgctgat tcatcaatgc    4560
taagctgatg gcactatagc tcacacctga atgaagtgga tctaacacat gctttctccc    4620
taaggtagcc ttcttgtgct taggaactat acaactcttt ttttttttttt tttttttttt    4680 ttgtgatgga gtctcgctct gtcgcccggg ttggagtgca gtggccggat ctcagctcac    4740
tgcaagctcc gcctcccggg tttacgccat tctcctgcct cagcctccgg agtagctggg    4800
actacaggcg cccgccacct cgcccggcta gttttttgta tttcttacta gagacggggt    4860
ttcaccggat tagccaggat ggtctcgatc tcctgacctc gtgatccgcc tgtctcggcc    4920
tcccaaagtg ctgggattac aggcttgagc caccgcgccc ggcctttttt ttttttttt    4980 gaaacggagt ctggctctgt cacccaggct ggagtgcagt ggccggatct cagctcactg    5040
caagctccgc ctcccgggtt tacgccattc tcctgcctca gcctcccgag tagctgggac    5100
tacaggcgcc cgccacctca cccggctagt ttttagtaga cggggtttt caccgtgtta    5160 cccaggatgg tcttgatctc ctgacctcgt gatccgcccg tctcggcctc ccaaagtgct    5220
gggattacag gcttgagcca ccgcgcccgg ccacggaann nnnnnnnnn nnnnnnnntg    5280 aaaaggacac tcgttcaata cgacagctga acaaaagca gcagtgtgac gccttgttga    5340
accttaactg ggagtgtgca aattttttac tgctctgtgc atgtccacaa atggccatga    5400
aagcatttca agtattgact tgggagttac aaataaaatt tagcaagtag gcatgttctc    5460
aaatatagaa ccagaaaata atgaggatca actgtagtat tattactgcc attttttcaga    5520 taaggaaacc aaggctcaga gtggttaaca ctgacttcaa cgttcaacaa gtattattaa    5580
gtgcctgctt tgtgacaagt gctcttcctg gccttgggac tgcagactta cccaaggtca    5640
cgcagctagc aggtggtgga gtcagtctac tccagctgtc tgagtcctaa acccaacttt    5700
tttttttttt ttttgagaca gagtctctct ctgtcaccca ggctggagtg cagtggcgtg    5760
```

```
atctcagctc actgcaagct ccgcctcctg ggttcacgcc attctcttgc ctcagcctcc   5820
caagtagcta ggactacagg cacccaccac catgcctggc taattttttt gtattttttag  5880 tagagacggg gtttcaccgt gttagccggg atggtctcaa tctcctgacc tcatgatccg   5940
cctgccgcgg cctcccaaag tgctgggatt acaggcttga gccaccgcgc ccggctctga   6000
acccaacttt taaagcagaa agtgttttca atgcacagcg gccttttgga gggtctgtcc   6060
tttcccaacc agaccctgag gggcagtgcc tgcacagttg agtacagggg aagtcctcag   6120
ggaatgtgtt gtccctgcag ttctcactgt caccggggag ccctgccact tccccttcca   6180
gtaccaccgg cggctgtacc acaaatgtac ccacaagggc cggccaggcc ctcagacctg   6240
gtaagactac gcagaggagt tggagcaggg gcctgggaga catgggccct ggctgtcctt   6300
ctaaggaact ctgctcagag agaggggggct gtgatagggg agggtgggcc aggcccctgg   6360
gcagagcagg gaagtcttgt ctctttctac aggtgtgcta ccaccctaa ctttgatgag   6420 gaccagcgat ggggatactg tgtggagccc aagaaagtga aggtgctac acacagcctc   6480 tggggtggcc cggggctctc tcctcccgcc tcattactct cctggtatca ccagacccca   6540
cacacctggg attctgggcc cagccccttc tctccctcca caatacccctt tggaagtcca   6600 gagggagagt tctgggaagg agtggtccca ttttgcaggt gggtaaacta agccttggaa   6660
acttggagta tcaaggtcac aaggcaagta ggttcaagta gggtgttggc ccccaactgt   6720
ctgactcagc tccctgctct tcctcccacc gtgtccatct ctcagaccac tgcagtaaac   6780
acagcccctg ccagaagggg gggacctgtg tgaacacgct gagtggcacc cactgtctct   6840
gtccacaaca cctcactggg aaccactgcc agagaggtga ggagacgctg aggacccggg   6900
cgggggtgct gggggacagg ggcaaccctg ggcctgcgga agaggtcgct ggataccagg   6960
agacttggca tggtcctaga ctctcctgag accactgtcc ctctttgtcc tcagagaagt   7020
gctttgagcc tcagcttctc cggttttttcc acgagaatga gatatggtat agatctgagc   7080
aagcagctgt ggccagatgc cagtgcaagg gtcctgatgc ccactgccag cggctggcca   7140
gccagggtga gcagatggtt gggaacgggc cagggaggag tgtcaggaag acaggctggc   7200
aggaggccgg gtgggcgtgcc gggaaggaga gctctctggg gggctcttta ggcccagggg   7260
tggctcactg cgttccctcc ccaagcctgc cgcaccaacc cgtgcctcca tgggggtcgc   7320
tgcctagagg tggagggcca ccgcctgtgc cactgccccg tgggctacac cggacccttc   7380
tgcgacttgg gtgagtgagg gtctggagga agcagaaggc cagcccccag gtgggacggg   7440
cttgccaggg aggaggaggg agagtgcaga aagcggatga gagggcggca ggagagccca   7500
gccctggctg cccagggagc cccctctctc cccagacacc aaggcgagct gctatgatgg   7560
ccgcgggctc agctaccgcg gcctggccag gaccacgctc tcgggtgcgc cctgtcagcc   7620
gtggacctcg gaggccacct actggaacgt gacggccgag caagcgcgga actggggact   7680
gggcggccac gccttctgcc ggtgcgccgc gtggggctgg gtgacccctc cgcccgaggg   7740
ccccgggctc ccggcgctct aacggcgccc cctcgtgtgg ctacaggaac ccggacaacg   7800
acatccgccc gtggtgcttc gtgctgatcg gcgacaggct aagctgggag tactgcgacg   7860
tggcacagtg ccaggcccca acccaggcgg cgcctccgac gccggtgtcc cctgggcttc   7920
atgtcccact catgcccccg cagccggcac cgccgaagct tcagcccacg acccggaccc   7980
cgcctcagtc ccagacccg ggaggttagg aagcgggggg aaggaggagc cgagagggct   8040
ctgggcggcg agctagattc cggccggcgg gccgcgggct ccgcgtcctc agccccggct   8100
cctccacagc cttgccagtg aagcaggagc agccgcctcg cctgacccgg aacggctcag   8160
```

-continued

```
tgagctgcgg gcagcggctc cgcaagagtc tgtcttcgat gacccgcgtc gttggcgggc    8220
tggtggcgct acgcggggcg cacccctaca tcgccgcgct gtactggggc cacagtttct    8280
gcgccggcag cctcatcgcc ccctgctggg tgctgacggc cgcccactgc ctgcaggacc    8340
ggcgagtacc tgcccgccca cgccgcgccc agggaccgcg gctcctccgt ctcccagcgc    8400
tgcttccacg ctgcacccga acccgtgccc taccttctcc cgccccaccc ttctttccac    8460
gcccctccag agctcccggg gaggaatctg aacacgaga tggggttcgg gagcaggggg    8520
cttccccaga acgcttgtgg ccaggtctga gcgttctgcc tctcccctac ccgcccgcag    8580
gccggcaccc gaggatctga cggtagtact cggccaggaa cgccataacc acagctgtga    8640
acagtgccag actctggccg tgcgctccta ccgcttgcac gaggccttct cgcccgacag    8700
ctaccagcac gacctgggtg cgtggggcg ccgcgcgggg acgggaagag aggatgggcc    8760
cccggcatcc ccgcctcacg ctcctctcgg cccgggttag ctctgttgcg ccttcaggag    8820
gatgcggacg gcagctgcgc gctcctgtcg ccttacgttc agccggtgtg cctgccaagc    8880
ggcgccgcgc gaccctccga gcccgcgctc tgccaggtgg ctggctgggg ccaccagttc    8940
gagggtaggc acaactgcta ggggcagggt aggagaggag gcctttgatc actgggttag    9000
gcaggagaag cccgcgactg tgttatcatt ccgggtgcct acagaatggg tggcgctgac    9060
ctgatgggtt gtgagaatgt gtagggccac ccagggcctg ggattcactg ctgggatccc    9120
ccaaatctcc tggggataca gggataatcg aacttgctct tggtttcctc tgggcgccgg    9180
gcttctaagt ccaactatga cgctgacccc gcgctccggg ctagtgtggg agccacgttc    9240
tgcgactctg gatgggtggt gggggtgggg tttctgtttc cgccccgccc attcaaatcc    9300
tggctcttcc ctggacctca gcttccttgc ctatgaaatt gaattaatgg catctcctcc    9360
ccctcgggct tgctgcaaga gaggaaggc atgagtgggt ttagcagcgc ctggcgcagc    9420
ttcgtccatc gtccgggcgg tgagcgttgt cagatggggt gtgaagaagg cgctcggtgt    9480
tcgcaggggc ggaggaatat tccagcttcc tgcaggaggc gcaggtaccc ttcctctccc    9540
tggagagctg ctcagcaccg gaggtgcacg gagcttccat cctccccggc atgtctgcg    9600 cagggttcct cgagggcggc accgatgcat gccaggtgag cccttagccc ggttggcgcc    9660
cttccccgag gccgtcaggc acaaatccca ggtccacagc actgagctgc gtgtttccga    9720
cccagggtga ttccggaggc ccgctggtgt gtgaggacca agccgcagag cgccggctca    9780
ccctgcaagg catcatcagc tggggatcgg gctgtggtga ccgcaacaag ccaggcgtct    9840
acaccgatgt ggcctactac ctggcctgga tccgggagca caccgcttcc tgattgctca    9900
gggactcatc tttccctcct cggtgattcc gcagtgggag actggctggg gcatggaagg    9960
caaaattgtg tccattccc ccaatgcggc cagctccgcg ccaggatggc gcaggaactc    10020
aataaagtgc tttgaaaatg ctgagaagga aagctctttt cttcatgggt cccgccggga    10080
gattccaaaa gagaaaagcg atttacagct tctccacagc tctcctttat gggaggtcta    10140
tgagatctta acgtgcaaaa tctagatgcc ggtccagctn nnnnnnnnn nnnnnnnnn     10200 nnnnnnnnnn nnnnnnnnnn nnnnnnnnnn nnnnnnnnnn nnnnnnnnnn nnnnnnnnnn    10260
nnnnnnnnnn nnnnnnnnnn nnnnnnnnnn nnnnnnnnnn nnnnnnnnnn nnnnnnnnnn    10320
nnnnnnnnnn nnnnnnnnnn nnnnnnnnnn nnnnnnnnnn nnnnnnnnnn nnnnnnnnnn    10380
nnnnnnnnnn nnnnnnnnnn nnnnnnnnnn nnnnnnnnnn nnnnnnnnnn nnnnnnnnnn    10440
nnnnnnnnnn nnnnnnnnnn nnnnnnnnnn nnnnnnnnnn nnnnnnnnnn nnnnnnnnnn    10500
```

| | | | | |
|---|---|---|---|---|
| nnnnnnnnnn nnnnnnnnnn nnnnnnnnnn nnnnnnnnnn nnnnnnnnnn nnnnnnnnnn | 10560 |
| nnnnnnnnnn nnnnnnnnnn nnnnnnnnnn nnnnnnnnnn nnnnnnnnnn nnnnnnnnnn | 10620 |
| nnnnnnnnnn nnnnnnnnnn nnnnnnnnnn nnnnnnnnnn nnnnnnnnnn nnnnnnnnnn | 10680 |
| nnnnnnnnnn nnnnnnnnnn nnnnnnnnnn nnnnnnnnnn nnnnnnnnnn nnnnnnnnnn | 10740 |
| nnnnnnnnnn nnnnnnnnnn nnnnnnnnnn nnnnnnnnnn nnnnnnnnnn nnnnnnnnnn | 10800 |
| nnnnnnnnnn nnnnnnnnnn nnnnnnnnnn nnnnnnnnnn nnnnnnnnnn nnnnnnnnnn | 10860 |
| nnnnnnnnnn nnnnnnnnnn nnnnnnnnnn nnnnnnnnnn nnnnnnnnnn nnnnnnnnnn | 10920 |
| nnnnnnnnnn nnnnnnnnnn nnnnnnnnnn nnnnnnnnnn nnnnnnnnnn nnnnnnnnnn | 10980 |
| nnnnnnnnnn nnnnnnnnnn n | 11001 |

<210> SEQ ID NO 18
<211> LENGTH: 2056
<212> TYPE: DNA
<213> ORGANISM: Macaca mulatta

<400> SEQUENCE: 18

```
ctattgatct ggactcctgg cagacagtt ggaccaacgg acagacgcc atg aag gct        58
                                                     Met Lys Ala
                                                      1 ctg ctg ctc ctg ggg ttc ctg ctg gtg agc ctg gag tca aca ctt tcg       106
Leu Leu Leu Leu Gly Phe Leu Leu Val Ser Leu Glu Ser Thr Leu Ser
 5                  10                  15 att cca cct tgg aaa gcg ccc aag gag cat aag tac aaa gct gaa gag       154
Ile Pro Pro Trp Lys Ala Pro Lys Glu His Lys Tyr Lys Ala Glu Glu
20                  25                  30                  35 cac aca gtc gtt ctc act gtc acc ggg gag ccc tgc cac ttc ccc ttc       202
His Thr Val Val Leu Thr Val Thr Gly Glu Pro Cys His Phe Pro Phe
                40                  45                  50 cag tac cac cgg cgg ctg tac cac aaa tgt acc cac aag ggc cgg cca       250
Gln Tyr His Arg Arg Leu Tyr His Lys Cys Thr His Lys Gly Arg Pro
            55                  60                  65 ggc cct cag acc tgg tgt gct acc acc cct aac ttt gat gag gac cag       298
Gly Pro Gln Thr Trp Cys Ala Thr Thr Pro Asn Phe Asp Glu Asp Gln
        70                  75                  80 cga tgg gga tac tgt gtg gag ccc aag aaa gtg aaa gac cac tgc agt       346
Arg Trp Gly Tyr Cys Val Glu Pro Lys Lys Val Lys Asp His Cys Ser
85                  90                  95 aaa cac agc ccc tgc cag aaa ggg ggg acc tgt gtg aac acg ctg agt       394
Lys His Ser Pro Cys Gln Lys Gly Gly Thr Cys Val Asn Thr Leu Ser
100                 105                 110                 115 ggc acc cac tgt ctc tgt cca caa cac ctc act ggg aac cac tgc cag       442
Gly Thr His Cys Leu Cys Pro Gln His Leu Thr Gly Asn His Cys Gln
                120                 125                 130 aga gag aag tgc ttt gag cct cag ctt ctc cgg ttt ttc cac gag aat       490
Arg Glu Lys Cys Phe Glu Pro Gln Leu Leu Arg Phe Phe His Glu Asn
            135                 140                 145 gag ata tgg tat aga tct gag caa gca gct gtg gcc aga tgc cag tgc       538
Glu Ile Trp Tyr Arg Ser Glu Gln Ala Ala Val Ala Arg Cys Gln Cys
        150                 155                 160 aag ggt cct gat gcc cac tgc cag cgg ctg gcc agc cag gcc tgc cgc       586
Lys Gly Pro Asp Ala His Cys Gln Arg Leu Ala Ser Gln Ala Cys Arg
    165                 170                 175 acc aac ccg tgc ctc cat ggg ggt cgc tgc cta gag gtg gag ggc cac       634
Thr Asn Pro Cys Leu His Gly Gly Arg Cys Leu Glu Val Glu Gly His
180                 185                 190                 195
```

-continued

| | | |
|---|---|---|
| cgc ctg tgc cac tgc ccc gtg ggc tac acc gga ccc ttc tgc gac ttg<br>Arg Leu Cys His Cys Pro Val Gly Tyr Thr Gly Pro Phe Cys Asp Leu<br>200 205 210 | 682 | |
| gac acc aag gcg agc tgc tat gat ggc cgc ggg ctc agc tac cgc ggc<br>Asp Thr Lys Ala Ser Cys Tyr Asp Gly Arg Gly Leu Ser Tyr Arg Gly<br>215 220 225 | 730 | |
| ctg gcc agg acc acg ctc tcg ggt gcg ccc tgt cag ccg tgg acc tcg<br>Leu Ala Arg Thr Thr Leu Ser Gly Ala Pro Cys Gln Pro Trp Thr Ser<br>230 235 240 | 778 | |
| gag gcc acc tac tgg aac gtg acg gcc gag caa gcg cgg aac tgg gga<br>Glu Ala Thr Tyr Trp Asn Val Thr Ala Glu Gln Ala Arg Asn Trp Gly<br>245 250 255 | 826 | |
| ctg ggc ggc cac gcc ttc tgc cgg aac ccg gac aac gac atc cgc ccg<br>Leu Gly Gly His Ala Phe Cys Arg Asn Pro Asp Asn Asp Ile Arg Pro<br>260 265 270 275 | 874 | |
| tgg tgc ttc gtg ctg atc ggc gac agg cta agc tgg gag tac tgc gac<br>Trp Cys Phe Val Leu Ile Gly Asp Arg Leu Ser Trp Glu Tyr Cys Asp<br>280 285 290 | 922 | |
| gtg gca cag tgc cag gcc cca acc cag gcg gcg cct ccg acg ccg gtg<br>Val Ala Gln Cys Gln Ala Pro Thr Gln Ala Ala Pro Pro Thr Pro Val<br>295 300 305 | 970 | |
| tcc cct ggg ctt cat gtc cca ctc atg ccc ccg cag ccg gca ccg ccg<br>Ser Pro Gly Leu His Val Pro Leu Met Pro Pro Gln Pro Ala Pro Pro<br>310 315 320 | 1018 | |
| aag ctt cag ccc acg acc cgg acc ccg cct cag tcc cag acc ccg gga<br>Lys Leu Gln Pro Thr Thr Arg Thr Pro Pro Gln Ser Gln Thr Pro Gly<br>325 330 335 | 1066 | |
| gcc ttg cca gtg aag cag gag cag ccg cct cgc ctg acc cgg aac ggc<br>Ala Leu Pro Val Lys Gln Glu Gln Pro Pro Arg Leu Thr Arg Asn Gly<br>340 345 350 355 | 1114 | |
| tca gtg agc tgc ggg cag cgg ctc cgc aag agt ctg tct tcg atg acc<br>Ser Val Ser Cys Gly Gln Arg Leu Arg Lys Ser Leu Ser Ser Met Thr<br>360 365 370 | 1162 | |
| cgc gtc gtt ggc ggg ctg gtg gcg cta cgc ggg gcg cac ccc tac atc<br>Arg Val Val Gly Gly Leu Val Ala Leu Arg Gly Ala His Pro Tyr Ile<br>375 380 385 | 1210 | |
| gcc gcg ctg tac tgg ggc cac agt ttc tgc gcc ggc agc ctc atc gcc<br>Ala Ala Leu Tyr Trp Gly His Ser Phe Cys Ala Gly Ser Leu Ile Ala<br>390 395 400 | 1258 | |
| ccc tgc tgg gtg ctg acg gcc gcc cac tgc ctg cag gac cgg ccg gca<br>Pro Cys Trp Val Leu Thr Ala Ala His Cys Leu Gln Asp Arg Pro Ala<br>405 410 415 | 1306 | |
| ccc gag gat ctg acg gta gta ctc ggc cag gaa cgc cat aac cac agc<br>Pro Glu Asp Leu Thr Val Val Leu Gly Gln Glu Arg His Asn His Ser<br>420 425 430 435 | 1354 | |
| tgt gaa cag tgc cag act ctg gcc gtg cgc tcc tac cgc ttg cac gag<br>Cys Glu Gln Cys Gln Thr Leu Ala Val Arg Ser Tyr Arg Leu His Glu<br>440 445 450 | 1402 | |
| gcc ttc tcg ccc gac agc tac cag cac gac ctg gct ctg ttg cgc ctt<br>Ala Phe Ser Pro Asp Ser Tyr Gln His Asp Leu Ala Leu Leu Arg Leu<br>455 460 465 | 1450 | |
| cag gag gat gcg gac ggc agc tgc gcg ctc ctg tcg cct tac gtt cag<br>Gln Glu Asp Ala Asp Gly Ser Cys Ala Leu Leu Ser Pro Tyr Val Gln<br>470 475 480 | 1498 | |
| ccg gtg tgc ctg cca agc ggc gcc gcg cga ccc tcc gag ccc gcg ctc<br>Pro Val Cys Leu Pro Ser Gly Ala Ala Arg Pro Ser Glu Pro Ala Leu<br>485 490 495 | 1546 | |
| tgc cag gtg gct ggc tgg ggc cac cag ttc gag ggg gcg gag gaa tat<br>Cys Gln Val Ala Gly Trp Gly His Gln Phe Glu Gly Ala Glu Glu Tyr<br>500 505 510 515 | 1594 | |

| | | | | | | | | | | | | | | | | |
|---|---|---|---|---|---|---|---|---|---|---|---|---|---|---|---|---|
| tcc | agc | ttc | ctg | cag | gag | gcg | cag | gta | ccc | ttc | ctc | tcc | ctg | gag | agc | 1642 |
| Ser | Ser | Phe | Leu | Gln | Glu | Ala | Gln | Val | Pro | Phe | Leu | Ser | Leu | Glu | Ser | |
| | | | 520 | | | | | 525 | | | | | 530 | | | |
| tgc | tca | gca | ccg | gag | gtg | cac | gga | gct | tcc | atc | ctc | ccc | ggc | atg | ctc | 1690 |
| Cys | Ser | Ala | Pro | Glu | Val | His | Gly | Ala | Ser | Ile | Leu | Pro | Gly | Met | Leu | |
| | | 535 | | | | | 540 | | | | | 545 | | | | |
| tgc | gca | ggg | ttc | ctc | gag | ggc | ggc | acc | gat | gca | tgc | cag | ggt | gat | tcc | 1738 |
| Cys | Ala | Gly | Phe | Leu | Glu | Gly | Gly | Thr | Asp | Ala | Cys | Gln | Gly | Asp | Ser | |
| | | 550 | | | | | 555 | | | | | 560 | | | | |
| gga | ggc | ccg | ctg | gtg | tgt | gag | gac | caa | gcc | gca | gag | cgc | cgg | ctc | acc | 1786 |
| Gly | Gly | Pro | Leu | Val | Cys | Glu | Asp | Gln | Ala | Ala | Glu | Arg | Arg | Leu | Thr | |
| | 565 | | | | | 570 | | | | | 575 | | | | | |
| ctg | caa | ggc | atc | atc | agc | tgg | gga | tcg | ggc | tgt | ggt | gac | cgc | aac | aag | 1834 |
| Leu | Gln | Gly | Ile | Ile | Ser | Trp | Gly | Ser | Gly | Cys | Gly | Asp | Arg | Asn | Lys | |
| 580 | | | | | 585 | | | | | 590 | | | | | 595 | |
| cca | ggc | gtc | tac | acc | gat | gtg | gcc | tac | tac | ctg | gcc | tgg | atc | cgg | gag | 1882 |
| Pro | Gly | Val | Tyr | Thr | Asp | Val | Ala | Tyr | Tyr | Leu | Ala | Trp | Ile | Arg | Glu | |
| | | | 600 | | | | | 605 | | | | | 610 | | | |
| cac | acc | gct | tcc | tga | ttgctcaggg | actcatcttt | ccctcctcgg | tgattccgca | | | | | | | | 1937 |
| His | Thr | Ala | Ser | | | | | | | | | | | | | |
| | | | 615 | | | | | | | | | | | | | | gtgggagact ggctggggca tggaaggcaa aattgtgtcc cattccccca atgcggccag    1997 ctccgcgcca ggatggcgca ggaactcaat aaagtgcttt gaaaatgctg agaaggaaa    2056

<210> SEQ ID NO 19
<211> LENGTH: 2056
<212> TYPE: DNA
<213> ORGANISM: Papio hamadryas
<220> FEATURE:
<221> NAME/KEY: misc_feature
<222> LOCATION: (1730)..(1874)
<223> OTHER INFORMATION: n is a, c, g, or t

<400> SEQUENCE: 19
ctattgatct ggactcctgg gcaggcagtt ggaccaacgg acagacgcca tgagggctct    60
gctgctcctg gggttcctgc tggtgagcct ggagtcaaca ctttcgattc caccttggaa    120
agcacccaag gagcataagt acaaagctga agagcacaca gtcgttctca ctgtcaccgg    180
ggagccctgc cacttcccct tccagtacca ccggcggctg taccacaaat gtacccacaa    240
gggccggcca ggccctcaga cctggtgtgc taccagccct aactttgatg aggaccaacg    300
atggggatac tgtgtggagc ccaagaaagt gaaagaccac tgcagtaaac acagcccctg    360
ccagaaaggg gggacctgtg tgaacacgct gagtggcacc cactgtctct gtccacaaca    420
cctcactggg aaccactgcc agagagagaa gtgctttgag cctcagcttc tccggttttt    480
ccacgagaat gagatatggt atagatctga gcaagcagct gtggccagat gccagtgcaa    540
gggtcctgat gccactgcca gcagctggc cagccaggcc tgccgcacca cccgtgcct    600 ccatgggggt cgctgcctag aggtggaggg ccaccgcctg tgccactgcc cgtgggcta    660 caccggaccc ttctgcgact tggacaccaa ggcgagctgc tatgatggcc gcgggctcag    720
ctaccgcggc ctggccagga ccacgctctc gggtgcgccc tgtcagccgt ggacctcgga    780
ggccacctac cggaacgtga cggccgagca agcgcggaac tggggactgg gcggccacgc    840
cttctgccgg aacccggaca acgacatccg cccgtggtgc ttcgtgctga tcggcgacag    900
gctaagctgg gagtactgcg acgtggcaca gtgccaggcc caacccagg cggcgcctcc    960 gaccccagtg tccctgggc ttcatgtccc actcatgccc ccgcagccgg caccgccgaa    1020

```
gcttcagccc acgacccgga ccccgcctca gtcccagacc ccgggagcct tgccagtgaa    1080
gcaggagcag ccgcctcgcc tgacccggaa cggctcagtg agctgcgggc agcggctccg    1140
caagagtctg tcttcgatga cccgcgtcgt tggcgggctg gtggcgctac gcggggcgca    1200
cccctacatc gccgcgctgt actggggcca cagtttctgc gccggcagcc tcatcgcccc    1260
ctgctgggtg ctgacggctg ctcactgcct gcaggaccgg ccggcacccg aggatctgac    1320
ggtagtactc ggccaggaac gccataacca cagctgtgaa cagtgccaga ctctggccgt    1380
gcgctcctac cgcttgcacg aggccttctc gcccgtcagc taccagcacg acctggctct    1440
gttgcgcctt caggaggatg cggacggcag ctgcgcgctc ctgtcgcctt acgttcagcc    1500
ggtgtgcctg ccaagcggcg ccgcgcgacc ctccgagccc gcgctctgcc aggtggctgg    1560
ctggggccac cagttcgagg ggcgggagga atattccagc ttcctgcagg aggcgcaggt    1620
acccttcctc tccctggagc gctgctcagc accggacgtg cacggagcct ccatcctccc    1680
cggcatgctc tgcgcagggt tcctcgaggg cggcaccgat gcatgccagn nnnnnnnnn    1740 nnnnnnnnnn nnnnnnnnnn nnnnnnnnnn nnnnnnnnnn nnnnnnnnnn nnnnnnnnnn    1800
nnnnnnnnnn nnnnnnnnnn nnnnnnnnnn nnnnnnnnnn nnnnnnnnnn nnnnnnnnnn    1860
nnnnnnnnnn nnnnagtttg gttaggtaag tttcatcaag ctcagggact catctttccc    1920
tcctcggtga ttccgcagtg ggagagtggc tggggcatgg aaggcaaaat tgtgtcccat    1980
tcccccaatg cggccagctc cgcgccagga tggcgcagga actcaataaa gtgctttgaa    2040
aatgctgaga aggaaa                                                    2056

<210> SEQ ID NO 20
<211> LENGTH: 648
<212> TYPE: DNA
<213> ORGANISM: Macaca fascicularis
<220> FEATURE:
<221> NAME/KEY: CDS
<222> LOCATION: (303)..(623)

<400> SEQUENCE: 20
aaaaaaaaaa aaaaaaaaaa aaaaaaaaaa aaaaaaaaaa aaaaaaaaaa aaaaaaaaaa      60
aaaaataaaa aaaacgttc acccggtgtg cctgccaagc ggcgccgcgc gaccctccga     120
gcccgcgctc tgccaggtgg ctggctgggg ccaccagttc gagggggcgg aggaatattc     180
cagcttcctg caggaggcgc aggtacccct tcctctccctg gagagctgct cagcaccgga    240
ggtgcacgga gcctccatcc tccccggcat gctctgcgca gggttcctcg agggcggcac    300
```

| cg atg cat gcc agg gtg att ccg gag gcc cgc tgg tgt gtg agg acc | 347 |
|---|---|
| Met His Ala Arg Val Ile Pro Glu Ala Arg Trp Cys Val Arg Thr | |
| 1               5                  10                 15 | |

| aag ccg cag agc gcc ggc tca ccc tgc aag gca tca tca gct ggg gat | 395 |
|---|---|
| Lys Pro Gln Ser Ala Gly Ser Pro Cys Lys Ala Ser Ser Ala Gly Asp | |
|         20                  25                  30 | |

| cgg gct gtg gtg acc gca aca agc cag gcg tct aca ccg atg tgg cct | 443 |
|---|---|
| Arg Ala Val Val Thr Ala Thr Ser Gln Ala Ser Thr Pro Met Trp Pro | |
|         35                  40                  45 | |

| act acc tgg cct gga tcc ggg agc aca ccg ctt cct gat tgc tca ggg | 491 |
|---|---|
| Thr Thr Trp Pro Gly Ser Gly Ser Thr Pro Leu Pro Asp Cys Ser Gly | |
|     50                  55                  60 | |

| act cat ctt tcc ctc ctc ggt gat tcc gca gtg gga gac tgg ctg ggg | 539 |
|---|---|
| Thr His Leu Ser Leu Leu Gly Asp Ser Ala Val Gly Asp Trp Leu Gly | |
| 65                  70                  75 | |

| | |
|---|---|
| cat gga agg caa aat tgt gtc cca ttc ccc caa tgc ggc cag ctc cgc<br>His Gly Arg Gln Asn Cys Val Pro Phe Pro Gln Cys Gly Gln Leu Arg<br>80                           85                              90                       95 | 587 |
| gcc agg atg gcg cag gaa ctc aat aaa gtg ctt tga aaatgctgaa<br>Ala Arg Met Ala Gln Glu Leu Asn Lys Val Leu<br>                            100                             105 | 633 |
| aaaaaaaaaa aaaaa | 648 |

```
<210> SEQ ID NO 21
<211> LENGTH: 1837
<212> TYPE: DNA
<213> ORGANISM: Mus musculus
<220> FEATURE:
<221> NAME/KEY: CDS
<222> LOCATION: (92)..(1606)

<400> SEQUENCE: 21
```

| | |
|---|---|
| actgattctc tgcgactgtc tgctcagtct gtcctgaagc tgcctagtga ccaagaactt | 60 |
| ggaccaggac gcagctgaca tcgctgccca g atg gcc tcc agg ctg acc cca<br>                                                    Met Ala Ser Arg Leu Thr Pro<br>                                                      1                        5 | 112 |
| ctg acc ctc ctg ctg ctg ctg gct ggg gat aga gcc ttc tca gat<br>Leu Thr Leu Leu Leu Leu Leu Ala Gly Asp Arg Ala Phe Ser Asp<br>          10                      15                        20 | 160 |
| ccc gaa gct acc agc cac agc acc cag gat cca ctg gag gct caa gcg<br>Pro Glu Ala Thr Ser His Ser Thr Gln Asp Pro Leu Glu Ala Gln Ala<br> 25                          30                              35 | 208 |
| aaa agc aga gag agc ttc cct gaa aga gat gac tcc tgg agt ccc cca<br>Lys Ser Arg Glu Ser Phe Pro Glu Arg Asp Asp Ser Trp Ser Pro Pro<br>40                         45                              50                        55 | 256 |
| gag cct aca gta ctg ccc tct acc tgg cca aca acc agt gta gcc atc<br>Glu Pro Thr Val Leu Pro Ser Thr Trp Pro Thr Thr Ser Val Ala Ile<br>                    60                              65                              70 | 304 |
| aca ata aca aat gac acc atg ggt aaa gta gcc aac gag tcc ttc agc<br>Thr Ile Thr Asn Asp Thr Met Gly Lys Val Ala Asn Glu Ser Phe Ser<br>               75                              80                              85 | 352 |
| cag cac agc cag cca gct gct cag cta ccc aca gat tct cca gga cag<br>Gln His Ser Gln Pro Ala Ala Gln Leu Pro Thr Asp Ser Pro Gly Gln<br>                    90                              95                              100 | 400 |
| ccc cct ctg aat tct tcc agc cag ccc tcc act gcc tca gat ctt ccc<br>Pro Pro Leu Asn Ser Ser Ser Gln Pro Ser Thr Ala Ser Asp Leu Pro<br>105                          110                              115 | 448 |
| acc cag gct act act gaa ccc ttc tgc ccg gag ccg ctt gct cag tgc<br>Thr Gln Ala Thr Thr Glu Pro Phe Cys Pro Glu Pro Leu Ala Gln Cys<br>120                       125                              130                        135 | 496 |
| tct gat tca gac aga gac tcc tca gag gca aag ctc tca gag gct ttg<br>Ser Asp Ser Asp Arg Asp Ser Ser Glu Ala Lys Leu Ser Glu Ala Leu<br>                    140                              145                              150 | 544 |
| aca gat ttc tct gtg aag ctc tac cac gcc ttc tca gct acc aag atg<br>Thr Asp Phe Ser Val Lys Leu Tyr His Ala Phe Ser Ala Thr Lys Met<br>               155                              160                              165 | 592 |
| gct aag acc aac atg gcc ttt tcc cca ttc agc att gcc agc ctc ctc<br>Ala Lys Thr Asn Met Ala Phe Ser Pro Phe Ser Ile Ala Ser Leu Leu<br>                    170                              175                              180 | 640 |
| aca cag gtt ctt ctt ggg gct gga gac agc acc aag agc aac ttg gag<br>Thr Gln Val Leu Leu Gly Ala Gly Asp Ser Thr Lys Ser Asn Leu Glu<br>               185                              190                              195 | 688 |
| agc atc ctt tcc tac ccc aag gat ttt gcc tgt gtc cac caa gca cta<br>Ser Ile Leu Ser Tyr Pro Lys Asp Phe Ala Cys Val His Gln Ala Leu<br>200                          205                              210                        215 | 736 |

```
aag ggc ttt tca tcc aaa ggt gtc act tct gtg tct cag att ttc cac      784
Lys Gly Phe Ser Ser Lys Gly Val Thr Ser Val Ser Gln Ile Phe His
                220             225             230 agc cca gat ctg gcc ata agg gac acc tat gtg aat gca tct cag agc      832
Ser Pro Asp Leu Ala Ile Arg Asp Thr Tyr Val Asn Ala Ser Gln Ser
            235             240             245 ctg tat gga agc agc ccc aga gtc ctg ggc cca gac agt gct gct aac      880
Leu Tyr Gly Ser Ser Pro Arg Val Leu Gly Pro Asp Ser Ala Ala Asn
        250             255             260 tta gaa ctc atc aac acc tgg gtg gct gag aac acc aac cat aag atc      928
Leu Glu Leu Ile Asn Thr Trp Val Ala Glu Asn Thr Asn His Lys Ile
    265             270             275 cgc aag ctg ctg gac agc ctg cct tct gac acc tgc ctc gtc ctt ctc      976
Arg Lys Leu Leu Asp Ser Leu Pro Ser Asp Thr Cys Leu Val Leu Leu
280             285             290             295 aat gct gtc tac ttg agt gcc aag tgg aag ata aca ttt gaa cca aaa     1024
Asn Ala Val Tyr Leu Ser Ala Lys Trp Lys Ile Thr Phe Glu Pro Lys
                300             305             310 aag atg atg gcg cct ttc ttc tac aaa aac tct atg att aaa gtg ccc     1072
Lys Met Met Ala Pro Phe Phe Tyr Lys Asn Ser Met Ile Lys Val Pro
            315             320             325 atg atg agt agc gta aag tac cct gtg gcc caa ttc gat gac cat act     1120
Met Met Ser Ser Val Lys Tyr Pro Val Ala Gln Phe Asp Asp His Thr
        330             335             340 ttg aag gcc aag gtg gga cag ctg cag ctc tct cac aac ctg agc ttt     1168
Leu Lys Ala Lys Val Gly Gln Leu Gln Leu Ser His Asn Leu Ser Phe
    345             350             355 gtg atc gtg gta ccc gtg ttc cca aag cac caa ctt aaa gat gta gaa     1216
Val Ile Val Val Pro Val Phe Pro Lys His Gln Leu Lys Asp Val Glu
360             365             370             375 aag gct ctc aac ccc act gtc ttc aag gcc atc atg aag aag ctg gag     1264
Lys Ala Leu Asn Pro Thr Val Phe Lys Ala Ile Met Lys Lys Leu Glu
                380             385             390 ctg tcc aaa ttc ctg ccc act tac ctg acg atg cct cat ata aaa gta     1312
Leu Ser Lys Phe Leu Pro Thr Tyr Leu Thr Met Pro His Ile Lys Val
            395             400             405 aag agc agc caa gac atg ctg tca gtc atg gag aaa ctg gaa ttc ttt     1360
Lys Ser Ser Gln Asp Met Leu Ser Val Met Glu Lys Leu Glu Phe Phe
        410             415             420 gac ttc act tac gat ctc aac ctg tgc ggg ctg acc gag gac cca gat     1408
Asp Phe Thr Tyr Asp Leu Asn Leu Cys Gly Leu Thr Glu Asp Pro Asp
    425             430             435 ctt cag gtg tct gcc atg aaa cac gag aca gtg ctg gaa ctg aca gag     1456
Leu Gln Val Ser Ala Met Lys His Glu Thr Val Leu Glu Leu Thr Glu
440             445             450             455 tca ggg gtg gaa gca gct gca gcc tct gcc atc tcc ttt ggc cga agc     1504
Ser Gly Val Glu Ala Ala Ala Ala Ser Ala Ile Ser Phe Gly Arg Ser
                460             465             470 tta ccc atc ttt gag gtg cag cga cct ttc ctc ttc ctg ctc tgg gac     1552
Leu Pro Ile Phe Glu Val Gln Arg Pro Phe Leu Phe Leu Leu Trp Asp
            475             480             485 cag caa cac agg ttc cca gtc ttc atg ggt cgt gta tat gac ccc agg     1600
Gln Gln His Arg Phe Pro Val Phe Met Gly Arg Val Tyr Asp Pro Arg
        490             495             500 ggt tga gacaggcttg ggtaaacatt gtcacccaag cttcagctcc tccggttatt     1656
Gly tccttgccac tgcctgcccg agccacttca agccttagga actggcagac ggaactgttt     1716
ccatccacca accccagggg tatcaaccac tttttttgcag cttttacggt tcaaacctat     1776
```

```
caaactctac aaataaaact tgcagacatt ttcttctctc actaaaaaaa aaaaaaaaa      1836 a                                                                    1837
```

<210> SEQ ID NO 22
<211> LENGTH: 24
<212> TYPE: DNA
<213> ORGANISM: Artificial sequence
<220> FEATURE:
<223> OTHER INFORMATION: Primer

<400> SEQUENCE: 22

```
caaaggaggg acatgtatca acac                                             24
```

<210> SEQ ID NO 23
<211> LENGTH: 20
<212> TYPE: DNA
<213> ORGANISM: Artificial sequence
<220> FEATURE:
<223> OTHER INFORMATION: Primer

<400> SEQUENCE: 23

```
ctggcaatgt ttcccagtga                                                  20
```

<210> SEQ ID NO 24
<211> LENGTH: 24
<212> TYPE: DNA
<213> ORGANISM: Artificial sequence
<220> FEATURE:
<223> OTHER INFORMATION: Probe

<400> SEQUENCE: 24

```
cccaatgggc cacactgtct ctgc                                             24
```

<210> SEQ ID NO 25
<211> LENGTH: 21
<212> TYPE: DNA
<213> ORGANISM: Artificial sequence
<220> FEATURE:
<223> OTHER INFORMATION: Primer

<400> SEQUENCE: 25

```
gagtccccca gagcctacag t                                                21
```

<210> SEQ ID NO 26
<211> LENGTH: 26
<212> TYPE: DNA
<213> ORGANISM: Artificial sequence
<220> FEATURE:
<223> OTHER INFORMATION: Primer

<400> SEQUENCE: 26

```
tgtcatttgt tattgtgatg gctaca                                           26
```

<210> SEQ ID NO 27
<211> LENGTH: 25
<212> TYPE: DNA
<213> ORGANISM: Artificial sequence
<220> FEATURE:
<223> OTHER INFORMATION: Probe

<400> SEQUENCE: 27

```
ctgccctcta cctggccaac aacca                                            25
```

<210> SEQ ID NO 28
<211> LENGTH: 24

```
<212> TYPE: DNA
<213> ORGANISM: Artificial sequence
<220> FEATURE:
<223> OTHER INFORMATION: Primer

<400> SEQUENCE: 28
caaaggaggg acatgtatca acac                                          24

<210> SEQ ID NO 29
<211> LENGTH: 20
<212> TYPE: DNA
<213> ORGANISM: Artificial sequence
<220> FEATURE:
<223> OTHER INFORMATION: Primer

<400> SEQUENCE: 29
ctggcaatgt ttcccagtga                                               20

<210> SEQ ID NO 30
<211> LENGTH: 24
<212> TYPE: DNA
<213> ORGANISM: Artificial sequence
<220> FEATURE:
<223> OTHER INFORMATION: Probe

<400> SEQUENCE: 30
cccaatgggc cacactgtct ctgc                                          24

<210> SEQ ID NO 31

<400> SEQUENCE: 31

000

<210> SEQ ID NO 32

<400> SEQUENCE: 32

000

<210> SEQ ID NO 33

<400> SEQUENCE: 33

000

<210> SEQ ID NO 34

<400> SEQUENCE: 34

000

<210> SEQ ID NO 35

<400> SEQUENCE: 35

000

<210> SEQ ID NO 36

<400> SEQUENCE: 36

000

<210> SEQ ID NO 37

<400> SEQUENCE: 37
```

```
000

<210> SEQ ID NO 38
<400> SEQUENCE: 38

000

<210> SEQ ID NO 39
<400> SEQUENCE: 39

000

<210> SEQ ID NO 40
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 40
gcatgggaca gagatggtgc                                               20

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
aaagtggttg ataccctggg                                               20

<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 42
ccttccctga aggttcctcc                                               20

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
ggcatattgg tttttggaat                                               20
```